(12) United States Patent  
Annis

(10) Patent No.: US 10,160,731 B2  
(45) Date of Patent: *Dec. 25, 2018

(54) METHOD FOR PREPARING 3-TRIFLUOROMETHYL CHALCONES

(71) Applicant: E.I. DU PONT DE NEMOURS AND COMPANY, Wilmington, DE (US)

(72) Inventor: Gary David Annis, Landenberg, PA (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/946,601

(22) Filed: Apr. 5, 2018

(65) Prior Publication Data

US 2018/0222873 A1  Aug. 9, 2018

Related U.S. Application Data

(62) Division of application No. 15/798,330, filed on Oct. 30, 2017, now Pat. No. 9,938,248, which is a division (Continued)

(51) Int. Cl.  
*C07D 261/04* (2006.01)  
*C07C 17/35* (2006.01)  
(Continued)

(52) U.S. Cl.  
CPC ............ *C07D 261/04* (2013.01); *C07C 17/35* (2013.01); *C07C 25/13* (2013.01); *C07C 45/455* (2013.01);  
(Continued)

(58) Field of Classification Search  
CPC .. C07D 261/04; C07D 231/12; C07D 231/14; C07D 231/16; C07D 249/08; C07D 249/10; C07D 277/28; C07D 213/40; C07C 17/35; C07C 45/455; C07C 45/70; C07C 49/80; C07C 49/813; C07C 67/343; C07C 205/45; C07C 209/74; C07C 231/12; C07C 231/14; C07C 235/84  
USPC .......................................................... 548/240  
See application file for complete search history.

(56) References Cited

U.S. PATENT DOCUMENTS 3,879,532 A  4/1975 Hass et al.  
4,129,568 A  12/1978 Howe  
(Continued)

FOREIGN PATENT DOCUMENTS

CA  2252543 A1  11/1997  
CA  2558848 A1  9/2005  
(Continued)

OTHER PUBLICATIONS

Office Action dated Jun. 8, 2012 received in copending U.S. Appl. No. 12/663,848.

(Continued)

*Primary Examiner* — Kristin A Vajda

(57) ABSTRACT

Disclosed is a method for preparing a compound of Formula 1 wherein Q and Z are as defined in the disclosure comprising distilling water from a mixture comprising a compound of Formula 2, a compound of Formula 3, a base comprising at least one compound selected from the group consisting of alkaline earth metal hydroxides of Formula 4 wherein M is Ca, Sr or Ba, alkali metal carbonates of Formula 4a wherein $M^1$ is Li, Na or K, 1,5-diazabicyclo[4.3.0]non-5-ene and 1,8-diazabicyclo[5.4.0]undec-7-ene, and an aprotic solvent capable of forming a low-boiling azeotrope with water. Also disclosed is a method for preparing a compound of Formula 2 comprising (1) forming a reaction mixture comprising a Grignard reagent derived from contacting a compound of Formula 5 wherein X is Cl, Br or I with magnesium metal or an alkylmagnesium halide in the presence of an ethereal solvent, and then (2) contacting the reaction mixture with a compound of Formula 6 wherein Y is $OR^{11}$ or $NR^{12}R^{13}$, and $R^{11}$, $R^{12}$ and $R^{13}$ are as defined in the disclosure. Further disclosed is a method for preparing a compound of Formula 7 wherein Q and Z are as defined in the disclosure, using a compound of Formula 1 characterized by preparing the compound of Formula 1 by the method disclosed above or using a compound of Formula 1 prepared by the method disclosed above.

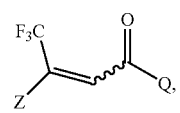

1

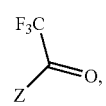

2

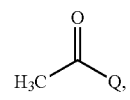

3

M(OH)$_2$,  
4

(M$^1$)$_2$CO$_3$  
4a

Z—X,  
5

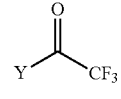

6

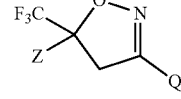

7

8 Claims, No Drawings

Related U.S. Application Data of application No. 15/455,691, filed on Mar. 10, 2017, now Pat. No. 9,834,523, which is a division of application No. 14/683,423, filed on Apr. 10, 2015, now Pat. No. 9,611,231, which is a division of application No. 14/041,938, filed on Sep. 30, 2013, now Pat. No. 9,035,101, which is a division of application No. 12/933,493, filed as application No. PCT/US2009/039832 on Apr. 8, 2009, now Pat. No. 8,546,618.

(60) Provisional application No. 61/080,437, filed on Jul. 14, 2008, provisional application No. 61/043,452, filed on Apr. 9, 2008.

(51) Int. Cl.

| | |
|---|---|
| *C07C 45/45* | (2006.01) |
| *C07C 45/70* | (2006.01) |
| *C07C 49/80* | (2006.01) |
| *C07C 49/813* | (2006.01) |
| *C07C 67/343* | (2006.01) |
| *C07C 205/45* | (2006.01) |
| *C07C 209/74* | (2006.01) |
| *C07C 231/12* | (2006.01) |
| *C07C 235/84* | (2006.01) |
| *C07D 213/40* | (2006.01) |
| *C07D 231/12* | (2006.01) |
| *C07D 231/14* | (2006.01) |
| *C07D 231/16* | (2006.01) |
| *C07D 249/08* | (2006.01) |
| *C07D 249/10* | (2006.01) |
| *C07D 277/28* | (2006.01) |
| *C07C 25/13* | (2006.01) |
| *C07C 231/14* | (2006.01) |

(52) U.S. Cl.
CPC .............. *C07C 45/70* (2013.01); *C07C 49/80* (2013.01); *C07C 49/813* (2013.01); *C07C 67/343* (2013.01); *C07C 205/45* (2013.01); *C07C 209/74* (2013.01); *C07C 231/12* (2013.01); *C07C 231/14* (2013.01); *C07C 235/84* (2013.01); *C07D 213/40* (2013.01); *C07D 231/12* (2013.01); *C07D 231/14* (2013.01); *C07D 231/16* (2013.01); *C07D 249/08* (2013.01); *C07D 249/10* (2013.01); *C07D 277/28* (2013.01)

(56) References Cited

U.S. PATENT DOCUMENTS

| | | |
|---|---|---|
| 6,645,984 B2 | 11/2003 | Braun et al. |
| 7,662,972 B2 | 2/2010 | Mita et al. |
| 7,897,630 B2 | 3/2011 | Lahm et al. |
| 7,947,715 B2 | 5/2011 | Mita et al. |
| 7,951,828 B1 | 5/2011 | Mita et al. |
| 7,964,204 B2 | 6/2011 | Lahm et al. |
| 8,022,089 B2 | 9/2011 | Mita et al. |
| 8,138,213 B2 | 3/2012 | Mita et al. |
| 8,217,180 B2 | 7/2012 | Annis et al. |
| 8,231,888 B2 | 7/2012 | Lahm et al. |
| 8,410,153 B2 | 4/2013 | Lahm et al. |
| 8,513,431 B2 | 8/2013 | Annis et al. |
| 8,546,618 B2 | 10/2013 | Annis et al. |
| 2003/0114501 A1 | 6/2003 | Braun et al. |
| 2005/0250822 A1 | 11/2005 | Mita et al. |
| 2007/0066617 A1 | 3/2007 | Mita et al. |
| 2009/0023923 A1 | 1/2009 | Mizukoshi et al. |
| 2009/0133319 A1 | 5/2009 | Lahm et al. |
| 2009/0143410 A1 | 6/2009 | Patel |
| 2009/0156643 A1 | 6/2009 | Mita et al. |
| 2010/0137612 A1 | 6/2010 | Yaosaka et al. |
| 2010/0173948 A1 | 7/2010 | Lahm et al. |
| 2010/0179195 A1 | 7/2010 | Lahm et al. |
| 2010/0249424 A1 | 9/2010 | Annis et al. |
| 2010/0254959 A1 | 10/2010 | Lahm et al. |
| 2010/0254960 A1 | 10/2010 | Long et al. |
| 2011/0059988 A1 | 3/2011 | Heckeroth et al. |

FOREIGN PATENT DOCUMENTS

| | | |
|---|---|---|
| CA | 2621228 A1 | 3/2007 |
| CA | 2632694 A1 | 7/2007 |
| CA | 2684632 A1 | 12/2008 |
| CN | 1498213 A | 5/2004 |
| CN | 101346336 A | 1/2009 |
| EA | 924 | 6/2000 |
| EP | 74069 A1 | 3/1983 |
| EP | 216541 A1 | 4/1987 |
| EP | 217462 A1 | 4/1987 |
| EP | 1538138 A1 | 6/2005 |
| EP | 1731512 A1 | 12/2006 |
| EP | 1973888 A1 | 10/2008 |
| EP | 1975149 A1 | 10/2008 |
| EP | 2155701 A2 | 2/2010 |
| EP | 2172462 A1 | 4/2010 |
| GB | 2351081 A | 12/2000 |
| JP | 199859944 | 3/1998 |
| JP | 1999503114 | 3/1999 |
| JP | 2002522424 A | 7/2002 |
| JP | 2004529130 A | 9/2004 |
| JP | 2005272452 A | 10/2005 |
| JP | 2007016017 A | 1/2007 |
| JP | 2007106756 A | 4/2007 |
| JP | 2007308471 A | 11/2007 |
| JP | 2009203220 A | 9/2009 |
| KZ | 13246 | 7/2003 |
| KZ | 16356 | 10/2005 |
| RU | 99101948 | 10/2001 |
| RU | 2433123 C2 | 11/2011 |
| TW | 200738696 | 8/2007 |
| WO | 199854122 A1 | 12/1998 |
| WO | 2004099197 A2 | 11/2004 |
| WO | 2005085216 A1 | 9/2005 |
| WO | 2005094329 A2 | 10/2005 |
| WO | 2006135640 A2 | 12/2006 |
| WO | 2007026965 A1 | 3/2007 |
| WO | 20070700606 A2 | 6/2007 |
| WO | 2007074789 A1 | 7/2007 |
| WO | 2007075459 A2 | 7/2007 |
| WO | 2007079162 A1 | 7/2007 |
| WO | 2007105814 A | 9/2007 |
| WO | 2007105814 A1 | 9/2007 |
| WO | 2007123855 A2 | 11/2007 |
| WO | 2007125984 A1 | 11/2007 |
| WO | 2008019760 A1 | 2/2008 |
| WO | 2008108448 A1 | 9/2008 |
| WO | 2008122375 A2 | 10/2008 |
| WO | 2008154528 A2 | 12/2008 |
| WO | 2009001942 A1 | 12/2008 |
| WO | 2009002809 A2 | 12/2008 |
| WO | 2009003075 A1 | 12/2008 |
| WO | 2009025983 A2 | 2/2009 |
| WO | 2009035004 A1 | 3/2009 |
| WO | 2009045999 A1 | 4/2009 |
| WO | 2009126668 A2 | 10/2009 |
| WO | 2014000222 A1 | 1/2014 |

OTHER PUBLICATIONS

Office Action dated Sep. 21, 2011 in copending U.S. Appl. No. 13/156,653.

Office Action dated Sep. 21, 2011 received in counterpart U.S. Appl. No. 13/156,653.

Office Actions dated Nov. 23, 2012 in counterpart U.S. Appl. No. 13/561,546.

(56) References Cited

OTHER PUBLICATIONS

Parrilla et al., "Synthesis of trifluoromethyl ketones as inhibitors of antennal esterases of insects," Bioorganize & Medicinal Chemistry (1994) 2(4):243-252.
Ragaila et al., "Newer heterocycles and carbamates from naphthyl," Egyptian Journal of Pharmaceutical Sciences (1988) 29(1-4):71-87.
Sato et al., Science of Synthesis (2005) 18:821 [pp. IV and 924].
Sosnovskii et al., "Ketone-ketone condensation with participation of polyhaloalkyl phenyl ketones," Journal of Organic Chemistry of the USSR, (1992) 28:420-426.
Wang Zhaozhong et al., "Synthesis and application of a fluorine-containing agent, α,α,α-trifluoroacetophenone", Chemical Reagents, 1998, 20(4), 220-223.
[Kuznetsova et al., "Synthesis of fluorine-containing functionalized isoxazolines," Proceedings of the Academy of Sciences (1996) 5:1306-1307]. English Translation of Russian Office Action.
Advisory Action dated Sep. 6, 2012 received in copending U.S. Appl. No. 12/677,927.
Carey et al., "Advanced Organic Chemistry," 2ed., Part B: Reactions and Synthesis, (1983) Pelenum Press, New York.
Creary "Reaction of Organometallic Reagents with Ethyl Trifluoroacetate and Diethyl Oxalate. Formation of Trifluoromethyl Ketones and alpha-Keto Esters via Stable Tetrahedral Adducts," Journal of Organic Chemistry (1987) 52:5026-5030.
Database Chemical Abstracts Service (1988) XP002516318, Database accession No. 111:115084.
Database Chemical Abstracts Service (1996) XP002516333, Database Accession No. 126:31303.
Dighade et al,. "Effect of solvents in synthesis of new 4-(2-hydroxy-5-methylphenyl)-6-aryl-2-imino-6H-2,3-dihydro-1,3-thiazines,-" Asian Journal of Chemistry (2001) 13(4):1560-1564.
Final Office Action received in copending U.S. Appl. No. 12/602,821 dated Mar. 13, 2013.
Final Office Action received in copending U.S. Appl. No. 12/663,848 dated Jan. 28, 2013.
International Search Report dated Feb. 24, 2011 received in copending International Application No. PCT/US2009/039832.
Kamble et al., "An efficient synthesis of pharmacologically active derivatives 1,3,4-Oxadiazoles," Journal of Heterocyclic Chemistry (2006) 43(345):345-352.
Konno et al., "Palladium-Catalyzed Regio- and Stereoselective Formate Reduction of Fluorine-Containing Allylic Mesylates. A New Entry for the Construction of a Tertiary Carbon Attached with a Fluoroalkyl Group," Journal of Organic Chemistry (2006)71(9):3545-3550.
Kuznetsova et al., "Synthesis of fluorine-containing functionalized isoxazolines," Russian Chemical Bulletin (1996) (5):1245-1246.
Lahm et al (2007): STN International HCAPLUS database, Columbus (OH), accession No. 2007:755410, 2007.
Mita et al. (2007): STN International HCAPLUS database, (Columbus, Ohio), Accession No. 2007:330406.
Mita et al. (2007): STN International HCAPLUS database, (Columbus, Ohio), Accession No. 2009:740002.
Motoki et al., "Copper(I) alkoxide-catalyzed alkynylation of trifluoromethyl ketones," Organic Letters (2007) 9 (16):2997-3000.
Non-final Office Action dated Aug. 3, 2009 received in copending U.S. Appl. No. 12/083,944.
Non-Final Office Action dated Dec. 12, 2013 received in copending U.S. Appl. No. 14/047,500.
Non-final Office Action dated Dec. 16, 2009 received in copending U.S. Appl. No. 12/083,944.
Non-Final Office Action dated Jun. 13, 2014 received in copending U.S. Appl. No. 14/041,938.
Non-final Office Action dated May 19, 2010 received in copending U.S. Appl. No. 12/083,944.
Non-Final Office Action dated Nov. 23, 2012 received in copending U.S. Appl. No. 13/561,546.
Non-final Office Action dated Nov. 28, 2011 received in copending U.S. Appl. No. 12/663,751.
Notice of Allowance and Fee(s) due dated Mar. 18, 2012 received in copending U.S. Appl. No. 12/679,382.
Notice of Allowance and Fee(s) due dated Mar. 21, 2012 in copending U.S. Appl. No. 13/156,653.
Notice of Allowance dated Jun. 7, 2013 received in copending U.S. Appl. No. 13/561,546.
Notice of Allowance dated Apr. 15, 2013 received in copending U.S. Appl. No. 13/544,113.
Notice of Allowance dated Aug. 23, 2013 received in copending U.S. Appl. No. 12/602,821.
Notice of Allowance dated Feb. 6, 2012 received in copending U.S. Appl. No. 12/663,848.
Notice of Allowance dated Jan. 11, 2011 received in copending U.S. Appl. No. 12/086,935.
Notice of Allowance dated Jun. 24, 2014 received in copending U.S. Appl. No. 14/275,664.
Notice of Allowance dated Mar. 21, 2012 received in copending U.S. Appl. No. 13/156,653.
Notice of Allowance dated Nov. 14, 2012 in counterpart U.S. Appl. No. 12/663,751.
Notice of Allowance dated Nov. 20, 2014 received in co-pending U.S. Appl. No. 12/663,848.
Notice of Allowance dated Oct. 21, 2010 received in copending U.S. Appl. No. 12/083,944.
Notice of Allowance dated Sep. 24, 2012 received in copending U.S. Appl. No. 12/677,927.
Notice of Allowance dated Sep. 28, 2010 received in copending U.S. Appl. No. 12/086,935.
Notice of Allowance received in copending U.S. Appl. No. 12/933,493 dated May 14, 2013.
Notice of Allowance received in copending U.S. Appl. No. 13/544,113 dated Apr. 15, 2013.
Notice of Allowance received in copending U.S. Appl. No. 13/561,546 dated Jun. 7, 2013.
Notice of Allowance received in counterpart U.S. Appl. No. 12/663,751 dated Nov. 14, 2012.
Office Action dated Aug. 14, 2012 received in copending U.S. Appl. No. 12/933,493.
Office Action dated Aug. 27, 2014 received in copending U.S. Appl. No. 14/148,410.
Office Action dated Feb. 6, 2012 received in copending U.S. Appl. No. 12/602,821.
Office Action dated Jan. 23, 2012 received in copending U.S. Appl. No. 12/667,927.
Office Action dated Jul. 15, 2014 received in copending U.S. Appl. No. 13/037,257.
Office Action dated Jul. 2, 2012 received in copending U.S. Appl. No. 12/677,927.
Office Action dated Jun. 26, 2012 received in copending U.S. Appl. No. 12/602,821.
Office Action dated Jun. 8, 2012 received in copending U.S. Appl. No. 12/663,751.

METHOD FOR PREPARING 3-TRIFLUOROMETHYL CHALCONES

FIELD OF THE INVENTION

This invention pertains to a method for preparing 3-trifluoromethyl chalcones and trifluoroacetyl intermediates. The present invention also relates to novel trifluoroacetyl and halo compounds useful as starting materials and intermediates for the aforedescribed method.

SUMMARY OF THE INVENTION

The present invention provides a method for preparing a compound of Formula 1

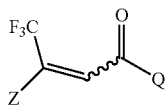
1 wherein
Z is optionally substituted phenyl; and
Q is phenyl or 1-naphthalenyl, each optionally substituted;
comprising distilling water from a mixture comprising a compound of Formula 2

2 a compound of Formula 3

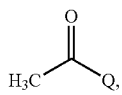
3 a base comprising at least one compound selected from the group consisting of
alkaline earth metal hydroxides of Formula 4

4 wherein M is Ca, Sr or Ba,
alkali metal carbonates of Formula 4a $(M^1)_2CO_3$  4a wherein $M^1$ is Li, Na or K,
1,5-diazabicyclo[4.3.0]non-5-ene and 1,8-diazabicyclo[5.4.0]undec-7-ene, and an aprotic solvent capable of forming a low-boiling azeotrope with water.

This invention also provides a method for preparing a compound of Formula 2 wherein Z is optionally substituted phenyl, comprising
(1) forming a reaction mixture comprising a Grignard reagent derived from a compound of Formula 5

Z—X  5 wherein X is Cl, Br or I,
by contacting the compound of Formula 5 with
(a) magnesium metal, or
(b) an alkylmagnesium halide
in the presence of an ethereal solvent; and then
(2) contacting the reaction mixture with a compound of Formula 6

6 wherein
Y is $OR^{11}$ or $NR^{12}R^{13}$;
$R^{11}$ is $C_1$-$C_5$ alkyl; and
$R^{12}$ and $R^{13}$ are independently $C_1$-$C_2$ alkyl; or $R^{12}$ and $R^{13}$ are taken together as —$CH_2CH_2OCH_2CH_2$—.

This invention also provides a method for preparing a compound of Formula 2 wherein Z is phenyl optionally substituted with up to S substituents independently selected from $R^2$; and each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio, comprising
(1) forming a reaction mixture comprising a Grignard reagent derived from a compound of Formula 5

Z—X  5 wherein X is I,
by contacting the compound of Formula 5 with
(a) magnesium metal, or
(b) an alkylmagnesium halide
in the presence of an ethereal solvent; and then
(2) contacting the reaction mixture with a compound of Formula 6

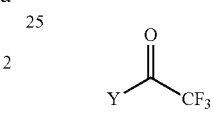
6 wherein
Y is $OR^{11}$ or $NR^{12}R^{13}$;
$R^{11}$ is $C_1$-$C_5$ alkyl; and
$R^{12}$ and $R^{13}$ are independently $C_1$-$C_2$ alkyl; or $R^{12}$ and $R^{13}$ are taken together as —$CH_2CH_2OCH_2CH_2H$—.

This invention also relates to the method disclosed above for preparing a compound of Formula 1 from a compound of Formula 2 and a compound of Formula 3 wherein the method is further characterized by preparing the compound of Formula 2 from the compounds of Formulae 5 and 6 by the method disclosed above.

The invention also relates to a method for preparing a compound of Formula 7

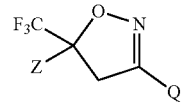
7 wherein
Z is optionally substituted phenyl; and
Q is phenyl or 1-naphthalenyl, each optionally substituted;
using a compound of Formula 1. The method is characterized by (a) preparing the compound of Formula 1 by the method disclosed above, or (b) using as said compound of Formula 1 a compound of Formula 1 prepared by the method disclosed above.

The present invention also relates to novel compounds of Formulae 2 and 5, useful as starting materials for the aforedescribed methods.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "alkylthio" or "haloalkyl" includes straight chain or branched alkyl, such as, methyl, ethyl, n-propyl, i-propyl, or the different butyl, pentyl or hexyl isomers.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)—$ and the different butylsulfinyl, pentylsulfinyl and hexylsulfinyl isomers. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Alkylamino", "dialkylamino" and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Similarly, "fluoroalkyl" means said alkyl may be partially or fully substituted with fluorine atoms. Examples of "haloalkyl" or "alkyl substituted with halogen" include $F_3C—$, $ClCH_2—$, $CF_3CH_2—$ and $CF_3CCl_2—$. The terms "halocycloalkyl", "haloalkoxy", "haloalkylthio", "haloalkylsulfinyl", "haloalkylsulfonyl", and the like, are defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkylthio" include $CCl_3S—$, $CF_3S—$, $CCl_3CH_2S—$ and $ClCH_2CH_2CH_2S—$. Examples of "haloalkylsulfinyl" include $CF_3S(O)—$, $CCl_3S(O)—$, $CF_3CH_2S(O)—$ and $CF_3CF_2S(O)—$. Examples of "haloalkylsulfonyl" include $CF_3S(O)_2—$, $CCl_3S(O)_2—$, $CF_3CH_2S(O)_2—$ and $CF_3CF_2S(O)_2—$. The term "halodialkylamino" denotes dialkylamino wherein at least one of the amino components is substituted with at least one halogen. Examples of "halodialkylamino" include $CH_2ClCH_2N(CH_3)—$ and $(CF_3CH_2)_2N—$.

"Alkylcarbonyl" denotes a straight-chain or branched alkyl moieties bonded to a $C(=O)$ moiety. Examples of "alkylcarbonyl" include $CH_3C(=O)—$, $CH_3CH_2CH_2C(=O)—$ and $(CH_3)_2CHC(=O)—$. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy or pentoxycarbonyl isomers.

In the present disclosure and claims, the radicals "$SO_2$" and "$S(O)_2$" mean sulfonyl, "—CN" means cyano, "—$NO_2$" means nitro, and "—OH" means hydroxy.

The total number of carbon atoms in a substituent group is indicated by the "$C_i$-$C_j$" prefix where i and j are numbers from 1 to 9. For example, $C_1$-$C_4$ alkylsulfonyl designates methylsulfonyl through butylsulfonyl, including possible isomers. $C_2$ alkoxycarbonyl designates $CH_3OC(O)—$; $C_3$ alkoxycarbonyl designates $CH_3CH_2C(O)—$; and $C_4$ alkoxycarbonyl includes $(CH_3)_2CHC(O)—$ and $CH_3CH_2CH_2C(O)—$.

When a compound is substituted with a substituent bearing a subscript that indicates the number of said substituents can exceed 1, said substituents (when they exceed 1) are independently selected from the group of defined substituents, e.g., for $(R^v)_r$ in U-1 of Exhibit 1, r is 1, 2, 3, 4 or 5. When a group contains a substituent which can be hydrogen (e.g., —$NR^4R^5$ in the definition of $R^3$ wherein $R^4$ or $R^5$ may be hydrogen in Embodiment 2), then when this substituent is taken as hydrogen, it is recognized that this is equivalent to said group being unsubstituted. When a variable group is shown to be optionally attached to a position, for example $(R^v)_r$ in U-41 of Exhibit 1 wherein r may be 0, then hydrogen may be at the position even if not recited in the variable group definition. When one or more positions on a group are said to be "not substituted" or "unsubstituted", then hydrogen atoms are attached to take up any free valency.

The terms "heterocyclic ring" or "heterocycle" denote a ring or ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. The term "ring member" refers to an atom or other moiety (e.g., $C(=O)$, $C(=S)$, $S(O)$ or $S(O)_2$) forming the backbone of a ring. Unless otherwise indicated, a heterocyclic ring can be a saturated, partially unsaturated or fully unsaturated ring, and furthermore, an unsaturated heterocyclic ring can be partially unsaturated or fully unsaturated. Therefore recitation of "heterocyclic ring" without indicating whether it is saturated or unsaturated is synonymous with recitation of "saturated or unsaturated heterocyclic ring". When a fully unsaturated heterocyclic ring satisfies Hückel's rule, then said ring is also called a "heteroaromatic ring" or "aromatic heterocyclic ring". "Aromatic" indicates that each of the ring atoms is essentially in the same plane and has a p-orbital perpendicular to the ring plane, and that (4n+2) π electrons, where n is a positive integer, are associated with the ring to comply with Hückel's rule. Unless otherwise indicated, heterocyclic rings and ring systems can be attached through any available carbon or nitrogen by replacement of a hydrogen on said carbon or nitrogen.

The term "optionally substituted" in connection with phenyl or 1-naphthalenyl in the definitions of Z and Q refers to groups which are unsubstituted or have at least one non-hydrogen substituent. As Z and Q are peripheral to the portions of the molecules undergoing reaction in the present methods, a very broad range of both number and type of substituents is compatible with the present methods. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $R^3$ or $Q^1$ is a 5- or 6-membered nitrogen-containing heterocyclic ring, it may be attached to the remainder of Formula 1 though any available carbon or nitrogen ring atom, unless otherwise described. As noted in Embodiment 1B, $R^3$ or $Q^1$ can be (among others) phenyl optionally substituted with one or more substituents selected from a group of substituents as defined in Embodiment 1B. An example of phenyl optionally substituted with one to five substituents is the ring illustrated as U-1 in Exhibit 1, wherein $R^v$ is as defined in Embodiment 1B for $R^3$ or $Q^1$ and r is an integer from 0 to 5.

As noted above, $R^3$ or $Q^1$ can be (among others) 5- or 6-membered heterocyclic ring, which may be saturated or unsaturated, optionally substituted with one or more substituents selected from a group of substituents as defined in Embodiment 2. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in Embodiment 2 for $R^3$ or $Q^1$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

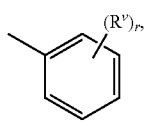

U-1

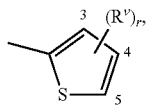

U-2

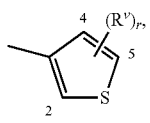

U-3

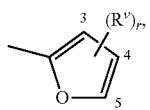

U-4

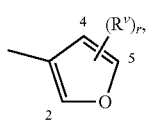

U-5

-continued

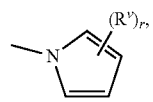

U-6

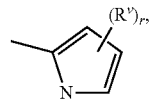

U-7

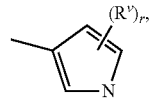

U-8

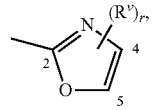

U-9

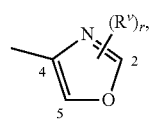

U-10

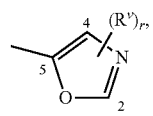

U-11

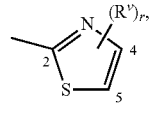

U-12

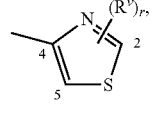

U-13

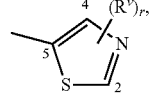

U-14

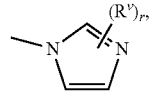

U-15

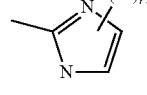

U-16

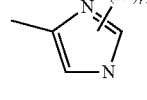

U-17

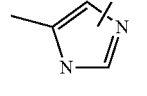

U-18

U-19 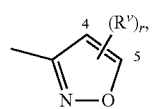
U-20 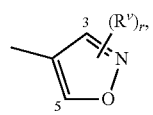
U-21 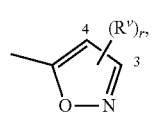
U-22 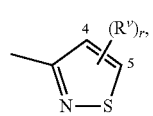
U-23 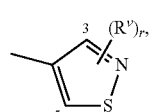
U-24 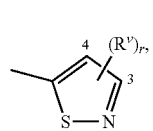
U-25 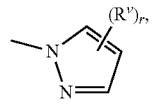
U-26 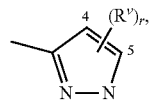
U-27 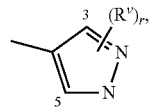
U-28 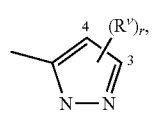
U-29 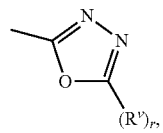
U-30 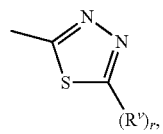
U-31 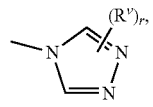
U-32 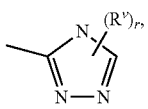
U-33 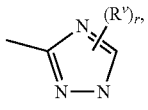
U-34 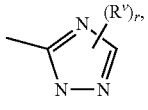
U-35 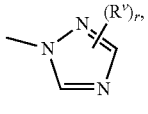
U-36 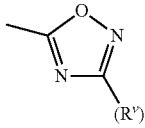
U-37 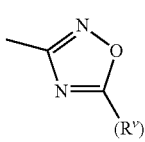
U-38 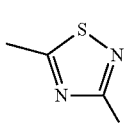
U-39 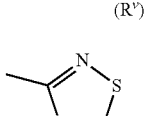
U-40 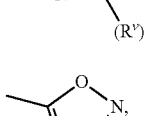
U-41 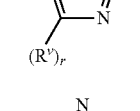
U-42 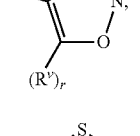
U-43 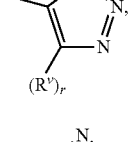
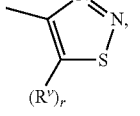

-continued

U-44 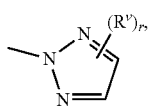

U-45 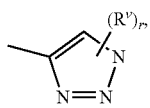

U-46 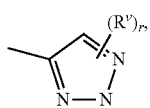

U-47 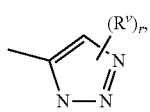

U-48 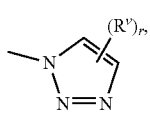

U-49 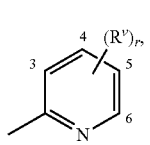

U-50 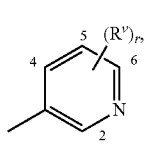

U-51 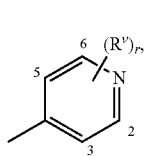

U-52 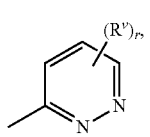

U-53 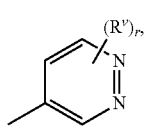

U-54 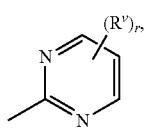

U-55 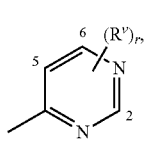

U-56 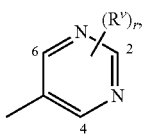

U-57 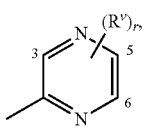

U-58 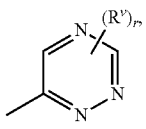

U-59 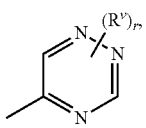

U-60 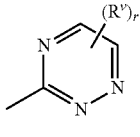

and

U-61 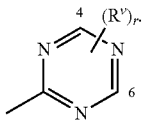

Note that when $R^3$ or $Q^1$ is a 5- or 6-membered saturated or unsaturated non-aromatic heterocyclic ring optionally substituted with one or more substituents selected from the group of substituents as defined in Embodiment 2 for $R^3$ or $Q^1$, one or two carbon ring members of the heterocycle can optionally be in the oxidized form of a carbonyl moiety.

Examples of a 5- or 6-membered saturated or non-aromatic unsaturated heterocyclic ring include the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when $R^3$ or $Q^1$ comprises a ring selected from G-28 through G-35, $G^2$ is selected from O, S or N. Note that when $G^2$ is N, the nitrogen atom can complete its valence by substitution with either H or the substituents corresponding to $R^v$ as defined in Embodiment 1B.

Exhibit 2

G-1 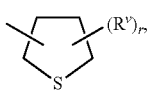

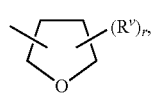 G-2
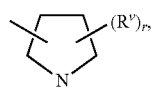 G-3
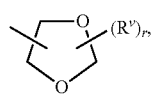 G-4
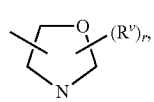 G-5
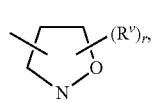 G-6
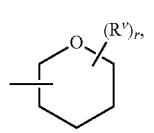 G-7
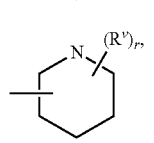 G-8
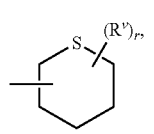 G-9
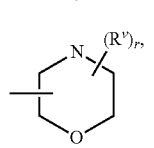 G-10
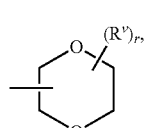 G-11
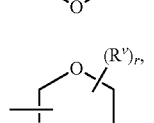 G-12
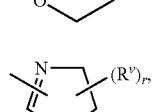 G-13
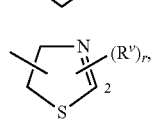 G-14
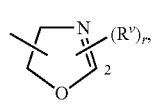 G-15
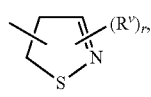 G-16
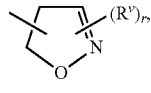 G-17
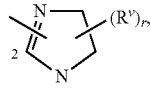 G-18
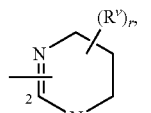 G-19
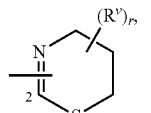 G-20
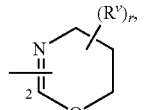 G-21
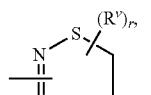 G-22
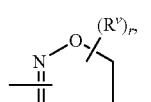 G-23
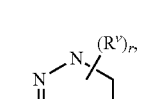 G-24
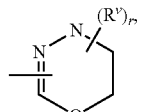 G-25
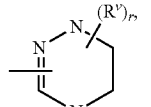 G-26
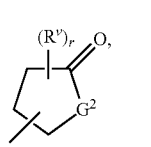 G-27
G-28

-continued

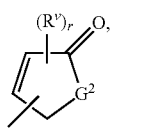
G-29

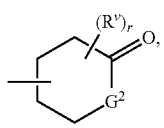
G-30

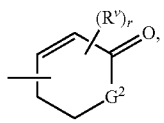
G-31

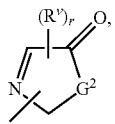
G-32

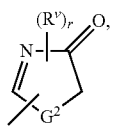
G-33

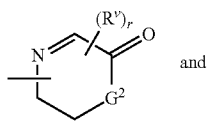
G-34 and

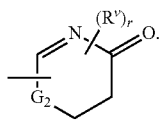
G-35

Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocylic Chemistry II*, A. R. Katritzky, C. W. Rees and E. F. V. Scriven editors-in-chief, Pergamon Press, Oxford, 1996.

In some instances herein ratios are recited as single numbers, which are relative to the number 1; for example, a ratio of 4 means 4:1.

In the context of the present invention, "decanter" refers to a device capable of separately removing an upper (i.e. less dense) liquid phase and/or a lower (i.e. more dense) liquid phase from a liquid (e.g., azeotrope condensate) comprising two liquid phases. A Dean-Stark trap is an example of one type of decanter.

Embodiments of the present invention include:

Embodiment 1

The method described in the Summary of the Invention for preparing the compound of Formula 1 comprising distilling water from the mixture comprising the compound of Formula 2, the compound of Formula 3, the base, and the aprotic solvent capable of forming a low-boiling azeotrope with water.

Embodiment 1A

The method of Embodiment 1 wherein the base is an alkaline earth metal hydroxide of Formula 4 and the mixture further comprises a polar aprotic solvent.

Embodiment 1B

The method of Embodiment 1 wherein the base comprises an alkali metal carbonate of Formula 4a.

Embodiment 1C

The method of Embodiment 1 wherein the base comprises 1,5-diazabicyclo[4.3.0]non-5-ene, 1,8-diazabicyclo[5.4.0]undec-7-ene or a mixture thereof.

Embodiment 1D

The method described in the Summary of the Invention for preparing a compound of Formula 7 using a compound of Formula 1, the method characterized by preparing the compound of Formula 1 by the method of Embodiment 1.

Embodiment 1E

The method described in the Summary of the Invention for preparing a compound of Formula 7 using a compound of Formula 1, the method characterized by preparing the compound of Formula 1 by the method of Embodiment 1A.

Embodiment 1F

The method described in the Summary of the Invention for preparing a compound of Formula 7 using a compound of Formula 1, the method characterized by preparing the compound of Formula 1 by the method of Embodiment 1B.

Embodiment 1G

The method described in the Summary of the Invention for preparing a compound of Formula 7 using a compound of Formula 1, the method characterized by preparing the compound of Formula 1 by the method of Embodiment 1C.

Embodiment 2

The method of any one of Embodiments 1 through 1G wherein
Q is phenyl or 1-naphthalenyl, each optionally substituted with up to four substituents independently selected from $R^3$;

each R³ is independently halogen, C₁-C₆ alkyl, C₁-C₆ haloalkyl, C₂-C₆ alkenyl, C₂-C₆ haloalkenyl, C₂-C₆ alkynyl, C₃-C₆ haloalkynyl, C₃-C₆ cycloalkyl, C₃-C₆ halocycloalkyl, C₁-C₆ alkoxy, C₁-C₆ haloalkoxy, C₁-C₆ alkylthio, C₂-C₇ alkylcarbonyl, C₂-C₇ haloalkylcarbonyl, C₁-C₆ haloalkylthio, C₁-C₆ alkylsulfinyl, C₁-C₆ haloalkylsulfinyl, C₁-C₆ alkylsulfonyl, C₁-C₆ haloalkylsulfonyl, —N(R⁴)R⁵, —C(=W)N(R⁴)R⁵, —C(=W)OR⁵, —CN, —OR¹¹ or —NO₂; or a phenyl ring or a 5- or 6-membered saturated or unsaturated heterocyclic ring, each ring optionally substituted with one or more substituents independently selected from halogen, C₁-C₆ alkyl, C₁-C₆ haloalkyl, C₃-C₆ cycloalkyl, C₃-C₆ halocycloalkyl, C₁-C₆ alkoxy, C₁-C₆ haloalkoxy, C₁-C₆ alkylthio, C₁-C₆ haloalkylthio, C₁-C₆ alkylsulfinyl, C₁-C₆ haloalkylsulfinyl, C₁-C₆ alkylsulfonyl, C₁-C₆ haloalkylsulfonyl, —CN, —NO₂, —N(R⁴)R⁵, —C(=W)N(R⁴)R⁵, —C(=O)OR⁵ and R⁷;

each R⁴ is independently H, C₁-C₆ alkyl, C₂-C₆ alkenyl, C₂-C₆ alkynyl, C₃-C₆ cycloalkyl, C₄-C₇ alkylcycloalkyl, C₄-C₇ cycloalkylalkyl, C₂-C₇ alkylcarbonyl or C₂-C₇ alkoxycarbonyl;

each R⁵ is independently H; or C₁-C₆ alkyl, C₂-C₆ alkenyl, C₂-C₆ alkynyl, C₃-C₆ cycloalkyl, C₄-C₇ alkylcycloalkyl or C₄-C₇ cycloalkylalkyl, each optionally substituted with one or more substituents independently selected from R⁶;

each R⁶ is independently halogen, C₁-C₆ alkyl, C₁-C₆ alkoxy, C₁-C₆ alkylthio, C₁-C₆ alkylsulfinyl, C₁-C₆ alkylsulfonyl, C₁-C₆ alkylamino, C₂-C₈ dialkylamino, C₃-C₆ cycloalkylamino, C₂-C₇ alkylcarbonyl, C₂-C₇ alkoxycarbonyl, C₂-C₇ alkylaminocarbonyl, C₃-C₉ dialkylaminocarbonyl, C₂-C₇ haloalkylcarbonyl, C₂-C₇ haloalkoxycarbonyl, C₂-C₇ haloalkylaminocarbonyl, C₃-C₉ halodialkylaminocarbonyl, —OH, —NH₂, —CN or —NO₂; or Q¹;

each R⁷ is independently a phenyl ring or a pyridinyl ring, each ring optionally substituted with one or more substituents independently selected from R⁸;

each R⁸ is independently halogen, C₁-C₆ alkyl, C₁-C₆ haloalkyl, C₁-C₆ alkoxy, C₁-C₆ haloalkoxy, C₁-C₆ alkylthio, C₁-C₆ haloalkylthio, C₁-C₆ alkylsulfinyl, C₁-C₆ haloalkylsulfinyl, C₁-C₆ alkylsulfonyl, C₁-C₆ haloalkylsulfonyl, C₁-C₆ alkylamino, C₂-C₆ dialkylamino, C₂-C₄ alkylcarbonyl, C₂-C₄ alkoxycarbonyl, C₂-C₇ alkylaminocarbonyl, C₃-C₇ dialkylaminocarbonyl, —OH, —NH₂, —C(=O)OH, —CN or —NO₂;

each Q¹ is independently a phenyl ring or a 5- or 6-membered saturated or unsaturated heterocyclic ring, each ring optionally substituted with one or more substituents independently selected from halogen, C₁-C₆ alkyl, C₁-C₆ haloalkyl, C₃-C₆ cycloalkyl, C₃-C₆ halocycloalkyl, C₁-C₆ alkoxy, C₁-C₆ haloalkoxy, C₁-C₆ alkylthio, C₁-C₆ haloalkylthio, C₁-C₆ alkylsulfinyl, C₁-C₆ haloalkylsulfinyl, C₁-C₆ alkylsulfonyl, C₁-C₆ haloalkylsulfonyl, C₁-C₆ alkylamino, C₂-C₆ dialkylamino, —CN, —NO₂, —C(=W)N(R⁹)R¹⁰ and —C(=O)OR¹⁰;

each R⁹ is independently H, C₁-C₆ alkyl, C₁-C₆ haloalkyl, C₂-C₆ alkenyl, C₂-C₆ alkynyl, C₃-C₆ cycloalkyl, C₄-C₇ alkylcycloalkyl, C₄-C₇ cycloalkylalkyl, C₂-C₇ alkylcarbonyl or C₂-C₇ alkoxycarbonyl;

each R¹⁰ is independently H; or C₁-C₆ alkyl, C₁-C₆ haloalkyl, C₂-C₆ alkenyl, C₂-C₆ alkynyl, C₃-C₆ cycloalkyl, C₄-C₇ alkylcycloalkyl or C₄-C₇ cycloalkylalkyl;

each R¹¹ is independently H; or C₂-C₆ alkenyl, C₂-C₆ alkynyl, C₃-C₆ cycloalkyl, C₄-C₇ alkylcycloalkyl, C₄-C₇ cycloalkylalkyl, C₂-C₇ alkylcarbonyl, C₂-C₇ alkoxycarbonyl, C₁-C₆ alkylsulfonyl or C₁-C₆ haloalkylsulfonyl; and each W is independently O or S.

Embodiment 2A

The method of Embodiment 2 wherein Q is phenyl optionally substituted with up to four substituents independently selected from R³.

Embodiment 2B

The method of Embodiment 2 wherein Q is 1-naphthalenyl optionally substituted with up to four substituents independently selected from R³.

Embodiment 2C

The method of Embodiment 2 wherein each R³ is independently halogen, C₁-C₆ alkyl, C₁-C₆ haloalkyl, —C(W)N(R⁴)R⁵, —C(W)OR⁵ or —CN; or a phenyl ring or a 5- or 6-membered saturated or unsaturated heterocyclic ring, each ring optionally substituted with substituents independently selected from halogen, C₁-C₆ alkyl, C₁-C₆ haloalkyl, —CN, —C(W)N(R⁴)R⁵ and —C(O)OR⁵.

Embodiment 2D

The method of Embodiment 2 wherein each R⁴ is independently H or C₁-C₆ alkyl.

Embodiment 2E

The method of Embodiment 2 wherein each R⁵ is independently H; or C₁-C₆ alkyl optionally substituted with substituents independently selected from R⁶.

Embodiment 2F

The method of Embodiment 2 wherein each R⁶ is independently halogen, C₁-C₆ alkyl, C₁-C₆ alkoxy, C₁-C₆ alkylthio, C₂-C₇ alkoxycarbonyl, C₂-C₇ alkylaminocarbonyl, C₃-C₉ dialkylaminocarbonyl, C₂-C₇-haloalkylaminocarbonyl, C₃-C₉ halodialkylaminocarbonyl or —CN; or Q¹.

Embodiment 2G

The method of Embodiment 2 wherein each Q¹ is independently a pyridinyl ring optionally substituted with up to four halogen.

Embodiment 2H

The method of Embodiment 2B wherein Q is

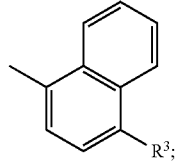

and
R³ is C(O)N(R⁴)R⁵ or C(O)OR⁵.

Embodiment 2I

The method of Embodiment 2H wherein
R⁴ is H, C₂-C₇ alkylcarbonyl or C₂-C₇ alkoxycarbonyl.

Embodiment 2J

The method of Embodiment 2I wherein $R^4$ is H.

Embodiment 2K

The method of any one of Embodiments 2H through 2J wherein
$R^3$ is $C(O)N(R^4)R^5$ or $C(O)OR^{5a}$;
$R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl; and
$R^5$ is $C_1$-$C_6$ alkyl, $C_2$-$C_6$ alkenyl or $C_2$-$C_6$ alkynyl, each optionally substituted with one or more substituents independently selected from halogen, $C_1$-$C_2$ alkoxy and phenyl optionally substituted with up to 5 substituents selected from halogen and $C_1$-$C_3$ alkyl.

Embodiment 2L

The method of any one of Embodiments 2H through 2K wherein
$R^{5a}$ is $C_1$-$C_6$ alkyl optionally substituted with phenyl.

Embodiment 2M

The method of any one of Embodiments 2H through 2L wherein
$R^3$ is $C(O)N(R^4)R^5$.

Embodiment 2N

The method of any one of Embodiments 2H through 2J wherein
$R^3$ is $C(O)OR^5$.

Embodiment 2O

The method of any one of Embodiments 2K through 2L wherein
$R^3$ is $C(O)OR^{5a}$.

Embodiment 3

The method of any one of Embodiments 1 through 2O wherein
Z is phenyl optionally substituted with up to 5 substituents independently selected from $R^2$ (i.e.

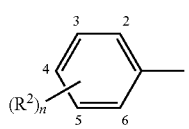

wherein n is 0, 1, 2, 3, 4 or 5); and
each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.

Embodiment 3A

The method of Embodiment 3 wherein Z is a phenyl ring substituted with up to 3 substituents independently selected from $R^2$, said substituents attached at the 3, 4 or 5 positions of the phenyl ring.

Embodiment 3B

The method of Embodiment 3 or 3A wherein each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio.

Embodiment 3C

The method of Embodiment 3 or 3A wherein each $R^2$ is independently halogen, $C_1$-$C_6$ alkyl, $C_1$-$C_6$ haloalkyl or —CN.

Embodiment 3D

The method of Embodiment 3C wherein each $R^2$ is independently halogen or $C_1$-$C_6$ haloalkyl.

Embodiment 3E

The method of Embodiment 3D wherein each $R^2$ is independently halogen or $CF_3$.

Embodiment 3F

The method of Embodiment 3E wherein each $R^2$ is independently F, Cl or $CF_3$.

Embodiment 3G

The method of Embodiment 3A wherein Z is

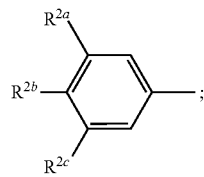

$R^{2a}$ is halogen, $C_1$-$C_2$ haloalkyl or $C_1$-$C_2$ haloalkoxy; $R^{2b}$ is H, halogen or cyano; and $R^{2c}$ is H, halogen or $CF_3$.

Embodiment 3H

The method of Embodiment 3G wherein $R^{2a}$ is $CF_3$ or halogen; and
$R^{2c}$ is H, $CF_3$ or halogen.

Embodiment 3I

The method of Embodiment 3H wherein $R^{2a}$ is $CF_3$.

Embodiment 3J

The method of any one of Embodiments 3G through 3I wherein $R^{2b}$ is H.

Embodiment 3K

The method of any one of Embodiments 3G through 3J wherein $R^{2c}$ is $CF_3$ or halogen.

Embodiment 3L

The method of Embodiment 3K wherein $R^{2c}$ is $CF_3$, F, Cl or Br.

Embodiment 3M

The method of Embodiment 3L wherein $R^{2c}$ is F, Cl or Br.

Embodiment 3N

The method of Embodiment 3L wherein $R^{2c}$ is $CF_3$, Cl or Br.

Embodiment 3O

The method of Embodiment 3N wherein $R^{2c}$ is Cl or Br.

Embodiment 3P

The method of Embodiment 3O wherein $R^{2b}$ is H and $R^{2c}$ is Cl.

Embodiment 3Q

The method of Embodiment 3O wherein $R^{2b}$ is H and $R^{2c}$ is Br.

Embodiment 4

The method described in the Summary of the Invention for preparing a compound of Formula 2, comprising (1) forming a reaction mixture comprising a Grignard reagent derived from a compound of Formula 5 by contacting the compound of Formula 5 with (a) magnesium metal, or (b) an alkylmagnesium halide in the presence of an ethereal solvent; and then (2) contacting the reaction mixture with a compound of Formula 6.

Embodiment 4A

The method of any one of Embodiments 1 through 2O and 3 through 3Q further characterized by preparing the compound of Formula 2 by the method of Embodiment 4.

Embodiment 4B

The method of Embodiment 4 or 4A wherein X is Cl or I.

Embodiment 4C

The method of Embodiment 4 or 4A wherein X is Br or I.

Embodiment 4D

The method of Embodiment 4 or 4A wherein X is Cl or Br.

Embodiment 4E

The method of Embodiment 4 or 4A wherein X is Cl.

Embodiment 4F

The method of Embodiment 4 or 4A wherein X is Br.

Embodiment 4G

The method of Embodiment 4 or 4A wherein X is I.

Embodiment 4H

The method of any one of Embodiments 4 through 4G wherein
Z is phenyl optionally substituted with up to 5 substituents independently selected from $R^2$ (i.e.

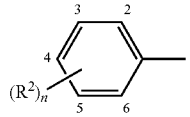

wherein n is 0, 1, 2, 3, 4 or 5); and
each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio; provided that when X is Cl then each $R^2$ is independently F, Cl, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio.

Embodiment 4I

The method of Embodiment 4H wherein when X is Br then each $R^2$ is independently F, Cl, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio; and when X is Cl then each $R^2$ is independently F, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio.

Embodiment 4J

The method of any one of Embodiments 3, 4H and 4I wherein Z is a phenyl ring substituted with up to 3 substituents independently selected from $R^2$, said substituents attached at the 3, 4 or 5 positions of the phenyl ring.

Embodiment 4K

The method of any one of Embodiments 4H, 4I and 4J wherein each $R^2$ is independently F, Cl, Br, $C_1$-$C_6$ alkyl or $C_1$-$C_6$ fluoroalkyl.

Embodiment 4L

The method of Embodiment 4K wherein each $R^2$ is independently F, Cl, Br or $C_1$-$C_6$ fluoroalkyl.

Embodiment 4M

The method of Embodiment 4L wherein each $R^2$ is independently F, Cl, Br or $CF_3$.

Embodiment 4N

The method of any one of Embodiments 4H through 4M wherein Z is a phenyl ring substituted with 2 substituents independently selected from $R^2$, said substituents attached at the 3 and 5 positions of the phenyl ring.

Embodiment 4O

The method of Embodiment 4N wherein each $R^2$ is independently F, Cl, Br or $CF_3$.

Embodiment 4P

The method of Embodiment 4O wherein at least one $R^2$ is $CF_3$.

Embodiment 4Q

The method of Embodiment 4P wherein one $R^2$ is $CF_3$ and the other $R^2$ is Cl or Br.

Embodiment 4R

The method of Embodiment 4Q wherein one $R^2$ is $CF_3$ and the other $R^2$ is Cl.

Embodiment 4S

The method of Embodiment 3A or 3H wherein Z is

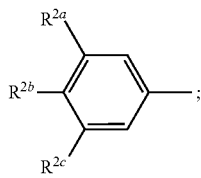

$R^{2a}$ is F, Cl, Br, $C_1$-$C_2$ fluoroalkyl or $C_1$-$C_2$ fluoroalkoxy; $R^{2b}$ is H, F, Cl or Br; and $R^{2c}$ is H, F, Cl, Br or $CF_3$.

Embodiment 4T

The method of Embodiment 4S wherein $R^{2a}$ is $CF_3$, F, Cl or Br; and $R^{2c}$ is H, $CF_3$, F, Cl or Br.

Embodiment 4U

The method of Embodiment 4T wherein $R^{2a}$ is $CF_3$.

Embodiment 4V

The method of any one of Embodiments 4S through 4U wherein $R^{2b}$ is H.

Embodiment 4W

The method of any one of Embodiments 4S through 4V wherein $R^{2c}$ is $CF_3$, F, Cl or Br.

Embodiment 4X

The method of Embodiment 4W wherein $R^{2c}$ is F, Cl or Br.

Embodiment 4Y

The method of Embodiment 4W wherein $R^{2c}$ is $CF_3$, Cl or Br.

Embodiment 4Z

The method of Embodiment 4Y wherein $R^{2c}$ is Cl or Br.

Embodiment 4ZA

The method of Embodiment 4Z wherein $R^{2b}$ is H and $R^{2c}$ is Cl.

Embodiment 4ZB

The method of Embodiment 4Z wherein $R^{2b}$ is H and $R^{2c}$ is Br.

Embodiment 4ZC

The method of any one of Embodiments 4S through 4ZB wherein X is I.

Embodiment 5

A compound of Formula 2 as described in the Summary of the Invention wherein
Z is

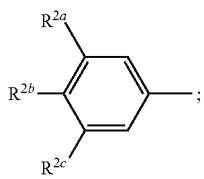

$R^{2a}$ is $CF_3$; $R^{2b}$ is H or halogen; and $R^{2c}$ is halogen.

Embodiment 5A

A compound of Embodiment 5 wherein $R^{2b}$ is H.

Embodiment 5B

A compound of Embodiment 5 or 5A wherein $R^{2c}$ is F, Cl or Br.

Embodiment 5C

A compound of Embodiment 5B wherein $R^{2c}$ is Cl or Br.

Embodiment 5D

A compound of Embodiment 5C selected from the group consisting of:
1-[3-chloro-5-(trifluoromethyl)]-2,2,2-trifluoroethanone; and
1-[3-bromo-5-(trifluormethyl)]-2,2,2-trifluoroethanone.

Embodiment 5E

A compound of Formula 5 as described in the Summary of the Invention which is 1-chloro-3-iodo-5-(trifluormethyl)benzene.

Embodiment 6

The method of Embodiment 1A or 1E wherein M is Ca (i.e. the alkaline earth metal hydroxide is calcium hydroxide).

Embodiment 6A

The method of Embodiment 1A, 1E or 6 wherein the molar ratio of the alkaline earth metal hydroxide to the compound of Formula 2 is at least about 0.1.

Embodiment 6A1

The method of Embodiment 6A wherein the molar ratio of the alkaline earth metal hydroxide to the compound of Formula 2 is at least about 0.5.

Embodiment 6B

The method of Embodiment 6A1 wherein the molar ratio of the alkaline earth metal hydroxide to the compound of Formula 2 is at least about 0.8.

Embodiment 6C

The method of any one of Embodiments 1A, 1E or 6 through 61 wherein the molar ratio of the alkaline earth metal hydroxide to the compound of Formula 2 is no more than about 1.

Embodiment 6D

The method of Embodiment 1B or 1F wherein $M^1$ is K (i.e. the alkali metal carbonate is potassium carbonate).

Embodiment 6E

The method of Embodiment 1B, 1F or 6D wherein the molar ratio of the alkali metal carbonate to the compound of Formula 2 is at least about 0.01.

Embodiment 6F

The method of Embodiment 6E wherein the molar ratio of the alkali metal carbonate to the compound of Formula 2 is at least about 0.03.

Embodiment 6G

The method of any one of Embodiments 1B, 1F or 6D through 6F wherein the molar ratio of the alkali metal carbonate to the compound of Formula 2 is no more than about 0.2.

Embodiment 6H

The method of Embodiment 1C or 1G wherein the molar ratio of the 1,5-diazabicyclo[4.3.0]non-5-ene, 1,8-diazabicyclo[5.4.0]undec-7-ene or a mixture thereof to the compound of Formula 2 is at least about 0.01.

Embodiment 6I

The method of Embodiment 6H wherein the molar ratio of the 1,5-diazabicyclo[4.3.0]non-5-ene, 1,8-diazabicyclo[5.4.0]undec-7-ene or a mixture thereof to the compound of Formula 2 is at least about 0.03.

Embodiment 6J

The method of any one of Embodiments 1C, 10, 6H or 6I wherein the molar ratio of the 1,5-diazabicyclo[4.3.0]non-5-ene, 1,8-diazabicyclo-[5.4.0]undec-7-ene or a mixture thereof to the compound of Formula 2 is no more than about 0.2.

Embodiment 7

The method of Embodiment 1A or 1E wherein the polar aprotic solvent comprises an amide or sulfoxide (including mixtures thereof).

Embodiment 7A

The method of Embodiment 7 wherein the polar aprotic solvent comprises one or more of N,N-dimethylformamide, N,N-dimethylacetamide, N-methylpyrrolidinone and methyl sulfoxide.

Embodiment 7B

The method of Embodiment 7 wherein the polar aprotic solvent comprises an amide.

Embodiment 7C

The method of Embodiment 7B wherein the polar aprotic solvent comprises one or more of N,N-dimethylformamide, N,N-dimethylacetamide, N-methylpyrrolidinone.

Embodiment 7D

The method of Embodiment 7C wherein the polar aprotic solvent comprises N,N-dimethylformamide.

Embodiment 8

The method of Embodiment 1A or 1E wherein the aprotic solvent capable of forming a low-boiling azeotrope with water comprises an ether.

Embodiment 8A

The method of Embodiment 8 wherein the aprotic solvent capable of forming a low-boiling azeotrope with water comprises tert-butyl methyl ether.

Embodiment 8B

The method of any one of Embodiments 1B, 1C, 1F, 1G or 6D through 6J wherein the aprotic solvent capable of forming a low-boiling azeotrope with water comprises acetonitrile.

Embodiment 8C

The method of Embodiment 8A wherein the polar aprotic solvent comprises N,N-dimethyl formamide.

Embodiment 8D

The method of Embodiment 8C wherein the tert-butyl methyl ether and the N,N-dimethylformamide are in a weight ratio in a range from about 0.5 to about 2.

Embodiment 9

The method of Embodiment 1A or 1E wherein the mixture is at a temperature of at least about 65° C.

Embodiment 9A

The method of Embodiment 9 wherein the mixture is at a temperature of at least about 70° C.

Embodiment 9B

The method of Embodiment 9A wherein the mixture is at a temperature of at least about 75° C.

Embodiment 9C

The method of Embodiment 1B, 1C, 1F or 10 wherein the mixture is at a temperature of at least about 65° C.

Embodiment 9D

The method of Embodiment 9C wherein the mixture is at a temperature of at least about 80° C.

Embodiment 9E

The method of Embodiment 9D wherein the mixture is at a temperature of at least about 85° C.

Embodiment 9F

The method of any one of Embodiments 9 through 9E wherein the mixture is at a temperature of no more than about 110° C.

Embodiment 9O

The method of Embodiment 9F wherein the mixture is at a temperature of no more than about 100° C.

Embodiment 9H

The method of Embodiment 9G wherein the mixture is at a temperature of no more than about 90° C.

Embodiment 10

The method of Embodiment 4 or 4A wherein the compound of Formula 5 is contacted with magnesium metal.

Embodiment 10A

The method of Embodiment 10 wherein the molar ratio of magnesium metal to the compound of Formula 5 is at least about 1.

Embodiment 10B

The method of Embodiment 10A wherein the molar ratio of magnesium metal to the compound of Formula 5 is at least about 1.02.

Embodiment 10C

The method of Embodiment 10B wherein the molar ratio of magnesium metal to the compound of Formula 5 is at least about 1.05.

Embodiment 10D

The method of any one of Embodiments 10 through 10C wherein the molar ratio of magnesium metal to the compound of Formula 5 is no more than about 1.2.

Embodiment 10E

The method of Embodiment 10D wherein the molar ratio of magnesium metal to the compound of Formula 5 is no more than about 1.1.

Embodiment 10F

The method of Embodiment 4 or 4A wherein the compound of Formula 5 is contacted with an alkylmagnesium halide.

Embodiment 10G

The method of Embodiment 10F wherein the alkylmagnesium halide is a $C_1$-$C_4$ alkylmagnesium halide.

Embodiment 10H

The method of Embodiment 10F or 10G wherein the alkylmagnesium halide is a secondary alkylmagnesium halide.

Embodiment 10I

The method of Embodiment 10H wherein the alkylmagnesium halide is an isopropylmagnesium halide.

Embodiment 10J

The method of Embodiment 10I wherein the alkylmagnesium halide is isopropylmagnesium chloride.

Embodiment 10K

The method of any one of Embodiments 10F through 10J wherein the molar ratio of the alkylmagnesium halide to the compound of Formula 5 is at least about 1.

Embodiment 10L

The method of Embodiment 10K wherein the molar ratio of the alkylmagnesium halide to the compound of Formula 5 is at least about 1.05.

Embodiment 10M

The method of any one of Embodiments 10F through 10L wherein the molar ratio of the alkylmagnesium halide to the compound of Formula 5 is no more than about 1.2.

Embodiment 10N

The method of Embodiment 10M wherein the molar ratio of the alkylmagnesium halide to the compound of Formula 5 is no more than about 1.15.

Embodiment 10O

The method of Embodiment 4 or 4A wherein the compound of Formula 6 is methyl trifluoroacetate or ethyl trifluoroacetate.

Embodiment 11

The method of Embodiment 4 or 4A wherein the ethereal solvent comprises one or more of ethyl ether, 1,4-dioxane, tetrahydrofuran and 1,2-dimethoxyethane.

Embodiment 11A

The method of Embodiment 11 wherein the ethereal solvent comprises ethyl ether or tetrahydrofuran.

Embodiment 11B

The method of Embodiment 11A wherein the ethereal solvent comprises tetrahydrofuran.

Embodiment 11C

The method of any one of Embodiments 4, 4A or 11 through 11B wherein the compound of Formula 5 is contacted with (a) magnesium metal, or (b) an alkylmagnesium halide in the presence of an aromatic hydrocarbon solvent in addition to the ethereal solvent.

Embodiment 11D

The method of Embodiment 11C wherein the aromatic hydrocarbon solvent comprises one or more of benzene, toluene and xylene.

Embodiment 11E

The method of Embodiment 11D wherein the aromatic hydrocarbon solvent comprises toluene.

Embodiments of this invention, including Embodiments 1-11E above as well as any other embodiments described herein, can be combined in any manner, and the descriptions of variables in the embodiments pertain not only to the aforedescribed methods for preparing compounds of Formulae 1, 2 and 7 but also to the starting compounds and intermediate compounds useful for preparing the compounds of Formulae 1, 2 and 7 by these methods.

Combinations of Embodiments 1-11E are illustrated by:

Embodiment A

The method described in the Summary of the Invention for preparing the compound of Formula 1 comprising distilling water from the mixture comprising the compound of Formula 2, the compound of Formula 3, the base, and the aprotic solvent capable of forming a low-boiling azeotrope with water, wherein Z is phenyl optionally substituted with up to 5 substituents independently selected from $R^2$;

Q is phenyl or 1-naphthalenyl, each optionally substituted with up to four substituents independently selected from $R^3$;

each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$;

each $R^3$ is independently halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_2$-$C_7$ alkylcarbonyl, $C_2$-$C_7$ haloalkylcarbonyl, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(=W)N($R^4$)$R^5$, —C(=W)$OR^5$, —CN, —$OR^{11}$ or —$NO_2$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —N($R^4$)$R^5$, —C(=W)N($R^4$)$R^5$, —C(=O)$OR^5$ and $R^7$;

each $R^4$ is independently H, $C_1$-$C_6$ alkyl, $C_2$-$C_6$ alkenyl, $C_2$-$C_6$ alkynyl, $C_1$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_6$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ halodialkylaminocarbonyl, —OH, —$NH_2$, —CN or —$NO_2$; or $Q^1$;

each $R^7$ is independently a phenyl ring or a pyridinyl ring, each ring optionally substituted with one or more substituents independently selected from $R^8$;

each $R^8$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —C(=O)OH, —CN or —$NO_2$;

each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, —C(=W)N($R^9$)$R^{10}$ and —C(=O)$OR^{10}$;

each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;

each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, ($C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and each W is independently O or S.

Embodiment A1

The method of Embodiment A wherein the base is an alkaline earth metal hydroxide of Formula 4 and the mixture further comprises a polar aprotic solvent.

Embodiment A2

The method of Embodiment A or A1 wherein Q is phenyl optionally substituted with up to four substituents independently selected from $R^3$.

Embodiment A3

The method of Embodiment A or A1 wherein Q is 1-naphthalenyl optionally substituted with up to four substituents independently selected from $R^3$.

Embodiment A4

The method of Embodiment A, A1 or A2 wherein
each $R^2$ is independently halogen or $C_1$-$C_6$ haloalkyl;
each $R^3$ is independently halogen, $C_1$-$C_6$ alkyl, $C_1$-$C_6$ haloalkyl, —C(W)N($R^4$)$R^5$, —C(W)O$R^5$ or —CN; or a phenyl ring or a 5- or 6-membered heterocyclic ring, each ring optionally substituted with one or more substituents independently selected from halogen, $C_1$-$C_6$ alkyl, $C_1$-$C_6$ haloalkyl, —CN, —C(W)N($R^4$)$R^5$ and —C(O)O$R^5$;
each $R^4$ is independently H or $C_1$-$C_6$ alkyl;
each $R^5$ is independently H; or $C_1$-$C_6$ alkyl optionally substituted with one or more substituents independently selected from $R^6$;
each $R^6$ is independently halogen, $C_1$-$C_6$ alkyl, $C_1$-$C_6$ alkoxy, $C_1$-$C_6$ alkylthio, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl or —CN; or $Q^1$; and
each $Q^1$ is independently a pyridinyl ring optionally substituted with up to 4 halogen.

Embodiment A5

The method of Embodiment A3 wherein
Z is

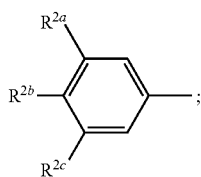

Q is

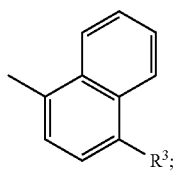

$R^{2a}$ is halogen, $C_1$-$C_2$ haloalkyl or $C_1$-$C_2$ haloalkoxy;
$R^{2b}$ is H, halogen or cyano;
$R^{2c}$ is H, halogen or $CF_3$;
$R^3$ is C(O)N($R^4$)$R^5$ or C(O)O$R^{5a}$;
$R^4$ is H, $C_2$-$C_7$ alkylcarbonyl or $C_2$-$C_7$ alkoxycarbonyl; and
$R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl; and
$R^{5a}$ is $C_1$-$C_6$ alkyl, $C_1$-$C_6$ alkenyl or $C_2$-$C_6$ alkynyl, each optionally substituted with one or more substituents independently selected from halogen, $C_1$-$C_2$ alkoxy and phenyl optionally substituted with up to 5 substituents selected from halogen and $C_1$-$C_3$ alkyl.

Embodiment A6

The method of Embodiment A5 wherein $R^3$ is C(O)N($R^4$)$R^5$.

Embodiment A7

The method of Embodiment A5 wherein $R^3$ is C(O)O$R^{5a}$.

Embodiment B

The method described in the Summary of the Invention for preparing the compound of Formula 1 comprising distilling water from the mixture comprising the compound of Formula 2, the compound of Formula 3, the base, and the aprotic solvent capable of forming a low-boiling azeotrope with water, wherein
Z is phenyl optionally substituted with up to 5 substituents independently selected from $R^2$ (i.e.

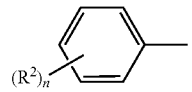

wherein n is 0, 1, 2, 3, 4 or 5); and
each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio; further comprising preparing the compound of Formula 2 by
(1) forming a reaction mixture comprising a Grignard reagent derived from a compound of Formula 5

     5 wherein X is Cl, Br or I,
by contacting the compound of Formula 5 with
(a) magnesium metal, or
(b) an alkylmagnesium halide
in the presence of an ethereal solvent; and then
(2) contacting the reaction mixture with a compound of Formula 6

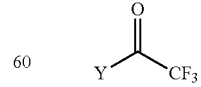     6 wherein
Y is O$R^{11}$ or N$R^{12}R^{13}$;
$R^{11}$ is $C_1$-$C_5$ alkyl; and
$R^{12}$ and $R^{13}$ are independently $C_1$-$C_2$ alkyl; or $R^{12}$ and $R^{13}$ are taken together as —$CH_2CH_2OCH_2CH_2$—.

Embodiment B1

The method of Embodiment B wherein the base is an alkaline earth metal hydroxide of Formula 4 and the mixture further comprises a polar aprotic solvent.

Embodiment B2

The method of Embodiment B or B1 wherein Z is

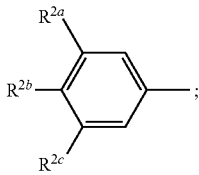

$R^{2a}$ is F, Cl, Br, $C_1$-$C_2$ fluoroalkyl or $C_1$-$C_2$ fluoroalkoxy;
$R^{2b}$ is H, F, Cl or Br; and
$R^{2c}$ is H. F, Cl, Br or $CF_3$.

Embodiment C

The method described in the Summary of the Invention for preparing a compound of Formula 2, comprising (1) forming a reaction mixture comprising a Grignard reagent derived from a compound of Formula 5 by contacting the compound of Formula 5 with (a) magnesium metal, or (b) an alkylmagnesium halide in the presence of an ethereal solvent; and then (2) contacting the reaction mixture with a compound of Formula 6, wherein X is I;
Z is phenyl optionally substituted with up to 5 substituents independently selected from $R^2$ (i.e.

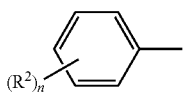

wherein n is 0, 1, 2, 3, 4 or 5); and
each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio.

Embodiment C1

The method of Embodiment C wherein Z is

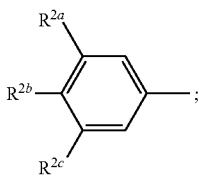

$R^{2a}$ is F, Cl, Br, $C_1$-$C_2$ fluoroalkyl or $C_1$-$C_2$ fluoroalkoxy;
$R^{2b}$ is H, F, Cl or Br; and
$R^{2c}$ is H, F, C, Br or $CF_3$.

Embodiment D

A method for preparing a compound of Formula 7

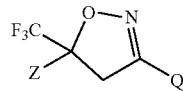

wherein
Z is optionally substituted phenyl; and
Q is phenyl or 1-naphthalenyl, each optionally substituted;
using a compound of Formula 1

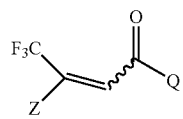

characterized by: preparing said compound of Formula 1 by the method described in the Summary of the Invention for preparing the compound of Formula 1 comprising distilling water from the mixture comprising the compound of Formula 2, the compound of Formula 3, the base, and the aprotic solvent capable of forming a low-boiling azeotrope with water.

Embodiment D1

The method of Embodiment D wherein the base is an alkaline earth metal hydroxide of Formula 4 and the mixture further comprises a polar aprotic solvent.

Embodiment D2

The method of Embodiment D or D1 wherein
Z is

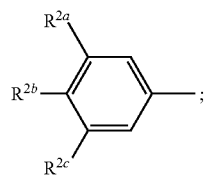

Q is

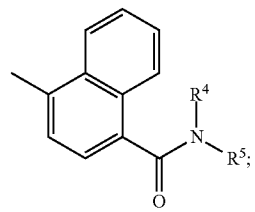

$R^{2a}$ is halogen, $C_1$-$C_2$ haloalkyl or $C_1$-$C_2$ haloalkoxy;
$R^{2b}$ is H, halogen or cyano;
$R^{2c}$ is H, halogen or $CF_3$;
$R^4$ is H, $C_2$-$C_7$ alkylcarbonyl or $C_2$-$C_7$ alkoxycarbonyl; and $R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl.

Embodiment E

A method for preparing a compound of Formula 7

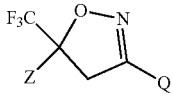

7 wherein
Z is optionally substituted phenyl; and
Q is phenyl or 1-naphthalenyl, each optionally substituted;
using a compound of Formula 1

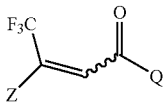

1 characterized by: using as said compound of Formula 1 a compound of Formula 1 prepared by the method described in the Summary of the Invention for preparing the compound of Formula 1 comprising distilling water from the mixture comprising the compound of Formula 2, the compound of Formula 3, the base, and the aprotic solvent capable of forming a low-boiling azeotrope with water.

Embodiment E1

The method of Embodiment E wherein the base is an alkaline earth metal hydroxide of Formula 4 and the mixture further comprises a polar aprotic solvent.

Embodiment E2

The method of Embodiment E or E1 wherein
Z is

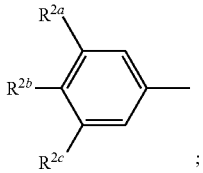

;

Q is

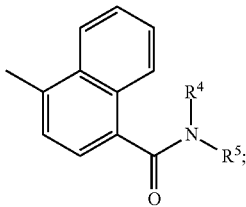

$R^{2a}$ is halogen, $C_1$-$C_2$ haloalkyl or $C_1$-$C_2$ haloalkoxy;
$R^{2b}$ is H, halogen or cyano;
$R^{2c}$ is H, halogen or $CF_3$;
$R^4$ is H, $C_2$-$C_7$ alkylcarbonyl or $C_2$-$C_7$ alkoxycarbonyl; and $R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl.

In the following Schemes 1-10 the definitions of Z, Q, $R^2$, $R^3$, $R^4$, $R^5$, $R^6$, $R^7$, $R^8$, $R^9$, $R^{10}$, $R^{11}$, $R^{12}$, $R^{13}$ and W in the compounds of Formulae 1 through 7 and 11 through 15 are as defined above in the Summary of the Invention and description of Embodiments unless otherwise indicated. Formula 1a is a subset of Formula 1. Formula 5a is a subset of Formula 5. Formulae 7a, 7b, 7c, 7d, 7e and 7f are subsets of Formula 7. Formula 13a is a subset of Formula 13.

In the method of the invention illustrated in Scheme 1, a compound of Formula 1 is prepared by distilling water from a mixture comprising a compound of Formula 2, a compound of Formula 3, an alkaline earth metal hydroxide base of Formula 4, a polar aprotic solvent, and an aprotic solvent capable of forming a low-boiling azeotrope with water.

Scheme 1

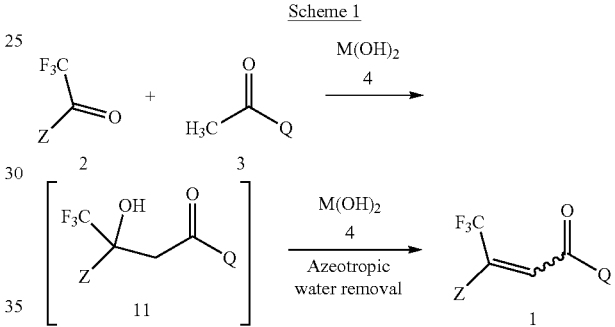

wherein M is Ca, Sr or Ba.

The first step of this reaction involves an aldol condensation to form a compound of Formula 11. The compound of Formula 11 is not isolated, but instead under the reaction conditions is converted to the compound of Formula 1.

The stoichiometry of this reaction involves equimolar amounts of the compounds of Formula 2 and Formula 3, and using equimolar amounts typically is most cost-effective. However, small molar excesses of one of the reactants are not deleterious to the reaction, and if one of the reactants is much less expensive or more preparatively accessible, using it in a slight excess (e.g., 1.05 molar equivalents) may be desirable to ensure complete conversion of the more expensive or less preparatively accessible reactant.

Alkaline earth metal hydroxides of Formula 4 and compounds capable of forming said alkaline earth metal hydroxides on contact with water have been discovered to be particularly efficacious in providing high yields of compounds of Formula 1. These alkaline earth metal hydroxide bases include calcium, strontium or barium hydroxides, with calcium hydroxide preferred for its low cost. The alkaline earth metal hydroxides of Formula 4 can be formed in situ from compounds capable of forming alkaline earth metal hydroxides on contact with water (identified herein as "alkaline earth metal hydroxide precursors") such as alkaline earth metal hydrides. Alkaline earth metal hydroxide precursors can react with water present in the reaction mixture, including water formed by the reaction, to form the corresponding alkaline earth metal hydroxides. Alkaline earth metal hydrides are preferred as precursors, as their reaction to form alkaline earth metal hydroxides removes water formed by the reaction without distillation. Calcium hydride is particularly preferred as an alkaline earth metal hydroxide precursor because of its commercial availability and relatively low cost. Although calcium hydride is advantageous for directly removing water, adding calcium hydroxide to form the reaction mixture is preferred for the method of Scheme 1, in which water is removed by azeotropic distillation, because calcium hydroxide does not form hydrogen gas and is easier to scale up, and inherently safer to use than a metal hydride on a large scale.

The alkaline earth metal hydroxide is added to form the reaction mixture such that the molar ratio of alkaline earth metal hydroxide to the compound of Formula 3 is typically in the range of about 0.1 to about 1. Typically a ratio in the range of about 0.5 to about 1 provides a rapid rate of reaction and high product yields.

In the present method the reaction mixture comprises both a polar aprotic solvent and an aprotic solvent capable of forming a low-boiling azeotrope with water. The polar aprotic solvent can comprise a mixture of polar aprotic solvent compounds, but typically is a single polar aprotic solvent compound. As is generally understood in the art, aprotic solvent means a liquid compound that does not have —OH or —NH moieties in its molecular structure. Also as is generally understood in the art, polar solvent means a liquid compound that has a dielectric constant greater than 15. For the present method, polar aprotic solvents of particular note are sufficiently polar to be miscible with water in all proportions at room temperature (e.g., about 20 to 25° C.). The polar aprotic solvent most preferably has a boiling point higher than the boiling point of the low-boiling azeotrope, so that the polar aprotic solvent is not removed from the reaction mixture. These properties are best provided by amide and sulfoxide solvents, which are commercially available at relatively low cost. By amide solvents is meant solvent compounds containing a carboxamide molecular moiety. Common examples of amide solvents are N,N-dimethylformamide, N,N-dimethylacetamide and N-methylpyrrolidinone. Sulfoxide solvents comprise a sulfoxide molecular moiety; common examples include dimethyl sulfoxide (also known as methyl sulfoxide) and sulfolane. N,N-dimethylformamide is most preferred, as it provides excellent results, has a boiling point substantially greater than water but still can be readily removed by distillation, and is commercially available at relatively low cost.

In the present method, inclusion of an aprotic solvent capable of forming a low-boiling azeotrope with water facilitates removal by distillation of water formed as a byproduct. The aprotic solvent is ordinarily a single solvent compound, but can also be a mixture of solvent compounds (e.g., xylene isomers). By low-boiling azeotrope is meant an azeotrope having a boiling point less than both the boiling point of water and the boiling point of the aprotic solvent. By definition, low-boiling azeotropes containing water have normal boiling points of less than 100° C. (i.e. the normal boiling point of water). Thus the boiling point of the low-boiling azeotrope will be substantially less than the boiling points of the compounds of Formulae 1, 2 and 3, and these compounds will remain in the reaction mixture during distillation. As already mentioned, preferably the polar aprotic solvent and the aprotic solvent capable of forming a low-boiling azeotrope are selected so that the polar aprotic solvent has a boiling point higher than the azeotrope so that the polar aprotic solvent is not removed during the distillation. Aprotic solvents forming azeotropes with water are well known in the art, and compendia have been published listing their boiling points (see, for example, *Azeotropic Data*, Number 6 in the Advances in Chemistry Series, American Chemical Society, Washington, D.C., 1952, particularly pages 6-12). Examples of suitable aprotic solvents forming low-boiling azeotropes with water include esters such as ethyl acetate, aromatic hydrocarbons such as benzene and toluene, and ethers such as tert-butyl methyl ether, tetrahydrofuran and 1,4-dioxane. Preferably, the azeotrope formed by the aprotic solvent and water contains a higher percentage of water than is soluble in the aprotic solvent at room temperature (e.g., 15-35° C.), thus facilitating large-scale separation of water from the condensed azeotrope in a decanter trap, and recycling the water-depleted aprotic solvent to the middle of the distillation column. Therefore water-immiscible aprotic solvents such as ethyl acetate, benzene, toluene and tert-butyl methyl ether are preferred over tetrahydrofuran and 1,4 dioxane, which are miscible with water.

Tert-butyl methyl ether has been discovered to be particularly useful as an aprotic solvent in the present method. Tert-butyl methyl ether forms a water azeotrope boiling at 52.6° C. and containing 4% water and 96% tert-butyl methyl ether, and therefore is able to rapidly transfer water by distillation from the reaction mixture. Furthermore, water is soluble in tert-butyl methyl ether to the extent of only about 1%. Therefore in large-scale preparations wherein the amount of tert-butyl methyl ether in the decanter trap is not sufficient to dissolve all the water formed by the reaction, the condensate in the trap will separate into an upper layer comprising tert-butyl methyl ether containing only about 1% water, which can be returned to the middle of the distillation column, and a lower layer comprising predominately water, which can be removed. In addition, the relatively low boiling points of tert-butyl methyl ether and its azeotrope with water accommodate selecting a wide range of reaction temperatures by adjusting the proportion of tert-butyl methyl ether combined with a polar aprotic solvent having a boiling point above 100° C., particularly above 120° C. (e.g., N,N-dimethylformamide). For example, reaction mixtures comprising much more tert-butyl methyl ether than N,N-dimethylformamide (DMF) can boil at pot temperatures not much above 55° C., while a reaction mixtures comprising little tert-butyl methyl ether relative to DMF can boil at a pot temperatures above 100° C. Typically the ten-butyl methyl ether and N,N-dimethylformamide are in a weight ratio in a range from about 0.5 to about 2.

The reaction of the method of Scheme 1 can be conducted over a wide range of temperatures. Typically the reaction temperature is at least about 65° C. Although the reaction proceeds at lower temperatures, the rates are slower, and aprotic solvent-water azeotropes boiling below 50° C. typically comprise relatively little water (e.g., dichloromethane forms azeotrope containing 1.5% water), which slows water removal. More typically the reaction temperature is at least about 70° C. and most typically at least about 75° C. Although high temperatures increase the reaction rate, they can also cause side reactions decreasing product purity and yield. Therefore typically the reaction temperature is not more than about 110° C., more typically not more than about 100° C., and most typically not more than about 90° C.

The compounds of Formulae 2 and 3, alkaline earth metal hydroxide of Formula 4 (or a precursor such as an alkaline earth metal hydride), polar aprotic solvent and aprotic solvent capable of forming a low-boiling azeotrope can be combined in any convenient order to form the reaction mixture.

Reaction progress can be monitored by conventional methods such as thin layer chromatography, HPLC and $^1$H NMR analyses of aliquots. After completion of the reaction, the mixture is typically cooled to room temperature and the product isolated by conventional methods, such as filtration, extraction, distillation and crystallization. For example, alkali metal hydroxides and other solids can be mostly removed by filtration. Water can be added to the filtrate, followed by a strong acid (such as hydrochloric acid) to neutralize any remaining base and help remove polar solvents such as DMF. Separation of the organic phase, further washing with water to remove polar solvents such as DMF, drying over desiccants such as magnesium sulfate or molecular sieves, and then evaporation of the solvent leaves the product, often as a crystalline solid, which can be recrystallized from solvents such as hexanes.

For large-scale preparations in which drying with desiccants is impractical, the separated organic phase can be dried and concentrated by removing by distillation both water and the aprotic solvent capable of forming an azeotrope with water (subsequently referred to herein as the "Reaction Azeotrope Solvent"). The residue can then be diluted with a nonpolar solvent having a boiling point higher than the Reaction Azeotrope Solvent (e.g., hexanes fraction having a 65-70° C. normal boiling point when the Reaction Azeotrope Solvent is tert-butyl methyl ether) and distillation continued to remove the residual Reaction Azeotrope Solvent and optionally some of the nonpolar solvent. Often cooling the mixture comprising product and the nonpolar solvent causes crystallization of the product. Alternatively, the nonpolar solvent can be removed by further distillation or evaporation to leave the product.

Instead of isolating the product, transferring the product to a solvent useful for a subsequent reaction (e.g., the method of Scheme 6) may be more convenient. After removing by distillation both water and the Reaction Azeotrope Solvent, the residue can be diluted with a solvent useful in the subsequent reaction (referred to herein as the "Replacement Reaction Solvent"). Minor amounts of residual Reaction Azeotrope Solvent may be acceptable in the subsequent reaction. Alternatively, if the Replacement Reaction Solvent has a boiling point higher than the Reaction Azeotrope Solvent (e.g., tetrahydrofuran as Replacement Reaction Solvent when the Reaction Azeotrope Solvent is tert-butyl methyl ether), the residual Reaction Azeotrope Solvent can be easily removed by distillation.

The method of Scheme 1 typically provides the compound of Formula 1 as a mixture of E and Z geometric isomers (denoted by the wavy line in Formula 1), in which one isomer may predominate. Purification methods such as recrystallization often provide purified products containing mostly or exclusively a single geometric isomer.

In an alternative method for preparing compounds of Formula 1, compounds of Formulae 2 and 3 are contacted with an alkaline earth metal hydride such as calcium hydride in the presence of a polar aprotic solvent such as DMF without needing to include an aprotic solvent capable of forming a low-boiling azeotrope with water or distilling water from the mixture. In this method the alkaline earth metal hydride serves both as a source of base to catalyze the condensation and a drying agent to remove water formed as a byproduct. As the alkaline metal hydride serves as the primary drying agent, stoichiometry requires a molar ratio of at least 0.5 relative to the compounds of Formulae 2 and 3. Typically a ratio of about 1.3 provides a rapid rate of reaction and high product yields. Alkaline earth metal hydrides generally have little solubility in solvents inert to them, so small particle size improves mass transfer and the availability of these reagents to react (e.g., with water). Although typically a molar ratio of alkaline metal hydride to the compound of Formula 3 of not more than about 2 is needed for best results (i.e. high conversion and product yields), large particle size of alkaline earth metal hydrides may require a molar ratio of hydride to the compound of Formula 3 of more than 2 for best results. This method is typically conducted at a temperature of at least about 45° C., more typically at least about 55° C., and typically not more than about 100° C., more typically not more than about 80° C.

In the method of the invention illustrated in Scheme 1a, a compound of Formula 1 is prepared by distilling water from a mixture comprising a compound of Formula 2, a compound of Formula 3, an alkali metal carbonate base of Formula 4a, and an aprotic solvent capable of forming a low-boiling azeotrope with water.

Scheme 1a

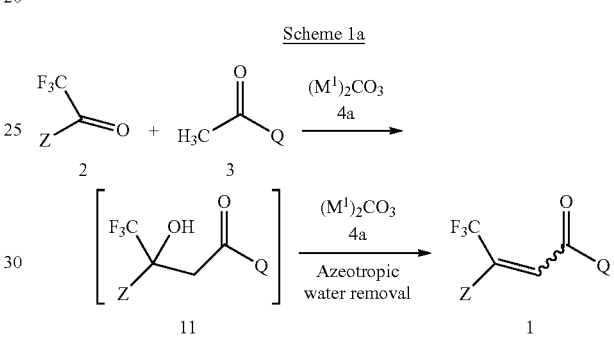

wherein M$^1$ is Li, Na or K.

The first step of this reaction involves an aldol condensation to form a compound of Formula 11. The compound of Formula 11 is not isolated, but instead under the reaction conditions is converted to the compound of Formula 1.

The stoichiometry of this reaction involves equimolar amounts of the compounds of Formula 2 and Formula 3 as described for Scheme 1.

Alkali metal carbonates of Formula 4a have been discovered to be particularly efficacious in providing high yields of compounds of Formula 1. These alkali metal carbonate bases include lithium, sodium or potassium carbonate, with potassium carbonate preferred for its low cost.

The alkali metal carbonate is added to form the reaction mixture such that the molar ratio of alkali metal carbonate to the compound of Formula 3 is typically in the range of about 0.01 to about 0.2. Typically a ratio in the range of about 0.03 to about 0.05 provides complete conversion of compounds of Formula 3 to compounds of Formula 1. The alkali metal carbonate can be added to the reaction mixture in small portions so that the rate of reaction can be controlled, and the rate of generation of water in the reaction vessel can be matched to the rate of water removal by distillation of the solvent/water azeotrope.

In the method of Scheme 1a, acetonitrile has been discovered to be particularly useful as an aprotic solvent in the present method. Acetonitrile forms a water azeotrope boiling at 76.5° C. and containing about 16.3% water and about 83.7% acetonitrile by weight, and therefore is able to rapidly transfer water by distillation from the reaction mixture.

The reaction of the method of Scheme 1a can be conducted over a wide range of temperatures. Typically the reaction temperature is at least about 65° C. Although the reaction proceeds at lower temperatures, the rates are slower, and aprotic solvent-water azeotropes boiling below 50° C. typically comprise relatively little water (e.g., dichloromethane forms azeotrope containing 1.5% water), which slows water removal. More typically the reaction temperature is at least about 80° C. and most typically at least about 85° C. Although high temperatures increase the reaction rate, they can also cause side reactions decreasing product purity and yield. Therefore typically the reaction temperature is not more than about 110° C., more typically not more than about 100° C., and most typically not more than about 90° C.

In the method of the invention illustrated in Scheme 1b, a compound of Formula 1 is prepared by distilling water from a mixture comprising a compound of Formula 2, a compound of Formula 3, a base selected from 1,5-diazabicyclo[4.3.0]non-5-ene, 1,8-diazabicyclo[5.4.0]undec-7-ene, and mixtures thereof, and an aprotic solvent capable of forming a low-boiling azeotrope with water.

Scheme 1b

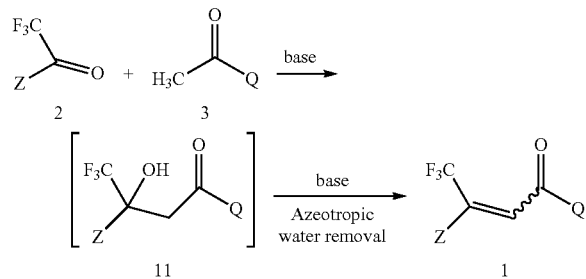

wherein base is 1,5-diazabicyclo[4.3.0]non-5-ene, 1,8-diazabicyclo[5.4.0]undec-7-ene or a mixture thereof.

The first step of this reaction involves an aldol condensation to form a compound of Formula 11. The compound of Formula 11 is not isolated, but instead under the reaction conditions is converted to the compound of Formula 1.

The stoichiometry of this reaction involves equimolar amounts of the compounds of Formula 2 and Formula 3 as described for Scheme 1.

1,5-Diazabicyclo[4.3.0]non-5-ene, 1,8-diazabicyclo [5.4.0]undec-7-ene or mixtures thereof have been discovered to be particularly efficacious in providing high yields of compounds of Formula 1. Both 1,5-diazabicyclo[4.3.0]non-5-ene and 1,8-diazabicyclo-[5.4.0]undec-7-ene are liquids at 25° C. On a large (i.e. commercial) scale, liquids can be added to a reaction mixture more accurately and with less material loss than solids.

1,5-Diazabicyclo[4.3.0]non-5-ene, 1,8-diazabicyclo [5.4.0]undec-7-ene or a mixture thereof is added to form the reaction mixture such that the molar ratio of 1,5-diazabicyclo[4.3.0]non-5-ene, 1,8-diazabicyclo[5.4.0]undec-7-ene or a mixture thereof to the compound of Formula 3 is typically in the range of about 0.01 to about 0.2. Typically a ratio in the range of about 0.03 to about 0.05 provides a rapid rate of reaction and high product yields. The 1,5-diazabicyclo [4.3.0]non-5-ene, 1,8-diazabicyclo[5.4.0]undec-7-ene or mixture thereof can be added to the reaction mixture in small portions so that the rate of reaction can be controlled, and the rate of generation of water in the reaction vessel can be matched to the rate of water removal by distillation of the solvent/water azeotrope.

In the method of Scheme 1b, acetonitrile has been discovered to be particularly useful as an aprotic solvent in the present method. Acetonitrile forms a water azeotrope boiling at 76.5° C. and containing 16.3% water and 83.7% acetonitrile by weight, and therefore is able to rapidly transfer water by distillation from the reaction mixture.

The reaction of the method of Scheme 1b can be conducted over a wide range of temperatures. Typically the reaction temperature is at least about 65° C. Although the reaction proceeds at lower temperatures, the rates are slower, and aprotic solvent-water azeotropes boiling below 50° C. typically comprise relatively little water (e.g., dichloromethane forms azeotrope containing 1.5% water), which slows water removal. More typically the reaction temperature is at least about 80° C. and most typically at least about 85° C. Although high temperatures increase the reaction rate, they can also cause side reactions decreasing product purity and yield. Therefore typically the reaction temperature is not more than about 110° C., more typically not more than about 100° C., and most typically not more than about 90° C.

Regarding the methods of Schemes 1, 1a and 1b, and the above-described alternative method for preparing compounds of Formula 1, in their broadest definitions Z in Formulae 1 and 2 is optionally substituted phenyl, and Q in Formulae 1 and 3 is phenyl or 1-naphthalenyl, each optionally substituted. Q and Z are appendages not directly involved in the aldol condensation and dehydration providing compounds of Formula 1. The reaction conditions for the present methods are relatively mild and thus accommodate a wide range of optional substituents on phenyl and 1-naphthalenyl. Only functionalities most reactive to hydroxide bases are susceptible to being affected. Therefore the particular substituents on the phenyl and 1-naphthalenyl moieties of Q and Z described in the Embodiments (e.g., 1 through 1G, 2 through 20, A through A7) and elsewhere in the present disclosure should be regarded as merely illustrative, as the scope of utility of the present methods is more general.

In the method of the present invention illustrated in Scheme 2, a compound of Formula 2 is prepared from a corresponding compound of Formula 5 by forming a Grignard reagent intermediate (depicted as Formula 12), and then reacting the Grignard reagent with a compound of Formula 6.

Scheme 2

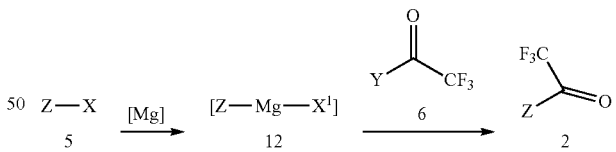

In one embodiment of this method, a compound of Formula 5 is contacted with magnesium metal in the presence of an ethereal solvent to form a Grignard reagent. In the context of the present disclosure and claims, an ethereal solvent contains one or more organic compounds consisting of atoms selected hydrogen, carbon and oxygen and having at least one ether linkage (i.e. C—O—C) but no other functionality. Common examples of ethers include diethyl ether, tetrahydrofuran, 1,4-dioxane and 1,2-dimethoxyethane, but other ethers such as butyl diglyme (1,1'-[oxybis (2,1-ethanediyloxy)]bisbutane) are also employed to prepare and use Grignard reagents. Typically in this embodiment, the ethereal solvent comprises diethyl ether or tetrahydrofuran. More typically the ethereal solvent comprises tetrahydrofuran. When the Grignard reagent is prepared using magnesium metal, $X^1$ in Scheme 2 is the same as X if no other anionic species are added to the reaction mixture. For preparing Grignard reagents from magnesium metal, the metal is typically in the form of turnings, shavings or powder to provide high surface area for reaction. Typically the magnesium metal is contacted with the compound of Formula 5 at a temperature of at least about 0° C., more typically at least about 20° C., and most typically at least about 25° C. Typically the temperature is no more than about 65° C., more typically no more than about 40° C., and most typically no more than about 35° C. As stoichiometry requires at least equimolar amounts of magnesium metal relative to the compound of Formula 5 for complete conversion, the molar ratio of magnesium metal to the compound of Formula 5 is typically at least about 1, more typically at least about 1.02 and most typically at least about 1.05. Although larger excesses of magnesium metal can be used, they provide no advantage and increase solid residues. Typically the molar ratio of magnesium metal to the compound of Formula 5 is no more than about 1.2, and more typically no more than about 1.1.

Alternatively in another embodiment of this method, the Grignard reagent is prepared by contacting the compound of Formula 5 with an alkylmagnesium halide. For an example of this general method of forming Grignard reagents, see J. L. Leazer and R. Cvetovich, *Org. Syn.* 2005, 82, 115-119. The alkylmagnesium halide is typically a secondary alkylmagnesium halide, which is more reactive than a primary alkylmagnesium halide. Typically the alkylmagnesium halide is a $C_1$-$C_4$ alkylmagnesium halide. Of note is the alkylmagnesium halide being an isopropylmagnesium halide, particularly isopropylmagnesium chloride. In this embodiment of the present method, $X^1$ in Scheme 2 represents a mixture of anions provided both by X in the compound of Formula 5 and the halide of the alkylmagnesium halide. For example, if X is I and the alkylmagnesium halide is isopropylmagnesium chloride, then $X^1$ represents a mixture of Cl and I (present as anions). In this embodiment, the compound of Formula 5 is contacted with the alkylmagnesium halide in the presence of an ethereal solvent. Typically the compound of Formula 5 is contacted with the alkylmagnesium halide at a temperature of at least –30° C., more typically at least –20° C. and most typically at least about –10° C. Typically the temperature is no more than about 40° C., more typically no more than about 20° C., and most typically no more than about 10° C. Typically in this embodiment, the ethereal solvent comprises diethyl ether, tetrahydrofuran or a mixture thereof, and more typically the ethereal solvent comprises tetrahydrofuran. As stoichiometry requires at least equimolar amounts of alkylmagnesium halide relative to the compound of Formula 5 for complete conversion, the molar ratio of the alkyl magnesium halide to the compound of Formula 5 is typically at least about 1, and more typically at least about 1.05. Although larger excesses of alkylmagnesium halide can be used, they can subsequently react with the compound of Formula 6, so that more compound of Formula 6 is required and more byproduct is produced. Typically the molar ratio of the alkyl magnesium halide to the compound of Formula 5 is no more than about 1.2, and more typically no more than about 1.15. However, larger amounts of alkylmagnesium halide can be desirable to compensate for water impurities in the reaction solvent.

As is well known in the art, Grignard reagents react very rapidly with solvents containing hydroxy groups, including water, and thus solvents for preparing and using Grignard reagents should contain as little impurity water as feasible, i.e. be anhydrous. Also, as Grignard reagents react with oxygen, the reaction mixtures are preferably protected from oxygen, e.g., by being blanketed by nitrogen or argon gas.

For both embodiments of this method, and particularly the embodiment forming the Grignard reagent using an alkylmagnesium halide, the method can be conducted in the presence of an aromatic hydrocarbon solvent in addition to the ethereal solvent. The term "aromatic hydrocarbon solvent" in this method denotes a solvent comprising one or more aromatic hydrocarbon compounds. Aromatic hydrocarbon compounds contain only carbon and hydrogen atoms and for aromaticity comprise at least one benzene ring, which can be substituted with hydrocarbon moieties such as alkyl groups. Aromatic hydrocarbon solvents commonly comprise one or more of benzene, toluene and xylene (which is typically present as a mixture of isomers). Because aromatic hydrocarbon solvents are higher boiling than common ethereal solvents such as diethyl ether and tetrahydrofuran, including aromatic hydrocarbon solvents in the reaction mixture forming the Grignard reagent improves the margin of safety in large-scale production. The formation of Grignard reagents is generally exothermic, and in the event of loss of cooling and subsequent loss of the lower boiling ethereal solvent, the presence of the higher boiling aromatic hydrocarbon solvent will curtail the reaction. For the present method, toluene is particularly preferred as the aromatic hydrocarbon solvent, because of its low cost, relatively low toxicity, low freezing point and moderately high boiling point.

According to this method, the reaction mixture containing the Grignard reagent formed from the compound of Formula 5 is then contacted with a compound of Formula 6 to give a compound of Formula 2. The compound of Formula 6 is typically contacted with the reaction mixture containing the Grignard reagent at a temperature of at least about –0.80° C., more typically at least about –25° C., and most typically at least about –5° C. The temperature is typically no more than about 0° C. Typically the compound of Formula 6 is added to the reaction mixture containing the Grignard reagent in solution, and an excess of compound of Formula 6 relative to the Grignard reagent formed from the compound of Formula 5 is used. Alternatively, the reaction mixture containing the Grignard reagent formed from the compound of Formula 5 can be added to an excess of the compound of Formula 6. When the Grignard reagent is prepared from magnesium metal, the molar ratio of compound of Formula 6 relative to the compound of Formula 5 is typically at least about 1.05 and more typically at least about 1.1, and typically no more than about 1.3 and more typically no more than about 1.2. When the Grignard reagent is prepared from an alkylmagnesium halide, the amount of alkylmagnesium halide used is more relevant than the amount of the compound of Formula 5 relative to the compound of Formula 6, because excess alkylmagnesium halide can also react with the compound of Formula 6. In this embodiment the ratio of the compound of Formula 6 to the alkylmagnesium halide used is typically at least about 1.05 and more typically at least about 1.1, and typically no more than about 1.3 and more typically no more than about 1.2.

The reaction mixture is typically worked up by addition of an aqueous mineral acid such as hydrochloric acid, and extracting the product into moderately polar, water-immiscible organic solvent such as diethyl ether, dichloromethane or toluene. Usually the compound of Formula 2 is obtained in a mixture with its hydrate derivative and its alkyl hemiketal derivative (from alkanol byproduct formed from the compound of Formula 6 when Y is $OR^{11}$). Either or both of these derivatives of the compound of Formula 2 can be conveniently converted to the compound of Formula 2 by treatment (i.e. contact) with a strong acid such as an organic sulfonic acid, e.g., p-toluenesulfonic acid, in the presence of an aprotic organic solvent, and removing the water and/or alkanol formed by distillation. Preferably the aprotic organic solvent is immiscible with water. Typically the aprotic organic solvent comprises one or more solvents selected from hydrocarbons such as heptane or toluene and halogenated hydrocarbons such as 1,2-dichloroethane. During the distillation, the reaction mixture in the pot is typically heated to at least about 45° C., more typically at least about 80° C., typically no more than about 120° C., more typically no more than about 110° C., and most typically no more than about 100° C. Solvents such as heptane, toluene and 1,2-dichloroethane and their azeotropes with water and alkanols have normal boiling points accommodating these reaction temperatures. Solvents such as toluene that form low-boiling azeotropes with water and alkanols are preferred. After removal of water and alkanols, the distillation can be continued to remove the solvent, and continued at reduced pressure to isolate the product compound of Formula 2.

The method of Scheme 2 is particularly useful when X is I (i.e. iodo), because this facilitates preparation of compounds of Formula 2 wherein Z is a phenyl ring optionally substituted with up to 5 substituents selected from not just F, alkyl, fluoroalkyl, alkoxy, fluoroalkoxy, alkylthio and fluoroalkylthio, but also Cl and Br, which would be more likely to react with magnesium metal or alkylmagnesium halides if X were Cl or Br. Although Grignard reagents are more often prepared from chloro- or bromophenyl compounds, iodophenyl compounds (i.e. X is I) are discovered to work well in forming Grignard reagents, and moreover when X is I the phenyl ring can be substituted with halogens at other positions, particularly the 3- and 5-positions (relative to X), which is especially useful for forming insecticidal 4,5-dihydroisoxazole compounds.

Of note is the method of Scheme 2 wherein X is I and Z is phenyl substituted at the 3- and 5-positions relative to X with substituents independently selected from F, Cl, Br and CF$_3$, particularly wherein one substituent is CF$_3$ and the other substituent is CF$_3$, Cl or Br, more particularly wherein one substituent is CF$_3$ and the other substituent is Cl or Br, and most particularly wherein one substituent is CF$_3$ and the other substituent is Cl.

Compounds of Formulae 5 and 6 can be prepared by a wide variety of methods known in the art. Many of these compounds are known, and a substantial number are commercially available. The above noted embodiment of the method of Scheme 2 involves compounds of Formula 5 wherein X is I (e.g., 1-chloro-3-iodo-5-(trifluoromethyl) benzene). These compounds can be prepared by the method illustrated in Scheme 3. In this method a compound of Formula 13 is diazotized to form a diazonium salt intermediate, which is then reduced to form the compound of Formula 5a (i.e. Formula 5 wherein X is I).

Scheme 3

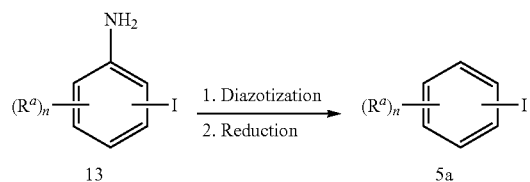

wherein R$^a$ are substituents such as R$^2$ as defined in Embodiment 3H.

In this method, a compound of Formula 13 is contacted with sodium nitrite in the presence of a mineral acid such as hydrochloric acid or sulfuric acid. Usually for best results two or more molar equivalents of the mineral acid are required relative to the number of moles of the compound of Formula 5a used in the reaction. The reaction is typically conducted in a suitable solvent such as aqueous hydrochloric acid or acetic acid. A temperature in the range from about −5 to about 5° C. is usually employed for the preparation of the diazonium salt. The diazonium salt of a compound of Formula 13 is then contacted with a reducing agent such as hypophosphorous acid or ethanol to provide a compound of Formula 5a. The reduction reaction is usually conducted in the same solvent as was used for the diazonium salt formation at a temperature from about 5 to about 20° C. The product of Formula 5a can be isolated by standard techniques such as crystallization, extraction, and distillation. The diazotization and reduction of anilines by this general method is well known and has been reviewed; see, for example, N. Kornblum, *Org. Reactions* 1944, 2, 262-340.

2-Chloro-6-iodo-4-(trifluoromethyl)benzenamine, 4-chloro-2-iodo-6-(trifluoromethyl)-benzenamine and 2-chloro-4-iodo-6-(trifluoromethyl)benzamine are of particular note as compounds of Formula 13 for preparing 1-chloro-3-iodo-5-(trifluoromethyl)benzene as the compound of Formula 5a by this method.

Compounds of Formula 13 can be prepared from compounds of Formula 14 by iodination as shown in Scheme 4.

Scheme 4

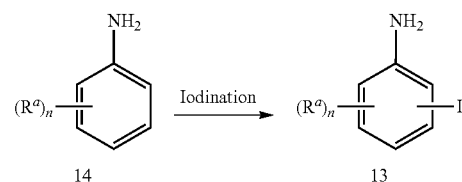

wherein R$^a$ are substituents such as R$^2$ as defined in Embodiment 3H.

In this method a compound of Formula 14 is contacted with an iodination reagent such as iodine monochloride in a suitable solvent such as water or acetic acid. Optionally hydrochloric acid can be included in the reaction mixture to increase the solubility of the compound of Formula 14 and the iodine monochloride in the reaction medium. Usually only about one molar equivalent of iodine monochloride is needed to completely convert the compound of Formula 14 to the compound of Formula 13. Larger molar excesses of iodine monochloride can be used to shorten the reaction time, but with increased process cost. The reaction can be conducted in a temperature range from about 0 to about 100° C., typically at temperature of about 50° C. The product of Formula 13 can be isolated by conventional means, such as filtration, extraction and distillation.

As illustrated in Scheme 5, compounds of Formula 13a containing at least one chlorine or bromine moiety can also be prepared by contacting corresponding compounds of Formula 13 with a suitable chlorinating or brominating agent such as chlorine, hydrochloric acid/hydrogen peroxide, or hydrobromic acid/hydrogen peroxide.

Scheme 5

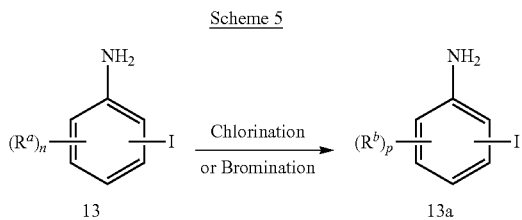

wherein $R^a$ are substituents such as $R^2$ as defined in Embodiment 3H; at least one $R^b$ is Cl (from chlorination) or Br (from bromination) and the other instances of $R^b$ are $R^a$ substituents of Formula 13; and p=n+number of chlorine or bromine atoms from chlorination or bromination, respectively.

The reaction is conducted in a solvent such as water or acetic acid. The temperature range can be from 0 to 100° C. with a temperature range between 25 and 50° C. preferred.

In another aspect of the present invention, compounds of Formula 1 prepared by the method of Scheme 1, are useful for preparing compounds of Formula 7.

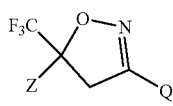

A variety of routes are possible for the preparation of compounds of Formula 7 from compounds of Formula 1. In one method as shown in Scheme 6, a compound of Formula 1 is contacted with hydroxylamine and a base to form a 5-(trifluormethyl)-4,5-dihydroisoxazole compound of Formula 7.

Scheme 6

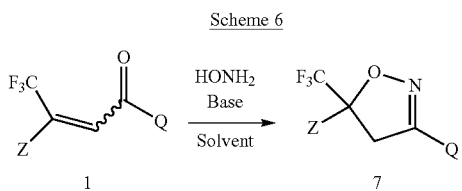

Hydroxylamine can be generated from a mineral acid salt such as hydroxylamine sulfate or hydroxylamine chloride by treatment with a base in a suitable solvent, or can be obtained commercially as 50% aqueous solution. In this method before contact with an enone of Formula 1, hydroxylamine or a mineral acid salt thereof is typically contacted with a base. When a mineral acid salt of hydroxylamine is used, the base is contacted in an amount in excess of the amount needed to convert the hydroxylamine mineral acid salt to hydroxylamine. Base is not consumed in the reaction of Scheme 6, and appears to act as a catalyst for the desired cyclization. Deprotonation of the hydroxylamine with a base prior to contact with an enone of Formula 1 is necessary to obtain good yields, because in the absence of base the reaction of hydroxylamine with enones can afford products other than compounds of Formula 1. Therefore although often about one molar equivalent of base (in addition to any base used to convert a hydroxylamine mineral acid salt to hydroxylamine) is used relative to hydroxylamine, less than one molar equivalent of base can give excellent results. More than one molar equivalent (e.g., up to about 5 molar equivalents) of base relative to hydroxylamine can be used, provided that the excess base does not react with the enone of Formula 1 or the isoxazole of Formula 7.

A molar excess of one to three equivalents of hydroxylamine relative to the enone of Formula 1 can be used. To ensure the cost-effective, complete, and expeditious conversion of the enone of Formula 1 to the isoxazole of Formula 7, in a manner suitable for large-scale production, between about one and about two molar equivalents of hydroxylamine relative to the enone of Formula 1 are typically found to be most suitable.

Suitable bases can include, but are not limited to, alkali metal alkoxides such as sodium methoxide, alkali metal carbonates such as sodium carbonate or potassium carbonate, alkali metal hydroxides such as sodium hydroxide and potassium hydroxide, and organic bases. Preferred organic bases are amine bases having at least one pair of free electrons available for protonation such as pyridine, triethylamine or N,N-diisopropylethylamine. Weaker bases such as pyridine can be used, but stronger bases which efficiently deprotonate hydroxylamine, such as an alkali metal alkoxide or an alkali metal hydroxide, typically provide better results. Because water is an especially useful solvent for deprotonating hydroxylamine, as well as forming hydroxylamine from its salts, bases compatible with water are of particular note. Examples of strong bases that are soluble and compatible with water are alkali metal hydroxides. Sodium hydroxide is preferred, because it is inexpensive and works well for deprotonating hydroxylamine, thereby forming the sodium salt of hydroxylamine in aqueous solution. Alkali metal alkoxides are frequently used in solution in a lower alkanol, often the alkanol corresponding to the alkoxide.

The method of Scheme 6 is conducted in the presence of a suitable solvent. For best results the solvent should be inert to the base and hydroxylamine, and should be capable of dissolving the enone of Formula 1. Suitable organic solvents include alcohols, ethers, nitriles or aromatic hydrocarbons. Water-miscible solvents such as alcohols (e.g., methanol, isopropanol), ethers (e.g., tetrahydrofuran) or nitriles (e.g., acetonitrile) work well with alkali metal hydroxide bases. Solvents which are non-nucleophilic (e.g., ethers and nitriles) often provide the best results. Particularly when a single solvent is used, the most preferred solvents are tetrahydrofuran and acetonitrile.

Alternatively it may be more desirable to conduct the reaction using a mixture of two solvents formed by contacting a solution of the enone of Formula 1 in a solvent such as tetrahydrofuran or acetonitrile with a solution of hydroxylamine and a base such as sodium hydroxide in a second solvent, which acts as the co-solvent in the solvent mixture. Water is particularly useful as a co-solvent, because mineral acid salts of hydroxylamine and alkali metal hydroxide bases such as sodium hydroxide are particularly soluble in water. The rapid generation of hydroxylamine from its mineral acid salt and subsequent deprotonation of hydroxylamine facilitated by water, and the solubility and stability of the deprotonated species in water are especially desirable. In large-scale production, solutions rather than slurries are preferred, because they are easier to handle and transfer in process equipment. When water is the co-solvent, the other solvent is typically a water-miscible solvent such as tetrahydrofuran or acetonitrile.

Other highly polar, hydroxylic solvents such as lower alkanols (e.g., methanol, ethanol) are also particularly useful as co-solvents, because like water they readily dissolve mineral acid salts of hydroxylamine and alkali metal hydroxides. Lower alkanols can give better results than water as a co-solvent when the other solvent is not water-miscible, e.g., tert-butyl methyl ether. When a lower alkanol is used as a co-solvent, particularly with another solvent that is not water-miscible, the base added is often an alkali metal alkoxide instead of an alkali metal hydroxide.

As long as base is present to deprotonate hydroxylamine, the hydroxylamine, the base and the enone of Formula 1 can be contacted in a variety of ways in the method of Scheme 6. For example, a mixture formed from hydroxylamine and the base (typically in a solvent such as water) can be added to the enone of Formula 1 (typically in a solvent such as tetrahydrofuran or acetonitrile). Alternatively, the hydroxylamine and the base can be concurrently added separately to the enone of Formula 1. In another embodiment, the enone of Formula 1 (typically in a solvent such as tetrahydrofuran or acetonitrile) can be added to a mixture formed from the hydroxylamine and the base (typically in a solvent such as water). In these example embodiments other combinations of solvents can be used; for example, methanol with tert-butyl methyl ether instead of water with tetrahydrofuran or acetonitrile.

The method of Scheme 6 can be conducted at a reaction temperature between about 0 and 150° C., or most conveniently between 20 and 40° C. The product of Formula 7 is isolated by the usual methods known to those skilled in the art including extraction and crystallization.

Compounds of Formulae 7a, 7b and 7c are subsets of compounds of Formula 7 that are of particular note as insecticides.

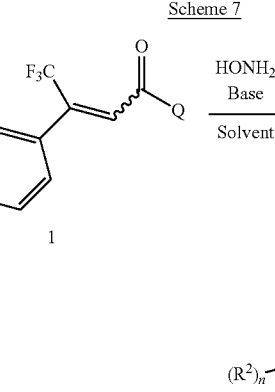

wherein R², R³, R⁴, R⁵ and Rᵛ are as defined in the Summary of the Invention, Exhibit 1 and the Embodiments, and n is an integer from 0 to 5.

Therefore for preparation of compounds of Formulae 7a, 7b and 7c of particular note are embodiments of the method of Scheme 6 shown in Scheme 7 wherein the compound of Formula 1 is prepared by the method of Scheme 1.

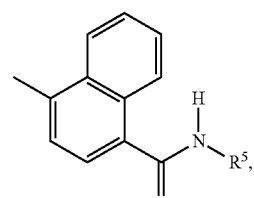

wherein
Q is

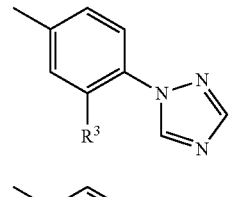

Compounds of Formula 7 can often be prepared from other compounds of Formula 7 by modification of substituents. For example, compounds of Formula 7a can be prepared by aminocarbonylation of compounds of Formula 7d with appropriately substituted amine compounds of Formula 15 as shown in Scheme 8.

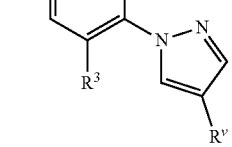

This reaction is typically carried out with an aryl bromide of Formula 7d in the presence of a palladium catalyst under a CO atmosphere. The palladium catalysts used for this method typically comprises palladium in a formal oxidation state of either 0 (i.e. Pd(0)) or 2 (i.e. Pd(II)). A wide variety of such palladium-containing compounds and complexes are useful as catalysts for this method. Examples of palladium-containing compounds and complexes useful as catalysts in the method of Scheme 8 include $PdCl_2(PPh_3)_2$ (bis(triphenylphosphine)palladium(II) dichloride), $Pd(PPh_3)_4$ (tetrakis(triphenylphosphine)-palladium(0)), $Pd(C_5H_7O_2)_2$ (palladium(II) acetylacetonate), $Pd_2(dba)_3$ (tris(dibenzylideneacetone)dipalladium(0)), and [1,1'-bis(diphenylphosphino)ferrocene]dichloropalladium(II). The method of Scheme 8 is generally conducted in a liquid phase, and therefore to be most effective the palladium catalyst preferably has good solubility in the liquid phase. Useful solvents include, for example, ethers such as 1,2-dimethoxyethane, amides such as N,N-dimethylacetamide, and non-halogenated aromatic hydrocarbons such as toluene.

The method of Scheme 8 can be conducted over a wide range of temperatures, ranging from about 25 to about 150° C. Of note are temperatures from about 60 to about 110° C., which typically provide fast reaction rates and high product yields. The general methods and procedures for aminocarbonylation with an aryl bromide and an amine are well known in the literature; see, for example, H. Horino et al., Synthesis 1989, 715; and J. J. Li, G. W. Gribble, editors, *Palladium in Heterocyclic Chemistry: A Guide for the Synthetic Chemist*, 2000.

Compounds of Formula 7d can be prepared by the method of Scheme 6 from compounds of Formula 1, which are prepared by the method of Scheme 1 according to the present invention.

Compounds of Formula 7a can also be prepared by coupling a carboxylic acid compound of Formula 7e with an appropriately substituted amino compound of Formula 15 as shown in Scheme 9.

Scheme 9

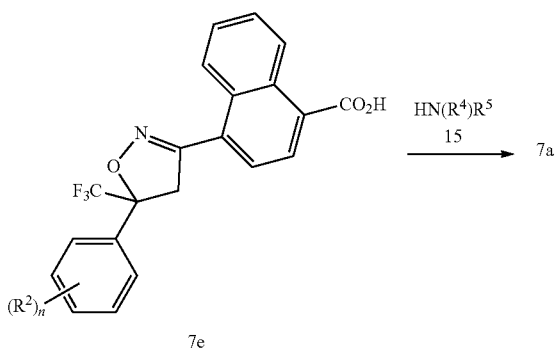

7e

This reaction is generally carried out in the presence of a dehydrating coupling reagent such as dicyclohexylcarbodiimide, 1-(3-dimethylaminopropyl)-3-ethylcarbodiimide, 1-propanephosphonic acid cyclic anhydride or carbonyl diimidazole in the presence of a base such as triethylamine, pyridine, 4-(dimethylamino)pyridine or N,N-diisopropylethylamine in an anhydrous aprotic solvent such as dichloromethane or tetrahydrofuran at a temperature typically between about 20 and about 70° C.

Compounds of Formula 7e can be prepared by the method of Scheme 6 from compounds of Formula 1, which are prepared by the method of Scheme 1 according to the present invention. Alternatively, compounds of Formula 7e can be prepared by hydrolyzing ester compounds of Formula 7f as shown in Scheme 10.

Scheme 10

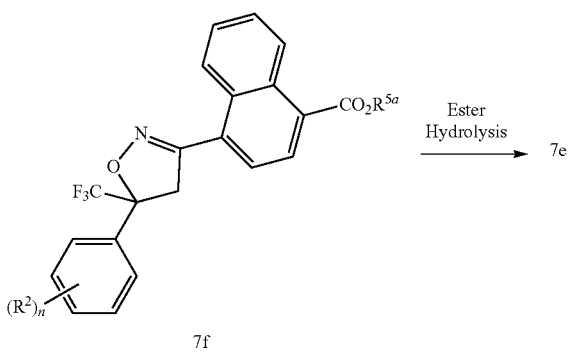

7f wherein $R^{5a}$ is, for example, methyl or ethyl.

In this method, an ester of Formula 7f is converted to a corresponding carboxylic acid of Formula 7e by general procedures well known in the art. For example, treatment of a methyl or ethyl ester of Formula 7f with aqueous lithium hydroxide in tetrahydrofuran, followed by acidification yields the corresponding carboxylic acid of Formula 7e.

Compounds of Formula 7f can be prepared by the method of Scheme 6 from compounds of Formula 1, which are prepared by the method of Scheme 1 according to the present invention.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets and "br" means broad.

Example 1

Preparation of methyl 4-[5-(3,5-dichlorophenyl)-4,5-dihydro-5-(trifluoromethyl)-3-isoxazolyl]-1-naphthalenecarboxylate Step A: Preparation of methyl 4-[3-(3,5-dichlorophenyl)-4,4,4-trifluoro-1-oxo-2-buten-1-yl]-1-naphthalenecarboxylate A mixture of methyl 4-acetyl-1-naphthalenecarboxylate (5.36 g, 23.4 mmol), 1-(3,5-dichlorophenyl)-2,2,2-trifluoroethanone (5.68 g, 23.4 mmol), calcium hydroxide (0.172 g, 2.3 mmol), N,N-dimethylformamide (16 mL), and tert-butyl methyl ether (32 mL) was placed in a thermometer-equipped reaction vessel. The reaction vessel was connected to a ten-plate Oldershaw column, the output of which was condensed and fed into a decanter initially filled with tert-butyl methyl ether. A nitrogen atmosphere was maintained in the apparatus. The upper part of the decanter was connected to return condensate to the fifth plate of the Oldershaw column. This arrangement ensured that wet (containing dissolved water) tert-butyl methyl ether from the decanter was not returned to the reaction vessel. A drain valve at the bottom of the decanter allowed removing tert-butyl methyl ether in addition to water from the decanter. The reaction mixture was heated to distill the tert-butyl methyl ether/water azeotrope. As the decanter trap contained an amount of tert-butyl methyl ether sufficient to dissolve all of the water formed by the reaction, the condensate in the trap did not separate into layers containing predominately water and predominately tert-butyl methyl ether. Because the reaction mixture initially contained mostly tert-butyl methyl ether, the mixture boiled at a temperature not much exceeding the normal boiling point of tert-butyl methyl ether (e.g., about 65-70° C.). The reaction appeared to proceed relatively slowly at this temperature, so condensate was gradually drained from the decanter trap to remove tert-butyl methyl ether. As the concentration of ten-butyl methyl decreased in the reaction mixture, the temperature of the boiling mixture increased. Tert-butyl methyl ether was removed by draining the decanter until the temperature of the boiling reaction mixture reached about 75 to 80° C. To maintain this temperature range, tert-butyl methyl ether was added as needed to compensate for loss of solvent from the apparatus. The total time from beginning heating the reaction mixture to stopping distillation, not including a shutdown period overnight, was about 15 h. During this time period a further portion of calcium hydroxide (1.34 g, 18.1 mmol) was added to increase the reaction rate.

To isolate the product, the mixture was cooled to room temperature and filtered. The collected solid was washed with tert-butyl methyl ether (10 mL). Water (100 mL) was added, and the aqueous layer was acidified with hydrochloric acid. The organic phase was washed with water (100 mL), dried, and evaporated to give the product as a yellow solid (10.1 g, 95% yield) melting at 91-91.5° C. (after recrystallization from hexanes). The following spectra were of the product recrystallized from hexanes.

IR (nujol) 1723, 1670, 1560, 1280, 1257, 1230, 1186, 1171, 1132, 1098, 1022, 804 cm$^{-1}$.

$^1$H NMR (CDCl$_3$) 8.78-8.76 (m, 1H), 8.32-8.30 (m, 1H) 8.02 (d, J=7.6 Hz, 1H) 7.65-7.62 (m, 3H), 7.34 (s, 1H), 7.07-7.06 (m, 1H), 6.94 (d, 1.7 Hz, 2H), 4.03 (s, 3H).

Step B: Preparation of methyl 4-[5-(3,5-dichlorophenyl)-4,5-dihydro-5-(trifluoromethyl)-3-isoxazolyl]-1-naphthalenecarboxylate Sodium hydroxide (50%, 3.50 g, 43.7 mmol) was added to a solution of hydroxylamine sulfate (1.8 g, 11.0 mmol) in water (22 mi.). When the mixture had cooled to room temperature a portion of the mixture (~50%) was added dropwise over 4 minutes to methyl 4-[3-(3,5-dichlorophenyl)-4,4,4-trifluoro-1-oxo-2-buten-1-yl]-1-naphthalenecarboxylate (i.e. the product of Step A) (5.00 g, 11.0 mmol) in tetrahydrofuran (55 mL) at room temperature. After 30 minutes a further portion (~10%) of the aqueous mixture was added. The mixture was stirred for a further 15 minutes. The mixture was partitioned between hydrochloric acid (1 N, 50 mL) and tert-butyl methyl ether (50 mL). The organic phase was evaporated, and the solid obtained was stirred in hot methanol. The mixture was cooled and filtered to give the product as a white solid (4.50 g, 87%) melting at 137.3-138° C. (after recrystallization from methanol). The following spectra were of the product recrystallized from methanol.

IR (nujol) 1716, 1569, 1518, 1433, 1332, 1309, 1288, 1251, 1192, 1167, 1139, 1114, 1102, 1027, 1006, 910, 867, 855 cm$^{-1}$.

$^1$H NMR (CDCl$_3$) 8.89-8.87 (m, 1H), 8.80-8.78 (m, 1H), 8.10 (d. J=7.6 Hz, 1H), 7.69-7.66 (m, 2H), 7.56-7.53 (m, 3H), 7.46 (t, J=2 Hz, 1H), 4.27 (½ABq, J=17 Hz, 1H), 4.03 (s, 3H), 3.91 (½ABq, J=17 Hz, 1H).

Example 2

Preparation of methyl 4-[5-[3,5-bis(trifluoromethyl)phenyl]-4,5-dihydro-5-(trifluoromethyl)-3-isoxazolyl]-1-naphthalenecarboxylate Step A: Preparation of methyl 4-[3-[3,5-bis(trifluoromethyl)phenyl]-4,4,4-trifluoro-1-oxo-2-buten-1-yl]-1-naphthalenecarboxylate A mixture of methyl 4-acetyl-1-naphthalenecarboxylate (5.36 g, 23.5 mmol), 1-[3,5-bis(trifluoromethyl)phenyl]-2,2,2-trifluoroethanone (7.28 g, 23.5 mmol), calcium hydroxide (1.40 g, 18.9 mmol), N,N-dimethylformamide (16 mL) and tert-butyl methyl ether (32 mL) was boiled with provision of the apparatus comprising a ten-plate Oldershaw column and decanter described in Example 1, Step A for removal of the tert-butyl methyl ether/water azeotrope. As the decanter trap contained an amount of tert-butyl methyl ether sufficient to dissolve all of the water formed by the reaction, the condensate in the trap did not separate into layers containing predominately water and predominately tert-butyl methyl ether. Tert-butyl methyl ether was removed by gradually draining the decanter trap until the pot temperature was 85° C. To maintain this temperature, tert-butyl methyl ether was added as needed to compensate for loss of solvent from the apparatus. The total time from beginning heating the reaction mixture to stopping distillation, not including a shutdown period overnight, was about 10 h. During this time period no additional calcium hydroxide was added to the reaction mixture.

To isolate the product, the mixture was cooled to room temperature and was filtered. The solid was washed with tert-butyl methyl ether and the filtrate was washed with water (30 mL), and diluted with tert-butyl ether. The mixture was evaporated to give the product as a yellow solid (12.1 g, 99%) melting at 91.5-92° C. (after recrystallization from hexanes). The following spectra were of the product recrystallized from hexanes.

IR (nujol) 1720, 1685, 1515, 1441, 1405, 1345, 1280, 1261, 1187, 1171, 1147, 1129, 1097, 1024, 899, 856 cm$^{-1}$.

$^1$H NMR (CDCl$_3$) 8.74-8.72 (m, 1H), 8.23-8.21 (m, 1H) 7.99 (d, J=7.3 Hz, 1H), 7.67 (d, J=7.6 Hz, 1H), 7.64-7.57 (m, 3H), 7.51 (s, 2H), 7.47 (d, J=1.4 Hz, 1H), 4.04 (s, 3H).

Step B: Preparation of methyl 4-[5-[3,5-bis(trifluoromethyl)phenyl]-4,5-dihydro-5-(trifluoromethyl)-3-isoxazolyl]-1-naphthalenecarboxylate Sodium hydroxide (50%, 1.53 g, 38.2 mmol) was added to hydroxylamine sulfate (1.57 g, 9.57 mmol) in water (18 mL). A portion of the solution (~51%, ~9.8 mmol of hydroxylamine) was added dropwise to methyl 4-[3-[3,5-bis(trifluoromethyl)phenyl]-4,4,4-trifluoro-1-oxo-2-buten- 1-yl]-1-naphthalenecarboxylate (i.e. the product of Step A) (5.00 g, 9.61 mmol) in tetrahydrofuran (45 mL). After ~45 min the mixture was poured into hydrochloric acid (1 N, 100 mL) and was extracted with ether (3×80 mL).

The combined organic extracts were washed with water (80 mL), dried and evaporated. The material was stirred in hot methanol, then cooled to room temperature, collected under filtration and dried in vacuum to give the product as a white solid (4.14 g, 80% yield) melting at 130-131° C. (after recrystallization from methanol). The following spectra were of the product recrystallized from methanol.

IR (nujol) 1722, 1515, 1437, 1330, 1284, 1208, 1193, 1174, 1128, 1106, 1025, 1009, 916, 903, 859, 842 cm$^{-1}$.

$^1$H NMR (CDCl$_3$) 8.89-8.87 (m, 1H), 8.82-8.79 (m, 1H), 8.14-8.09 (m, 3H), 8.0 (a, 1H), 7.70-7.67 (m, 2H), 7.56 (d, J=7.6 Hz, 1H), 4.39 (½ ABq, J=17.3 Hz, 1H), 4.03 (s, 3H), 3.96 (½ ABq, J=17.6 Hz, 1H).

Example 3

Alternative Preparation of methyl 4-[3-(3,5-dichlorophenyl)-4,4,4-trifluoro-1-oxo-2-buten-1-yl]-1-naphthalenecarboxylate A solution of 1-(3,5-dichlorophenyl)-2,2,2-trifluoroethanone (1.42 g, 5.84 mmol) in N,N-dimethylformamide (5.5 mL) was added to calcium hydride (0.280 g, 6.66 mmol). A solution of methyl 4-acetyl-1-naphthalenecarboxylate (1.34 g, 5.88 mmol) in N,N-dimethylformamide (5.5 mL) was added to the mixture. The mixture was warmed to 45-50° C. for 8 h. The mixture was cooled to room temperature overnight. After a further 4 h at 60° C. the mixture was cooled to room temperature and was added dropwise to hydrochloric acid (1 N, 100 mL). The mixture was extracted with ethyl acetate (2×100 mL), and the combined extracts were dried and evaporated to give the product (2.7 g, 102% yield), which contained a little N,N-dimethylformamide. The $^1$H NMR spectrum of the major isomer was recorded as follows.

$^1$H NMR (CDCl$_3$) 8.78-8.75 (m, 1H), 8.33-8.30 (m, 1H), 8.02 (d, J=7.7 Hz, 1H), 7.66-7.61 (m, 3H), 7.34 (s, 1H), 7.07-7.04 (m, 1H), 6.94 (d, J=2 Hz, 2H) 4.03 (s, 3H).

Example 4

Preparation of 2-chloro-6-iodo-4-(trifluoromethyl)benzenamine

Iodine monochloride (17.2 g, 108 mmol) in hydrochloric acid (36%, 21.4 g) and water (35 mL) was added dropwise to 2-chloro-4-(trifluoromethyl)benzenamine (20.0 g, 102 mmol) in hydrochloric acid (36%, 20.7 g) and water (140 mL). The mixture was warmed to 50° C. for a total of 8 h. Sodium hydroxide (50%, 33.5 g, 419 mmol) was added to the mixture at room temperature. The mixture was extracted with dichloromethane (2×250 mL), and the extracts were dried and evaporated to give the product as an oil (31.83 g, 97% yield).

$^1$H NMR (CDCl$_3$) 7.78 (s, 1H), 7.5 (s, 1H), 4.87 (br s, 2H).

Example 5

Preparation of 1-chloro-3-iodo-5-(trifluoromethyl)benzene

2-Chloro-6-iodo-4-(trifluoromethyl)benzenamine (i.e. the product of Example 4) (31.8 g, 98.9 mmol) was added to hydrochloric acid (36%, 190 mL) and the mixture was warmed to 55-60° C. for 20 min. The mixture was cooled to 0° C. Sodium nitrite (13.6 g, 197 mmol) in water (36 mL) was added over 30 min. When the addition was complete the mixture was stirred at 0-5° C. for 70 min. Hypophosphorous acid (50%, 36.5 mL, 351 mmol) was added dropwise at 5-10° C. over 40 min. When the addition was complete the mixture spontaneously warmed briefly to 35° C., and was then cooled to 10-20° C. After stirring at 10-20° C. for 2 h, the mixture was stored in a refrigerator overnight. Then the mixture was warmed to room temperature and was stirred for 1 h. The mixture was diluted with water (400 mL) and extracted with ether (2×250 mL). The combined extracts were dried and evaporated. Distillation gave the product as an oil (19.93 g, 66% yield), b.p. 98-112° C. at 2.0 kPa.

$^1$H NMR (CDCl$_3$) 7.89 (a, 1H), 7.84 (s, 1H), 7.58 (s, 1H).

Example 6

Preparation of 1-[3-chloro-5-(trifluoromethyl)phenyl]-2,2,2-trifluoroethanone

A tetrahydrofuran solution of isopropylmagnesium chloride (2 M, 36.0 mL, 71.8 mmol) was added dropwise to a solution of 1-chloro-3-iodo-5-(trifluoromethyl)benzene (i.e. the product of Example 5) (20.0 g, 65.3 mmol) in tetrahydrofuran (30 mL) at −5° C. The mixture was stirred for 1 h at 0-5° C. Methyl trifluoroacetate (10.0 g, 78.1 mmol) was added dropwise to the mixture while maintaining the temperature 0-5° C. When the addition was complete mixture was stirred for 90 min.

Hydrochloric acid (1 N, 100 mL) was added dropwise to the mixture at 0-5° C. When the addition was complete the mixture was extracted with ether (2×100 mL).

The combined extracts were dried and evaporated. The oil was dissolved in toluene (55 mL), and p-toluenesulfonic acid monohydrate (0.100 g, 0.525 mmol) was added to the mixture. The mixture was boiled for 30 min, and the water/toluene methanol/toluene azeotropes were removed by distillation at atmospheric pressure. The distillation was continued at reduced pressure to give the product as an oil (12.4 g, 69% yield), b.p. 93-103° C. at 6.7 kPa.

$^1$H NMR (CDCl$_3$) 8.21-8.19 (m, 2H), 7.95 (s, 1H).

Example 7

Preparation of 4-[5-(3-chloro-5-(trifluoromethyl)phenyl)-4,5-dihydro-5-(trifluoromethyl)-3-isoxazolyl]-N-[2-oxo-2-[(2,2,2-trifluoroethyl)amino]ethyl]-1-naphthalenecarboxamide Step A: Preparation of 4-acetyl-1-naphthalenecarbonyl chloride Thionyl chloride (35.00 g, 0.29 mol) was added to a solution of 4-acetyl-1-naphthalenecarboxylic acid (51.70 g, 0.24 mol) in toluene (350 mL). The mixture was warmed to 90° C. for 8.5 h. After cooling to 25° C. the solvent was removed under reduced pressure to give the title product as an off-white solid (55.1 g, 98.7% yield).

IR (nujol) 1758, 1681, 1515, 1352, 1282, 1245, 1218, 1190, 1117, 1053, 923, 762 cm$^{-1}$.

$^1$H NMR (CDCl$_3$): 8.72-8.69 (m, 1H), 8.50 (d, J=7.6 Hz, 1H), 8.44-8.41 (m, 1H), 7.82 (d, J=7.9 Hz, 1H), 7.76-7.65 (m, 2H), 2.77 (s, 3H).

Step B: Preparation of 4-acetyl-N-[2-oxo-2-[(2,2,2-trifluoroethyl)amino]ethyl]-1-naphthalenecarboxamide A solution of 2-amino-N-(2,2,2-trifluoroethyl)acetamide (21.90 g, 0.14 mol) in 1,2-dichloroethane (80 mL) was added dropwise over 15 min to a solution of the product of Example 7, Step A (32.50 g, 0.14 mol) in 1,2-dichloroethane (160 mL) at a temperature of 25 to 30° C. The resulting mixture was further stirred for 10 min at 25° C. A solution of triethylamine (14.20 g, 0.14 mol) in 1,2-dichloroethane (80 mL) was then added dropwise over 44 min at 25° C., and the mixture was stirred further for 20 min at 25° C. The solvent was removed under reduced pressure, and the residue was dissolved in hot acetonitrile (50 mL). The mixture was then cooled to 25° C., and water (40 mL) was added dropwise. The mixture was further cooled to 0° C. and filtered. The isolated solid was washed with water (100 mL) and dried overnight in a vacuum oven (approximately 16-33 kPa at 50° C.) to provide the title product as an off-white solid (37 g, 75% yield) melting at 169-169° C.

IR (nujol) 3303, 3233, 3072, 1698, 1683, 1636, 1572, 1548, 1447, 1279, 1241, 1186, 1159 cm$^{-1}$.

$^1$H NMR (CD$_3$S(=O)CD$_3$): 8.95 (t, J=5.8 Hz, 1H), 8.72 (t, J=6.5 Hz, 1H), 8.55 (dd, J=6.5, 2 Hz, 1H), 8.37-8.33 (m, 1H), 8.13 (d, J=7.3 Hz, 1H), 7.70-7.60 (m, 3H), 4.07-3.95 (m, 4H), 2.75 (s, 3H).

Step C: Preparation of 4-[3-[3-chloro-5-(trifluoromethyl)phenyl]-4,4,4-trifluoro-1-oxo-2-buten-1-yl]-N-[2-oxo-2-[(2,2,2-trifluoroethyl)amino]ethyl]-1-naphthalenecarboxamide A mixture of the product of Example 7, Step B (10.00 g, 28.38 mmol), 1-[3-chloro-5-(trifluoromethyl)phenyl]-2,2,2-trifluoroethanone (9.00 g, 32.5 mmol), calcium hydroxide (1.05 g, 14.2 mmol), N,N-dimethylformamide (20 mL) and tert-butyl methyl ether (32 mL) was placed in a thermometer-equipped reaction vessel. The reaction vessel was connected to a ten-plate Oldershaw column, the output of which was condensed and fed into a decanter initially filled with tert-butyl methyl ether. A nitrogen atmosphere was maintained in the apparatus. The upper part of the decanter was connected to return condensate to the fifth plate of the Oldershaw column. This arrangement ensured that wet (containing dissolved water) tert-butyl methyl ether was not returned from the decanter to the reaction vessel. A drain valve at the bottom of the decanter allowed removing tert-butyl methyl ether in addition to water from the decanter. The reaction mixture was heated to distill the tert-butyl methyl ether/water azeotrope. As the decanter trap contained an amount of tert-butyl methyl ether sufficient to dissolve all of the water formed by the reaction, the condensate in the trap did not separate into layers containing predominately water and predominately tert-butyl methyl ether. Because the reaction mixture initially contained mostly tert-butyl methyl ether, the mixture boiled at a temperature not much exceeding the normal boiling point of tert-butyl methyl ether (e.g., about 65-70° C.). The reaction proceeded relatively slowly at this temperature, so condensate was gradually drained from the decanter trap to remove tert-butyl methyl ether. As the concentration of tert-butyl methyl ether decreased in the reaction mixture, the temperature of the boiling reaction mixture increased. Teri-butyl methyl ether was removed by draining the decanter until the temperature of the boiling reaction mixture reached about 85° C. To maintain this temperature, tert-butyl methyl ether was added as needed to compensate for loss of solvent from the apparatus. The total time from the start of heating the reaction mixture to stopping distillation, not including a shutdown period overnight, was about 6 h.

To isolate the product, the mixture was cooled to room temperature and then added to a mixture of tert-butyl methyl ether (50 mL) and 1 N hydrochloric acid (100 mL,). The organic phase was separated, and heptane (60 mL) was added dropwise. The mixture was filtered to provide the title product as an off-white solid mixture of isomers (14 g, 81% yield) melting at 174.5-177° C.

IR (nujol) 3294, 1697, 1674, 1641, 1541, 1441, 1364, 1313, 1275, 1246, 1163, 1104 cm$^{-1}$.

$^1$H NMR (CD$_3$S(=O)CD$_3$): (major isomer) 8.91 (t, J=6.2 Hz, 1H), 8.73 (t, J=6.4 Hz, 1H), 8.44-8.30 (m, 2H), 8.18 (d, J=7.7 Hz, 1H), 7.97-7.61 (m, 7H), 4.06-3.95 (m, 4H).

Step D: Preparation of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide Aqueous sodium hydroxide (50%, 3.04 g, 38.0 mmol) was added dropwise to a stirred solution of hydroxylamine sulfate (1.48 g, 9.02 mmol) in water (28 mL) at 25 (C. After this addition was complete the product of Example 7, Step C (10.00 g, 16.33 mmol) in tetrahydrofuran (60 mL) was added dropwise over 40 min. After the addition was complete the mixture was stirred further for 30 min. The solvent was removed under reduced pressure and 1 N hydrochloric acid (100 mL) was added. The mixture was extracted with ether (2×100 mL), and the combined extracts were dried and evaporated. The residue was dissolved in acetonitrile (30 mL), cooled to 0° C., and filtered to afford the title product as a white solid (7.84 g, 77% yield) melting at 107-108.5° C. (after recrystallisation from acetonitrile).

IR (nujol) 3312, 1681, 1642, 1536, 1328, 1304, 1271, 1237, 1173, 1116 cm$^{-1}$.

$^1$H NMR (CD$_3$S(=O)CD$_3$): 8.98 (t, J=5.8 Hz, 1H), 8.82 (d, J=7.4 Hz, 1H), 8.74 (t, J=6.5 Hz, 1H), 8.40 (d, J=9.7 Hz, 1H), 8.09 (d, J=15.3 Hz, 2H), 7.93 (d, J=7.6 Hz, 2H), 7.75-7.04 (m, 3H), 4.63 (s, 2H), 4.07-3.96 (4H, m).

Example 7A

Alternative Preparation of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide

Step A: Preparation of 4-[3-[3-chloro-5-(trifluoromethyl)phenyl]-4,4,4-trifluoro-1-oxo-2-buten-1-yl]-N-[2-oxo-2-[(2,2,2-trifluoroethyl)amino]ethyl]-1-naphthalenecarboxamide A mixture of 4-acetyl-N-[2-oxo-2-[(2,2,2-trifluoroethyl)amino]ethyl]-1-naphthalenecarboxamide (100.00 g, 267.23 mmol), 1-[3-chloro-5-(trifluoromethyl)phenyl]-2,2,2-trifluoroethanone (86.92 g, 288.6 mmol) and acetonitrile (500 mL) was placed in a thermometer-equipped reaction vessel. The reaction vessel was connected to a ten-plate Oldershaw column. A nitrogen atmosphere was maintained in the apparatus. The mixture was heated to boiling, at which time the temperature of the top of the column was 82° C. Potassium carbonate was added to the reaction mixture portionwise to control the rate of reaction. Initially, 0.40 g of potassium carbonate was added, followed sequentially by individual 0.1 g additions 30, 60, 120 and 180 minutes, and 0.40 g additions 240 and 300 minutes after the initial addition of potassium carbonate. Prior to addition to the reaction mixture, the potassium carbonate was slurried in a small amount of acetonitrile (approximately 3 mL of acetonitrile was used to slurry the 0.40 g quantities of potassium carbonate, and approximately 2 mL of acetonitrile was used to slurry the 0.1 g quantities of potassium carbonate). The acetonitrile/water azeotrope (bp 76.5° C.) was continuously removed from the top of the column as it was formed. After the final potassium carbonate addition the mixture was boiled for a further 60 minutes. After a total time of 6 h from the initial addition of potassium carbonate, more acetonitrile was removed by distillation until a total of 265 mL of acetonitrile and acetonitrile/water azeotrope had been removed. The mixture was cooled to 25° C., and water (48 mL) was added to the mixture. The mixture was cooled to 0° C. over 30 minutes, held at this temperature for 60 minutes, and then filtered. The isolated solid was washed with acetonitrile:water (96 mL, 26:5 acetonitrile:water).

The product was dried in a vacuum oven (approximately 16-33 kPa at 55° C.) overnight to give the product as an off-white solid (150.51 g as a mixture of isomers, 92.2% yield).

The $^1$H NMR spectrum of the major isomer was identical to the spectrum of the material prepared in Example 7, Step C.

Step B: Preparation of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide A solution of sodium hydroxide (15.10 g of a 50% aqueous solution, 0.19 mmol) in water (total volume 67.5 mL) and a solution of hydroxylamine sulfate (7.75 g, 47.3 mmol) in water (total volume 67.5 mL) were added simultaneously to the product of Example 7A, Step A (51.90 g, 81.78 mmol) in tetrahydrofuran (300 mL) at 25° C. over 75 minutes. After the addition was complete, the mixture was stirred further for 180 minutes. The mixture was acidified to approximately pH 3 by addition of hydrochloric acid (concentrated, approximately 11 g). The aqueous layer was removed, and the remaining organic solution was heated to boiling. Acetonitrile was added, and the acetonitrile/tetrahydrofuran distillate was removed until the distillate temperature reached 82° C., indicating that all of the tetrahydrofuran had been removed. The mixture was allowed to cool to 25° C., and the acetonitrile was removed under reduced pressure. The residue was dissolved in acetonitrile (200 mL), cooled to 0° C., and the resulting mixture was filtered to afford the title product as a white solid (43.45 g, 84% yield).

The 11H NMR spectrum of the product was identical to the spectrum of the material prepared in Example 7, Step D.

Example 7B

Alternative Preparation of 4-[3-[3-chloro-5-(trifluoromethyl)phenyl]-4,4,4-trifluoro-1-oxo-2-buten-1-yl]-N-[2-oxo-2-[(2,2,2-trifluoroethyl)amino]ethyl]-1-naphthalenecarboxamide A mixture of 4-acetyl-N-[2-oxo-2-[(2,2,2-trifluoroethyl)amino]ethyl]-1-naphthalenecarboxamide (50.00 g, 135.1 mmol), 1-[3-chloro-5-(trifluoromethyl)phenyl]-2,2,2-trifluoroethanone (43.93 g, 145.8 mmol) and acetonitrile (250 mL) was placed in a thermometer-equipped reaction vessel. The reaction vessel was connected to a ten-plate Oldershaw column. A nitrogen atmosphere was maintained in the apparatus. The mixture was heated to boiling, at which time the temperature of the top of the column was 82° C. 1,8-Diazabicyclo[5.4.0]undec-7-ene (DBU) was added to the reaction mixture portionwise to control the rate of reaction. Initially, 0.20 g of DBU was added, followed sequentially by individual 0.052 g additions 30, 90, 150 and 210 minutes, and 0.20 g additions 270 and 330 minutes after the initial addition of DBU. Each individual DBU portion was diluted with acetonitrile (2 mL) prior to addition to the reaction mixture. The acetonitrile/water azeotrope (bp 76.5° C.) was continuously removed from the top of the column as it was formed. After the final DBU addition the mixture was boiled for a further 60 minutes. After a total time of 6 h from the initial addition of DBU, more acetonitrile was removed by distillation until a total of 138 mL of acetonitrile and acetonitrile/water azeotrope had been removed. The mixture was cooled to 25° C., and water (24 mL) was added to the mixture. The mixture was cooled to 0° C. over 30 minutes, held at this temperature for 60 minutes, and then filtered. The isolated solid was washed with acetonitrile:water (48 mL, 26:5 acetonitrile:water).

The product was dried in a vacuum oven (approximately 16-33 kPa at 55° C.) overnight to give the product as an off-white solid (76.0 g as a mixture of isomers, 92.0% yield).

The $^1$H NMR spectrum of the major isomer was identical to the spectrum of the material prepared in Example 7, Step C.

Example 8

Preparation of methyl 4-[5-[3-chloro-5-(trifluoromethyl)phenyl]-4,5-dihydro-5-(trifluoromethyl)-3-isoxazolyl]-1-naphthalenecarboxylate Step A: Preparation of methyl 4-[3-[3-chloro-5-(trifluoromethyl)phenyl]-4,4,4-trifluoro-1-oxo-2-buten-1-yl]-1-naphthalenecarboxylate A mixture of methyl 4-acetyl-1-naphthalenecarboxylate (7.83 g, 34.3 mmol), 1-[3-chloro-5-(trifluoromethyl)phenyl]-2,2,2-trifluoroethanone (10.43 g, 37.71 mmol), calcium hydroxide (1.25 g, 16.9 mmol), N,N-dimethylformamide (27 mL) and tert-butyl methyl ether (44 mL) was heated to reflux. The tert-butyl methyl ether/water azeotrope was removed as described in Example 7, Step C. As the decanter trap contained an amount of tert-butyl methyl ether sufficient to dissolve all of the water formed by the reaction, the condensate in the trap did not separate into layers containing predominately water and predominately tert-butyl methyl ether. Tert-butyl methyl ether was removed by gradually draining the decanter trap until the reaction temperature was 85° C. To maintain this temperature, tert-butyl methyl ether was added as needed to compensate for loss of solvent from the apparatus. The total time from the start of heating the reaction mixture to stopping distillation was about 4.5 h.

The mixture was cooled to 25° C. and poured into a mixture of 0.5 N hydrochloric acid (100 mL) and tert-butyl methyl ether (50 mL). The mixture was acidified with concentrated hydrochloric acid and evaporated, and the residue was crystallized from hexanes (40 mL) to give the title product as a yellow solid (13.24 g, 79% yield) melting at 90-90.5° C. (after recrystallization from hexanes).

IR (nujol) 3071, 1721, 1710, 1671, 1516, 1439, 1316, 1280, 1252, 1178, 1129, 1103, 1026, 888, 861 cm$^{-1}$.

$^1$H NMR (CDCl$_3$): 8.77-8.73 (m, 1H), 8.28-8.25 (m, 1H), 8.0 (d, J=7.6 Hz, 1H), 7.67-7.60 (m, 3H), 7.40 (d, J=1.4 Hz, 1H), 7.32 (s, 1H), 7.23 (s, 1H), 7.20 (s, 1H), 4.02 (s, 3H).

Step B: Preparation of methyl 4-[5-[3-chloro-5-(trifluoromethyl)phenyl]-4,5-dihydro-5-(trifluoromethyl)-3-isoxazolyl]-1-naphthalenecarboxylate Aqueous sodium hydroxide (50%, 2.08 g, 25.5 mmol) was added dropwise to a stirred solution of hydroxylamine sulfate (1.07 g, 6.52 mmol) in water (20 mL) at 25° C. After this addition was complete the product of Example 8, Step A (5 g, 10.27 mmol) in tetrahydrofuran (20 mL) was added dropwise over 40 min. After the addition was complete the mixture was stirred further for 30 min. The organic phase was separated and added to hydrochloric acid (100 mL). The mixture was extracted with ethyl acetate (2×20 mL). The organic solvent was evaporated under reduced pressure. The residue was redissolved in acetic acid (16 mL) and then warmed to 100° C. Water (2 mL) was added dropwise, and the mixture was cooled to 50° C. The mixture was seeded with a small amount of previously prepared methyl 4-[5-[3-chloro-5-(trifluoromethyl)phenyl]-4,5-dihydro-5-(trifluoromethyl)-3-isoxazolyl]-1-naphthalenecarboxylate and then cooled to 25° C. Water (2 mL) was added and the mixture was cooled to 0° C. The mixture was filtered, and the solid was washed with acetic acid:water (8 mL:2 mL). The solid was dried in a vacuum oven to give the title product as a white solid (3.91 g, 76% yield) melting at 111.5-112° C. (after recrystallisation from acetonitrile).

IR (nujol) 1716, 1328, 1306, 1287, 1253, 1242, 1197, 1173, 1137, 1114, 1028, 771 cm$^{-1}$.

$^1$H NMR (CDCl$_3$): 8.90-8.87 (m, 1H), 8.82-8.79 (m, 1H), 8.10 (d, J=7.7 Hz), 7.87 (s, 1H), 7.81 (s, 1H), 7.72-7.67 (m, 3H) 7.55 (d, J=7.6 Hz, 1H), 4.34 (½ ABq, J=17.3 Hz, 1H), 4.03 (s, 3H), 3.93 (½ ABq, J=17.3 Hz, 1H).

The following Tables 1-8 identify specific combinations of reactants, intermediates and products illustrating the methods of the present invention. These tables specifically disclose compounds as well as particular transformations. In these tables: Et means ethyl, Me means methyl, CN means cyano, Ph means phenyl, Py means pyridinyl, c-Pr means cyclopropyl, i-Pr means isopropyl, n-Pr means normal propyl, s-Bu means secondary butyl, t-Bu means tertiary butyl, SMe means methylthio, S(O)$_2$ means sulfonyl and Thz means thiazole. Concatenations of groups are abbreviated similarly; for example, "S(O)$_2$Me" means methylsulfonyl.

Tables 1-6 relate to the method of Scheme 1 converting compounds of Formulae 2 and 3 to corresponding compounds of Formula 1. This transformation is believed to occur through the intermediacy of compounds of Formula 11.

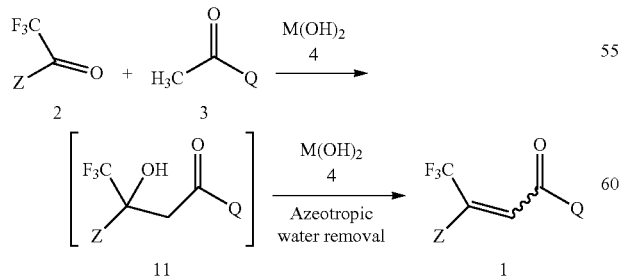

In the example transformations embodied in Tables 1-6, M is Ca, and water is distilled as an azeotrope from a reaction mixture comprising N,N-dimethylformamide as the polar aprotic solvent and tert-butyl methyl ether as the aprotic solvent capable of forming a low-boiling azeotrope with water.

TABLE 1

Z is (structure with R$^{2a}$, R$^{2b}$, R$^{2c}$); and Q is (naphthalene amide structure with N-R$^5$)

| R$^{2a}$ | R$^{2b}$ | R$^{2c}$ | R$^5$ |
| --- | --- | --- | --- |
| Cl | H | Cl | CH$_2$CH$_3$ |
| Cl | H | Cl | CH$_2$-i-Pr |
| Cl | H | Cl | CH$_2$CH$_2$Cl |
| Cl | H | Cl | CH$_2$CH$_2$OH |
| Cl | H | Cl | CH(Me)CH$_2$OH |
| Cl | H | Cl | CH$_2$CH(Me)OH |
| Cl | H | Cl | CH$_2$C(Me)$_2$OH |
| Cl | H | Cl | CH$_2$CH$_2$CH$_2$OH |
| Cl | H | Cl | CH$_2$C(Me)$_2$CH$_2$OH |
| Cl | H | Cl | CH$_2$CH$_2$CH(Me)OH |
| Cl | H | Cl | CH$_2$C(=O)N(H)Et |
| Cl | H | Cl | CH$_2$C(=O)N(H)-i-Pr |
| Cl | H | Cl | CH$_2$C(=O)N(H)CH$_2$-i-Pr |
| Cl | H | Cl | CH(Me)C(=O)N(H)CH$_2$-i-Pr |
| Cl | H | Cl | CH$_2$C(=O)N(H)CH$_2$CH$_2$Cl |
| Cl | H | Cl | CH(Me)C(=O)N(H)CH$_2$CH$_2$Cl |
| Cl | H | Cl | CH$_2$C(=O)N(H)CH$_2$CH$_2$F |
| Cl | H | Cl | CH(Me)C(=O)N(H)CH$_2$CH$_2$F |
| Cl | H | Cl | CH$_2$CF$_3$ |
| Cl | H | Cl | CH$_2$-(2-Py) |
| Cl | H | Cl | CH$_2$-(4-THz) |
| Cl | H | Cl | CH$_2$-c-Pr |
| Cl | H | Cl | CH$_2$CH$_2$SMe |
| Cl | H | Cl | CH(Me)CH$_2$SMe |
| Cl | H | Cl | CH$_2$CH$_2$CH$_2$SMe |
| Cl | H | Cl | CH$_2$CH$_2$S(=O)Me |
| Cl | H | Cl | CH(Me)CH$_2$S(=O)Me |
| Cl | H | Cl | CH$_2$CH$_2$CH$_2$S(=O)Me |
| Cl | H | Cl | CH$_2$CH$_2$S(O)$_2$Me |
| Cl | H | Cl | CH(Me)CH$_2$S(O)$_2$Me |
| Cl | H | Cl | CH$_2$CH$_2$CH$_2$S(O)$_2$Me |
| Cl | H | Cl | CH$_2$C(=O)N(H)CH$_2$CF$_3$ |
| Cl | H | Cl | CH(Me)C(=O)N(H)CH$_2$CF$_3$ |
| Cl | H | Cl | CH$_2$C(=O)N(H)CH$_2$CH$_2$SMe |
| Cl | H | Cl | CH$_2$C(=O)N(H)CH$_2$CH$_2$S(O)$_2$Me |
| Br | H | Br | CH$_2$CH$_3$ |
| Br | H | Br | CH$_2$-i-Pr |
| Br | H | Br | CH$_2$CH$_2$Cl |
| Br | H | Br | CH$_2$CH$_2$OH |
| Br | H | Br | CH(Me)CH$_2$OH |
| Br | H | Br | CH$_2$CH(Me)OH |
| Br | H | Br | CH$_2$C(Me)$_2$OH |
| Br | H | Br | CH$_2$CH$_2$CH$_2$OH |
| Br | H | Br | CH$_2$C(Me)$_2$CH$_2$OH |
| Br | H | Br | CH$_2$CH$_2$CH(Me)OH |
| Br | H | Br | CH$_2$C(=O)N(H)Et |
| Br | H | Br | CH$_2$C(=O)N(H)-i-Pr |
| Br | H | Br | CH$_2$C(=O)N(H)CH$_2$-i-Pr |
| Br | H | Br | CH(Me)C(=O)N(H)CH$_2$-i-Pr |
| Br | H | Br | CH$_2$C(=O)N(H)CH$_2$CH$_2$Cl |
| Br | H | Br | CH(Me)C(=O)N(H)CH$_2$CH$_2$Cl |
| Br | H | Br | CH$_2$C(=O)N(H)CH$_2$CH$_2$F |
| Br | H | Br | CH(Me)C(=O)N(H)CH$_2$CH$_2$F |
| Br | H | Br | CH$_2$CF$_3$ |
| Br | H | Br | CH$_2$-(2-Py) |
| Br | H | Br | CH$_2$-(4-THz) |
| Br | H | Br | CH$_2$-c-Pr |
| Br | H | Br | CH$_2$CH$_2$SMe |
| Br | H | Br | CH(Me)CH$_2$SMe |
| Br | H | Br | CH$_2$CH$_2$CH$_2$SMe |
| Br | H | Br | CH$_2$CH$_2$S(=O)Me |
| Br | H | Br | CH(Me)CH$_2$S(=O)Me |

TABLE 1-continued

Z is [structure with R²ᵃ, R²ᵇ, R²ᶜ on phenyl ring]; and Q is [4-methylnaphthalene-1-carboxamide with NHR⁵].

| R²ᵃ | R²ᵇ | R²ᶜ | R⁵ |
|---|---|---|---|
| Br | H | Br | CH₂CH₂CH₂S(=O)Me |
| Br | H | Br | CH₂CH₂S(O)₂Me |
| Br | H | Br | CH(Me)CH₂S(O)₂Me |
| Br | H | Br | CH₂CH₂CH₂S(O)₂Me |
| Br | H | Br | CH₂C(=O)N(H)CH₂CF₃ |
| Br | H | Br | CH(Me)C(=O)N(H)CH₂CF₃ |
| Br | H | Br | CH₂C(=O)N(H)CH₂CH₂SMe |
| Br | H | Br | CH₂C(=O)N(H)CH₂CH₂S(O)₂Me |
| CF₃ | H | H | CH₂CH₃ |
| CF₃ | H | H | CH₂-i-Pr |
| CF₃ | H | H | CH₂CH₂Cl |
| CF₃ | H | H | CH₂CH₂OH |
| CF₃ | H | H | CH(Me)CH₂OH |
| CF₃ | H | H | CH₂CH(Me)OH |
| CF₃ | H | H | CH₂C(Me)₂OH |
| CF₃ | H | H | CH₂CH₂CH₂OH |
| CF₃ | H | H | CH₂C(Me)₂CH₂OH |
| CF₃ | H | H | CH₂CH₂CH(Me)OH |
| CF₃ | H | H | CH₂C(=O)N(H)Et |
| CF₃ | H | H | CH₂C(=O)N(H)-i-Pr |
| CF₃ | H | H | CH₂C(=O)N(H)CH₂-i-Pr |
| CF₃ | H | H | CH(Me)C(=O)N(H)CH₂-i-Pr |
| CF₃ | H | H | CH₂C(=O)N(H)CH₂CH₂Cl |
| CF₃ | H | H | CH(Me)C(=O)N(H)CH₂CH₂Cl |
| CF₃ | H | H | CH₂C(=O)N(H)CH₂CH₂F |
| CF₃ | H | H | CH(Me)C(=O)N(H)CH₂CH₂F |
| CF₃ | H | H | CH₂CF₃ |
| CF₃ | H | H | CH₂-(2-Py) |
| CF₃ | H | H | CH₂-(4-THz) |
| CF₃ | H | H | CH₂-c-Pr |
| CF₃ | H | H | CH₂CH₂SMe |
| CF₃ | H | H | CH(Me)CH₂SMe |
| CF₃ | H | H | CH₂CH₂CH₂SMe |
| CF₃ | H | H | CH₂CH₂S(=O)Me |
| CF₃ | H | H | CH(Me)CH₂S(=O)Me |
| CF₃ | H | H | CH₂CH₂CH₂S(=O)Me |
| CF₃ | H | H | CH₂CH₂S(O)₂Me |
| CF₃ | H | H | CH(Me)CH₂S(O)₂Me |
| CF₃ | H | H | CH₂CH₂CH₂S(O)₂Me |
| CF₃ | H | H | CH₂C(=O)N(H)CH₂CF₃ |
| CF₃ | H | H | CH(Me)C(=O)N(H)CH₂CF₃ |
| CF₃ | H | H | CH₂C(=O)N(H)CH₂CH₂SMe |
| CF₃ | H | H | CH₂C(=O)N(H)CH₂CH₂S(O)₂Me |
| CF₃ | H | F | CH₂CH₃ |
| CF₃ | H | F | CH₂-i-Pr |
| CF₃ | H | F | CH₂CH₂Cl |
| CF₃ | H | F | CH₂CH₂OH |
| CF₃ | H | F | CH(Me)CH₂OH |
| CF₃ | H | F | CH₂CH(Me)OH |
| CF₃ | H | F | CH₂C(Me)₂OH |
| CF₃ | H | F | CH₂CH₂CH₂OH |
| CF₃ | H | F | CH₂C(Me)₂CH₂OH |
| CF₃ | H | F | CH₂CH₂CH(Me)OH |
| CF₃ | H | F | CH₂C(=O)N(H)Et |
| CF₃ | H | F | CH₂C(=O)N(H)-i-Pr |
| CF₃ | H | F | CH₂C(=O)N(H)CH₂-i-Pr |
| CF₃ | H | F | CH(Me)C(=O)N(H)CH₂-i-Pr |
| CF₃ | H | F | CH₂C(=O)N(H)CH₂CH₂Cl |
| CF₃ | H | F | CH(Me)C(=O)N(H)CH₂CH₂Cl |
| CF₃ | H | F | CH₂C(=O)N(H)CH₂CH₂F |
| CF₃ | H | F | CH(Me)C(=O)N(H)CH₂CH₂F |
| CF₃ | H | F | CH₂CF₃ |
| CF₃ | H | F | CH₂-(2-Py) |
| CF₃ | H | F | CH₂-(4-THz) |
| CF₃ | H | F | CH₂-c-Pr |
| CF₃ | H | F | CH₂CH₂SMe |
| CF₃ | H | F | CH(Me)CH₂SMe |
| CF₃ | H | F | CH₂CH₂CH₂SMe |
| CF₃ | H | F | CH₂CH₂S(=O)Me |
| CF₃ | H | F | CH(Me)CH₂S(=O)Me |
| CF₃ | H | F | CH₂CH₂CH₂S(=O)Me |
| CF₃ | H | F | CH₂CH₂S(O)₂Me |
| CF₃ | H | F | CH(Me)CH₂S(O)₂Me |
| CF₃ | H | F | CH₂CH₂CH₂S(O)₂Me |
| CF₃ | H | F | CH₂C(=O)N(H)CH₂CF₃ |
| CF₃ | H | F | CH(Me)C(=O)N(H)CH₂CF₃ |
| CF₃ | H | F | CH₂C(=O)N(H)CH₂CH₂SMe |
| CF₃ | H | F | CH₂C(=O)N(H)CH₂CH₂S(O)₂Me |
| CF₃ | H | Br | CH₂CH₃ |
| CF₃ | H | Br | CH₂-i-Pr |
| CF₃ | H | Br | CH₂CH₂Cl |
| CF₃ | H | Br | CH₂CH₂OH |
| CF₃ | H | Br | CH(Me)CH₂OH |
| CF₃ | H | Br | CH₂CH(Me)OH |
| CF₃ | H | Br | CH₂C(Me)₂OH |
| CF₃ | H | Br | CH₂CH₂CH₂OH |
| CF₃ | H | Br | CH₂C(Me)₂CH₂OH |
| CF₃ | H | Br | CH₂CH₂CH(Me)OH |
| CF₃ | H | Br | CH₂C(=O)N(H)Et |
| CF₃ | H | Br | CH₂C(=O)N(H)-i-Pr |
| CF₃ | H | Br | CH₂C(=O)N(H)CH₂-i-Pr |
| CF₃ | H | Br | CH(Me)C(=O)N(H)CH₂-i-Pr |
| CF₃ | H | Br | CH₂C(=O)N(H)CH₂CH₂Cl |
| CF₃ | H | Br | CH(Me)C(=O)N(H)CH₂CH₂Cl |
| CF₃ | H | Br | CH₂C(=O)N(H)CH₂CH₂F |
| CF₃ | H | Br | CH(Me)C(=O)N(H)CH₂CH₂F |
| CF₃ | H | Br | CH₂CF₃ |
| CF₃ | H | Br | CH₂-(2-Py) |
| CF₃ | H | Br | CH₂-(4-THz) |
| CF₃ | H | Br | CH₂-c-Pr |
| CF₃ | H | Br | CH₂CH₂SMe |
| CF₃ | H | Br | CH(Me)CH₂SMe |
| CF₃ | H | Br | CH₂CH₂CH₂SMe |
| CF₃ | H | Br | CH₂CH₂S(=O)Me |
| CF₃ | H | Br | CH(Me)CH₂S(=O)Me |
| CF₃ | H | Br | CH₂CH₂CH₂S(=O)Me |
| CF₃ | H | Br | CH₂CH₂S(O)₂Me |
| CF₃ | H | Br | CH(Me)CH₂S(O)₂Me |
| CF₃ | H | Br | CH₂CH₂CH₂S(O)₂Me |
| CF₃ | H | Br | CH₂C(=O)N(H)CH₂CF₃ |
| CF₃ | H | Br | CH(Me)C(=O)N(H)CH₂CF₃ |
| CF₃ | H | Br | CH₂C(=O)N(H)CH₂CH₂SMe |
| CF₃ | H | Br | CH₂C(=O)N(H)CH₂CH₂S(O)₂Me |
| CF₃ | H | Cl | CH₂CH₃ |
| CF₃ | H | Cl | CH₂-i-Pr |
| CF₃ | H | Cl | CH₂CH₂Cl |
| CF₃ | H | Cl | CH₂CH₂OH |
| CF₃ | H | Cl | CH(Me)CH₂OH |
| CF₃ | H | Cl | CH₂CH(Me)OH |
| CF₃ | H | Cl | CH₂C(Me)₂OH |
| CF₃ | H | Cl | CH₂CH₂CH₂OH |
| CF₃ | H | Cl | CH₂C(Me)₂CH₂OH |
| CF₃ | H | Cl | CH₂CH₂CH(Me)OH |
| CF₃ | H | Cl | CH₂C(=O)N(H)Et |
| CF₃ | H | Cl | CH₂C(=O)N(H)-i-Pr |
| CF₃ | H | Cl | CH₂C(=O)N(H)CH₂-i-Pr |
| CF₃ | H | Cl | CH(Me)C(=O)N(H)CH₂-i-Pr |
| CF₃ | H | Cl | CH₂C(=O)N(H)CH₂CH₂Cl |
| CF₃ | H | Cl | CH(Me)C(=O)N(H)CH₂CH₂Cl |
| CF₃ | H | Cl | CH₂C(=O)N(H)CH₂CH₂F |
| CF₃ | H | Cl | CH(Me)C(=O)N(H)CH₂CH₂F |
| CF₃ | H | Cl | CH₂CF₃ |
| CF₃ | H | Cl | CH₂-(2-Py) |
| CF₃ | H | Cl | CH₂-(4-THz) |

TABLE 1-continued

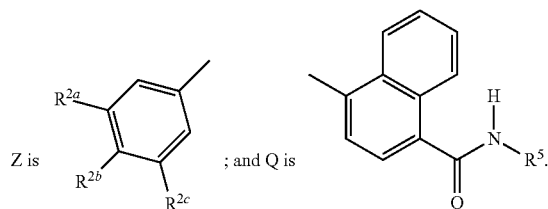

Z is ; and Q is

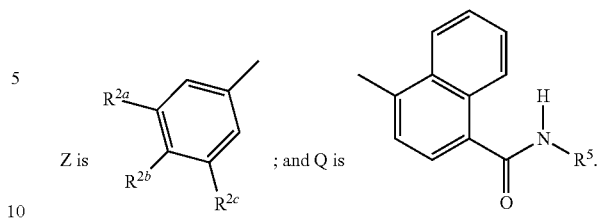

| $R^{2a}$ | $R^{2b}$ | $R^{2c}$ | $R^5$ |
|---|---|---|---|
| CF₃ | H | Cl | CH₂-c-Pr |
| CF₃ | H | Cl | CH₂CH₂SMe |
| CF₃ | H | Cl | CH(Me)CH₂SMe |
| CF₃ | H | Cl | CH₂CH₂CH₂SMe |
| CF₃ | H | Cl | CH₂CH₂S(=O)Me |
| CF₃ | H | Cl | CH(Me)CH₂S(=O)Me |
| CF₃ | H | Cl | CH₂CH₂CH₂S(=O)Me |
| CF₃ | H | Cl | CH₂CH₂S(O)₂Me |
| CF₃ | H | Cl | CH(Me)CH₂S(O)₂Me |
| CF₃ | H | Cl | CH₂CH₂CH₂S(O)₂Me |
| CF₃ | H | Cl | CH₂C(=O)N(H)CH₂CF₃ |
| CF₃ | H | Cl | CH(Me)C(=O)N(H)CH₂CF₃ |
| CF₃ | H | Cl | CH₂C(=O)N(H)CH₂CH₂SMe |
| CF₃ | H | Cl | CH₂C(=O)N(H)CH₂CH₂S(O)₂Me |
| CF₃ | H | CF₃ | CH₂CH₃ |
| CF₃ | H | CF₃ | CH₂-i-Pr |
| CF₃ | H | CF₃ | CH₂CH₂Cl |
| CF₃ | H | CF₃ | CH₂CH₂OH |
| CF₃ | H | CF₃ | CH(Me)CH₂OH |
| CF₃ | H | CF₃ | CH₂CH(Me)OH |
| CF₃ | H | CF₃ | CH₂C(Me)₂OH |
| CF₃ | H | CF₃ | CH₂CH₂CH₂OH |
| CF₃ | H | CF₃ | CH₂C(Me)₂CH₂OH |
| CF₃ | H | CF₃ | CH₂CH₂CH(Me)OH |
| CF₃ | H | CF₃ | CH₂C(=O)N(H)Et |
| CF₃ | H | CF₃ | CH₂C(=O)N(H)-i-Pr |
| CF₃ | H | CF₃ | CH₂C(=O)N(H)CH₂-i-Pr |
| CF₃ | H | CF₃ | CH(Me)C(=O)N(H)CH₂-i-Pr |
| CF₃ | H | CF₃ | CH₂C(=O)N(H)CH₂CH₂Cl |
| CF₃ | H | CF₃ | CH(Me)C(=O)N(H)CH₂CH₂Cl |
| CF₃ | H | CF₃ | CH₂C(=O)N(H)CH₂CH₂F |
| CF₃ | H | CF₃ | CH(Me)C(=O)N(H)CH₂CH₂F |
| CF₃ | H | CF₃ | CH₂CF₃ |
| CF₃ | H | CF₃ | CH₂-(2-Py) |
| CF₃ | H | CF₃ | CH₂-(4-THz) |
| CF₃ | H | CF₃ | CH₂-c-Pr |
| CF₃ | H | CF₃ | CH₂CH₂SMe |
| CF₃ | H | CF₃ | CH(Me)CH₂SMe |
| CF₃ | H | CF₃ | CH₂CH₂CH₂SMe |
| CF₃ | H | CF₃ | CH₂CH₂S(=O)Me |
| CF₃ | H | CF₃ | CH(Me)CH₂S(=O)Me |
| CF₃ | H | CF₃ | CH₂CH₂CH₂S(=O)Me |
| CF₃ | H | CF₃ | CH₂CH₂S(O)₂Me |
| CF₃ | H | CF₃ | CH(Me)CH₂S(O)₂Me |
| CF₃ | H | CF₃ | CH₂CH₂CH₂S(O)₂Me |
| CF₃ | H | CF₃ | CH₂C(=O)N(H)CH₂CF₃ |
| CF₃ | H | CF₃ | CH(Me)C(=O)N(H)CH₂CF₃ |
| CF₃ | H | CF₃ | CH₂C(=O)N(H)CH₂CH₂SMe |
| CF₃ | H | CF₃ | CH₂C(=O)N(H)CH₂CH₂S(O)₂Me |
| Cl | Cl | Cl | CH₂CH₃ |
| Cl | Cl | Cl | CH₂-i-Pr |
| Cl | Cl | Cl | CH₂CH₂Cl |
| Cl | Cl | Cl | CH₂CH₂OH |
| Cl | Cl | Cl | CH(Me)CH₂OH |
| Cl | Cl | Cl | CH₂CH(Me)OH |
| Cl | Cl | Cl | CH₂C(Me)₂OH |
| Cl | Cl | Cl | CH₂CH₂CH₂OH |
| Cl | Cl | Cl | CH₂C(Me)₂CH₂OH |
| Cl | Cl | Cl | CH₂CH₂CH(Me)OH |
| Cl | Cl | Cl | CH₂C(=O)N(H)Et |
| Cl | Cl | Cl | CH₂C(=O)N(H)-i-Pr |
| Cl | Cl | Cl | CH₂C(=O)N(H)CH₂-i-Pr |
| Cl | Cl | Cl | CH(Me)C(=O)N(H)CH₂-i-Pr |
| Cl | Cl | Cl | CH₂C(=O)N(H)CH₂CH₂Cl |
| Cl | Cl | Cl | CH(Me)C(=O)N(H)CH₂CH₂Cl |
| Cl | Cl | Cl | CH₂C(=O)N(H)CH₂CH₂F |
| Cl | Cl | Cl | CH(Me)C(=O)N(H)CH₂CH₂F |
| Cl | Cl | Cl | CH₂CF₃ |
| Cl | Cl | Cl | CH₂-(2-Py) |
| Cl | Cl | Cl | CH₂-(4-THz) |
| Cl | Cl | Cl | CH₂-c-Pr |
| Cl | Cl | Cl | CH₂CH₂SMe |
| Cl | Cl | Cl | CH(Me)CH₂SMe |
| Cl | Cl | Cl | CH₂CH₂CH₂SMe |
| Cl | Cl | Cl | CH₂CH₂S(=O)Me |
| Cl | Cl | Cl | CH(Me)CH₂S(=O)Me |
| Cl | Cl | Cl | CH₂CH₂CH₂S(=O)Me |
| Cl | Cl | Cl | CH₂CH₂S(O)₂Me |
| Cl | Cl | Cl | CH(Me)CH₂S(O)₂Me |
| Cl | Cl | Cl | CH₂CH₂CH₂S(O)₂Me |
| Cl | Cl | Cl | CH₂C(=O)N(H)CH₂CF₃ |
| Cl | Cl | Cl | CH(Me)C(=O)N(H)CH₂CF₃ |
| Cl | Cl | Cl | CH₂C(=O)N(H)CH₂CH₂SMe |
| Cl | Cl | Cl | CH₂C(=O)N(H)CH₂CH₂S(O)₂Me |
| Cl | F | Cl | CH₂CH₃ |
| Cl | F | Cl | CH₂-i-Pr |
| Cl | F | Cl | CH₂CH₂Cl |
| Cl | F | Cl | CH₂CH₂OH |
| Cl | F | Cl | CH(Me)CH₂OH |
| Cl | F | Cl | CH₂CH(Me)OH |
| Cl | F | Cl | CH₂C(Me)₂OH |
| Cl | F | Cl | CH₂CH₂CH₂OH |
| Cl | F | Cl | CH₂C(Me)₂CH₂OH |
| Cl | F | Cl | CH₂CH₂CH(Me)OH |
| Cl | F | Cl | CH₂C(=O)N(H)Et |
| Cl | F | Cl | CH₂C(=O)N(H)-i-Pr |
| Cl | F | Cl | CH₂C(=O)N(H)CH₂-i-Pr |
| Cl | F | Cl | CH(Me)C(=O)N(H)CH₂-i-Pr |
| Cl | F | Cl | CH₂C(=O)N(H)CH₂CH₂Cl |
| Cl | F | Cl | CH(Me)C(=O)N(H)CH₂CH₂Cl |
| Cl | F | Cl | CH₂C(=O)N(H)CH₂CH₂F |
| Cl | F | Cl | CH(Me)C(=O)N(H)CH₂CH₂F |
| Cl | F | Cl | CH₂CF₃ |
| Cl | F | Cl | CH₂-(2-Py) |
| Cl | F | Cl | CH₂-(4-THz) |
| Cl | F | Cl | CH₂-c-Pr |
| Cl | F | Cl | CH₂CH₂SMe |
| Cl | F | Cl | CH(Me)CH₂SMe |
| Cl | F | Cl | CH₂CH₂CH₂SMe |
| Cl | F | Cl | CH₂CH₂S(=O)Me |
| Cl | F | Cl | CH(Me)CH₂S(=O)Me |
| Cl | F | Cl | CH₂CH₂CH₂S(=O)Me |
| Cl | F | Cl | CH₂CH₂S(O)₂Me |
| Cl | F | Cl | CH(Me)CH₂S(O)₂Me |
| Cl | F | Cl | CH₂CH₂CH₂S(O)₂Me |
| Cl | F | Cl | CH₂C(=O)N(H)CH₂CF₃ |
| Cl | F | Cl | CH(Me)C(=O)N(H)CH₂CF₃ |
| Cl | F | Cl | CH₂C(=O)N(H)CH₂CH₂SMe |
| Cl | F | Cl | CH₂C(=O)N(H)CH₂CH₂S(O)₂Me |
| OCF₃ | H | Cl | CH₂CH₃ |
| OCF₃ | H | Cl | CH₂-i-Pr |
| OCF₃ | H | Cl | CH₂CH₂Cl |
| OCF₃ | H | Cl | CH₂CH₂OH |
| OCF₃ | H | Cl | CH(Me)CH₂OH |
| OCF₃ | H | Cl | CH₂CH(Me)OH |
| OCF₃ | H | Cl | CH₂C(Me)₂OH |
| OCF₃ | H | Cl | CH₂CH₂CH₂OH |
| OCF₃ | H | Cl | CH₂C(Me)₂CH₂OH |
| OCF₃ | H | Cl | CH₂CH₂CH(Me)OH |
| OCF₃ | H | Cl | CH₂C(=O)N(H)Et |
| OCF₃ | H | Cl | CH₂C(=O)N(H)-i-Pr |
| OCF₃ | H | Cl | CH₂C(=O)N(H)CH₂-i-Pr |
| OCF₃ | H | Cl | CH(Me)C(=O)N(H)CH₂-i-Pr |
| OCF₃ | H | Cl | CH₂C(=O)N(H)CH₂CH₂Cl |

TABLE 1-continued

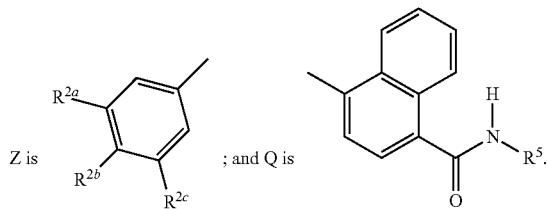

| $R^{2a}$ | $R^{2b}$ | $R^{2c}$ | $R^5$ |
|---|---|---|---|
| OCF$_3$ | H | Cl | CH(Me)C(=O)N(H)CH$_2$CH$_2$Cl |
| OCF$_3$ | H | Cl | CH$_2$C(=O)N(H)CH$_2$CH$_2$F |
| OCF$_3$ | H | Cl | CH(Me)C(=O)N(H)CH$_2$CH$_2$F |
| OCF$_3$ | H | Cl | CH$_2$CF$_3$ |
| OCF$_3$ | H | Cl | CH$_2$-(2-Py) |
| OCF$_3$ | H | Cl | CH$_2$-(4-THz) |
| OCF$_3$ | H | Cl | CH$_2$-c-Pr |
| OCF$_3$ | H | Cl | CH$_2$CH$_2$SMe |
| OCF$_3$ | H | Cl | CH(Me)CH$_2$SMe |
| OCF$_3$ | H | Cl | CH$_2$CH$_2$CH$_2$SMe |
| OCF$_3$ | H | Cl | CH$_2$CH$_2$S(=O)Me |
| OCF$_3$ | H | Cl | CH(Me)CH$_2$S(=O)Me |
| OCF$_3$ | H | Cl | CH$_2$CH$_2$CH$_2$S(=O)Me |
| OCF$_3$ | H | Cl | CH$_2$CH$_2$S(O)$_2$Me |
| OCF$_3$ | H | Cl | CH(Me)CH$_2$S(O)$_2$Me |
| OCF$_3$ | H | Cl | CH$_2$CH$_2$CH$_2$S(O)$_2$Me |
| OCF$_3$ | H | Cl | CH$_2$C(=O)N(H)CH$_2$CF$_3$ |
| OCF$_3$ | H | Cl | CH(Me)C(=O)N(H)CH$_2$CF$_3$ |
| OCF$_3$ | H | Cl | CH$_2$C(=O)N(H)CH$_2$CH$_2$SMe |
| OCF$_3$ | H | Cl | CH$_2$C(=O)N(H)CH$_2$CH$_2$S(O)$_2$Me |

TABLE 2

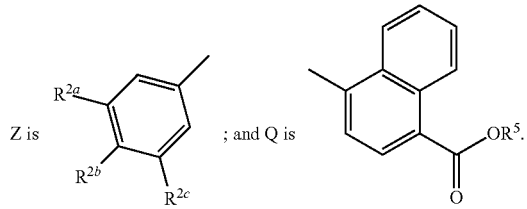

| $R^{2a}$ | $R^{2b}$ | $R^{2c}$ | $R^5$ |
|---|---|---|---|
| Cl | H | Cl | CH$_3$ |
| Cl | H | Cl | CH$_2$CH$_3$ |
| Cl | H | Cl | CH$_2$-i-Pr |
| Cl | H | Cl | n-Pr |
| Cl | H | Cl | i-Pr |
| Cl | H | Cl | s-Bu |
| Cl | H | Cl | i-Bu |
| Cl | H | Cl | (CH$_2$)$_5$CH$_3$ |
| Cl | H | Cl | CH$_2$Ph |
| Br | H | Br | CH$_3$ |
| Br | H | Br | CH$_2$CH$_3$ |
| Br | H | Br | CH$_2$-i-Pr |
| Br | H | Br | n-Pr |
| Br | H | Br | i-Pr |
| Br | H | Br | s-Bu |
| Br | H | Br | i-Bu |
| Br | H | Br | (CH$_2$)$_5$CH$_3$ |
| Br | H | Br | CH$_2$Ph |
| CF$_3$ | H | H | CH$_3$ |
| CF$_3$ | H | H | CH$_2$CH$_3$ |
| CF$_3$ | H | H | CH$_2$-i-Pr |
| CF$_3$ | H | H | n-Pr |
| CF$_3$ | H | H | i-Pr |
| CF$_3$ | H | H | s-Bu |
| CF$_3$ | H | H | i-Bu |
| CF$_3$ | H | H | (CH$_2$)$_5$CH$_3$ |
| CF$_3$ | H | H | CH$_2$Ph |
| CF$_3$ | H | F | CH$_3$ |
| CF$_3$ | H | F | CH$_2$CH$_3$ |

TABLE 2-continued

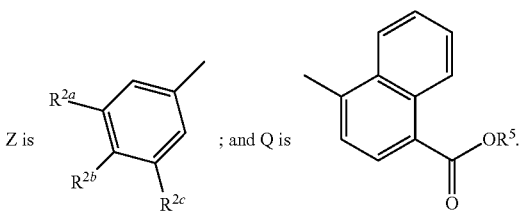

| $R^{2a}$ | $R^{2b}$ | $R^{2c}$ | $R^5$ |
|---|---|---|---|
| CF$_3$ | H | F | CH$_2$-i-Pr |
| CF$_3$ | H | F | n-Pr |
| CF$_3$ | H | F | i-Pr |
| CF$_3$ | H | F | s-Bu |
| CF$_3$ | H | F | i-Bu |
| CF$_3$ | H | F | (CH$_2$)$_5$CH$_3$ |
| CF$_3$ | H | F | CH$_2$Ph |
| CF$_3$ | H | Br | CH$_3$ |
| CF$_3$ | H | Br | CH$_2$CH$_3$ |
| CF$_3$ | H | Br | CH$_2$-i-Pr |
| CF$_3$ | H | Br | n-Pr |
| CF$_3$ | H | Br | i-Pr |
| CF$_3$ | H | Br | s-Bu |
| CF$_3$ | H | Br | i-Bu |
| CF$_3$ | H | Br | (CH$_2$)$_5$CH$_3$ |
| CF$_3$ | H | Br | CH$_2$Ph |
| CF$_3$ | H | Cl | CH$_3$ |
| CF$_3$ | H | Cl | CH$_2$CH$_3$ |
| CF$_3$ | H | Cl | CH$_2$-i-Pr |
| CF$_3$ | H | Cl | n-Pr |
| CF$_3$ | H | Cl | i-Pr |
| CF$_3$ | H | Cl | s-Bu |
| CF$_3$ | H | Cl | i-Bu |
| CF$_3$ | H | Cl | (CH$_2$)$_5$CH$_3$ |
| CF$_3$ | H | Cl | CH$_2$Ph |
| CF$_3$ | H | CF$_3$ | CH$_3$ |
| CF$_3$ | H | CF$_3$ | CH$_2$CH$_3$ |
| CF$_3$ | H | CF$_3$ | CH$_2$-i-Pr |
| CF$_3$ | H | CF$_3$ | n-Pr |
| CF$_3$ | H | CF$_3$ | i-Pr |
| CF$_3$ | H | CF$_3$ | s-Bu |
| CF$_3$ | H | CF$_3$ | i-Bu |
| CF$_3$ | H | CF$_3$ | (CH$_2$)$_5$CH$_3$ |
| CF$_3$ | H | CF$_3$ | CH$_2$Ph |
| Cl | Cl | Cl | CH$_3$ |
| Cl | Cl | Cl | CH$_2$CH$_3$ |
| Cl | Cl | Cl | CH$_2$-i-Pr |
| Cl | Cl | Cl | n-Pr |
| Cl | Cl | Cl | i-Pr |
| Cl | Cl | Cl | s-Bu |
| Cl | Cl | Cl | i-Bu |
| Cl | Cl | Cl | (CH$_2$)$_5$CH$_3$ |
| Cl | Cl | Cl | CH$_2$Ph |
| Cl | F | Cl | CH$_3$ |
| Cl | F | Cl | CH$_2$CH$_3$ |
| Cl | F | Cl | CH$_2$-i-Pr |
| Cl | F | Cl | n-Pr |
| Cl | F | Cl | i-Pr |
| Cl | F | Cl | s-Bu |
| Cl | F | Cl | i-Bu |
| Cl | F | Cl | (CH$_2$)$_5$CH$_3$ |
| Cl | F | Cl | CH$_2$Ph |
| OCF$_3$ | H | Cl | CH$_3$ |
| OCF$_3$ | H | Cl | CH$_2$CH$_3$ |
| OCF$_3$ | H | Cl | CH$_2$-i-Pr |
| OCF$_3$ | H | Cl | n-Pr |
| OCF$_3$ | H | Cl | i-Pr |
| OCF$_3$ | H | Cl | s-Bu |
| OCF$_3$ | H | Cl | i-Bu |
| OCF$_3$ | H | Cl | (CH$_2$)$_5$CH$_3$ |
| OCF$_3$ | H | Cl | CH$_2$Ph |

TABLE 3

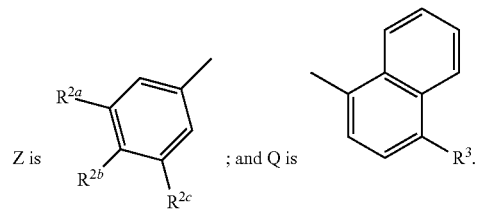

Z is 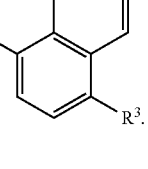 ; and Q is 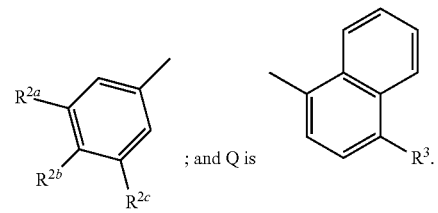 .

| $R^{2a}$ | $R^{2b}$ | $R^{2c}$ | $R^3$ |
|---|---|---|---|
| Cl | H | Cl | Cl |
| Cl | H | Cl | Br |
| Cl | H | Cl | I |
| Cl | H | Cl | OH |
| Cl | H | Cl | OMe |
| Cl | H | Cl | $OS(O)_2CF_3$ |
| Cl | H | Cl | nitro |
| Cl | H | Cl | $NH_2$ |
| Cl | H | Cl | cyano |
| Cl | H | Cl | Me |
| Cl | H | Cl | $CH_2Cl$ |
| Cl | H | Cl | $CH_2Br$ |
| Cl | H | Cl | $CH_2OH$ |
| Cl | H | Cl | $CH_2OC(O)Me$ |
| Cl | H | Cl | $CO_2H$ |
| Cl | H | Cl | n-Pr |
| Br | H | Br | Cl |
| Br | H | Br | Br |
| Br | H | Br | I |
| Br | H | Br | OH |
| Br | H | Br | OMe |
| Br | H | Br | $OS(O)_2CF_3$ |
| Br | H | Br | nitro |
| Br | H | Br | $NH_2$ |
| Br | H | Br | cyano |
| Br | H | Br | Me |
| Br | H | Br | $CH_2Cl$ |
| Br | H | Br | $CH_2Br$ |
| Br | H | Br | $CH_2OH$ |
| Br | H | Br | $CH_2OC(O)Me$ |
| Br | H | Br | $CO_2H$ |
| Br | H | Br | n-Pr |
| $CF_3$ | H | H | Cl |
| $CF_3$ | H | H | Br |
| $CF_3$ | H | H | I |
| $CF_3$ | H | H | OH |
| $CF_3$ | H | H | OMe |
| $CF_3$ | H | H | $OS(O)_2CF_3$ |
| $CF_3$ | H | H | nitro |
| $CF_3$ | H | H | $NH_2$ |
| $CF_3$ | H | H | cyano |
| $CF_3$ | H | H | Me |
| $CF_3$ | H | H | $CH_2Cl$ |
| $CF_3$ | H | H | $CH_2Br$ |
| $CF_3$ | H | H | $CH_2OH$ |
| $CF_3$ | H | H | $CH_2OC(O)Me$ |
| $CF_3$ | H | H | $CO_2H$ |
| $CF_3$ | H | H | n-Pr |
| $CF_3$ | H | F | Cl |
| $CF_3$ | H | F | Br |
| $CF_3$ | H | F | I |
| $CF_3$ | H | F | OH |
| $CF_3$ | H | F | OMe |
| $CF_3$ | H | F | $OS(O)_2CF_3$ |
| $CF_3$ | H | F | nitro |
| $CF_3$ | H | F | $NH_2$ |
| $CF_3$ | H | F | cyano |
| $CF_3$ | H | F | Me |
| $CF_3$ | H | F | $CH_2Cl$ |
| $CF_3$ | H | F | $CH_2Br$ |
| $CF_3$ | H | F | $CH_2OH$ |
| $CF_3$ | H | F | $CH_2OC(O)Me$ |
| $CF_3$ | H | F | $CO_2H$ |
| $CF_3$ | H | F | n-Pr |
| $CF_3$ | H | Br | Cl |
| $CF_3$ | H | Br | Br |
| $CF_3$ | H | Br | I |
| $CF_3$ | H | Br | OH |
| $CF_3$ | H | Br | OMe |
| $CF_3$ | H | Br | $OS(O)_2CF_3$ |
| $CF_3$ | H | Br | nitro |
| $CF_3$ | H | Br | $NH_2$ |
| $CF_3$ | H | Br | cyano |
| $CF_3$ | H | Br | Me |
| $CF_3$ | H | Br | $CH_2Cl$ |
| $CF_3$ | H | Br | $CH_2Br$ |
| $CF_3$ | H | Br | $CH_2OH$ |
| $CF_3$ | H | Br | $CH_2OC(O)Me$ |
| $CF_3$ | H | Br | $CO_2H$ |
| $CF_3$ | H | Br | n-Pr |
| $CF_3$ | H | Cl | Cl |
| $CF_3$ | H | Cl | Br |
| $CF_3$ | H | Cl | I |
| $CF_3$ | H | Cl | OH |
| $CF_3$ | H | Cl | OMe |
| $CF_3$ | H | Cl | $OS(O)_2CF_3$ |
| $CF_3$ | H | Cl | nitro |
| $CF_3$ | H | Cl | $NH_2$ |
| $CF_3$ | H | Cl | cyano |
| $CF_3$ | H | Cl | Me |
| $CF_3$ | H | Cl | $CH_2Cl$ |
| $CF_3$ | H | Cl | $CH_2Br$ |
| $CF_3$ | H | Cl | $CH_2OH$ |
| $CF_3$ | H | Cl | $CH_2OC(O)Me$ |
| $CF_3$ | H | Cl | $CO_2H$ |
| $CF_3$ | H | Cl | n-Pr |
| $CF_3$ | H | $CF_3$ | Cl |
| $CF_3$ | H | $CF_3$ | Br |
| $CF_3$ | H | $CF_3$ | I |
| $CF_3$ | H | $CF_3$ | OH |
| $CF_3$ | H | $CF_3$ | OMe |
| $CF_3$ | H | $CF_3$ | $OS(O)_2CF_3$ |
| $CF_3$ | H | $CF_3$ | nitro |
| $CF_3$ | H | $CF_3$ | $NH_2$ |
| $CF_3$ | H | $CF_3$ | cyano |
| $CF_3$ | H | $CF_3$ | Me |
| $CF_3$ | H | $CF_3$ | $CH_2Cl$ |
| $CF_3$ | H | $CF_3$ | $CH_2Br$ |
| $CF_3$ | H | $CF_3$ | $CH_2OH$ |
| $CF_3$ | H | $CF_3$ | $CH_2OC(O)Me$ |
| $CF_3$ | H | $CF_3$ | $CO_2H$ |
| $CF_3$ | H | $CF_3$ | n-Pr |
| Cl | Cl | Cl | Cl |
| Cl | Cl | Cl | Br |
| Cl | Cl | Cl | I |
| Cl | Cl | Cl | OH |
| Cl | Cl | Cl | OMe |
| Cl | Cl | Cl | $OS(O)_2CF_3$ |
| Cl | Cl | Cl | nitro |
| Cl | Cl | Cl | $NH_2$ |
| Cl | Cl | Cl | cyano |
| Cl | Cl | Cl | Me |
| Cl | Cl | Cl | $CH_2Cl$ |
| Cl | Cl | Cl | $CH_2Br$ |
| Cl | Cl | Cl | $CH_2OH$ |
| Cl | Cl | Cl | $CH_2OC(O)Me$ |
| Cl | Cl | Cl | $CO_2H$ |
| Cl | Cl | Cl | n-Pr |
| Cl | F | Cl | Cl |
| Cl | F | Cl | Br |
| Cl | F | Cl | I |
| Cl | F | Cl | OH |
| Cl | F | Cl | OMe |
| Cl | F | Cl | $OS(O)_2CF_3$ |

TABLE 3-continued

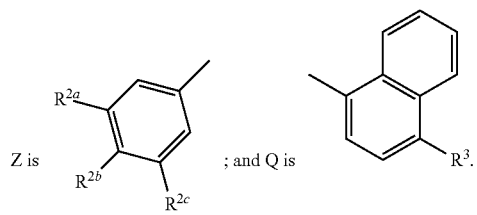

Z is ; and Q is .

| R2a | R2b | R2c | R3 |
|---|---|---|---|
| Cl | F | Cl | nitro |
| Cl | F | Cl | NH2 |
| Cl | F | Cl | cyano |
| Cl | F | Cl | Me |
| Cl | F | Cl | CH2Cl |
| Cl | F | Cl | CH2Br |
| Cl | F | Cl | CH2OH |
| Cl | F | Cl | CH2OC(O)Me |
| Cl | F | Cl | CO2H |
| Cl | F | Cl | n-Pr |
| OCF3 | H | Cl | Cl |
| OCF3 | H | Cl | Br |
| OCF3 | H | Cl | I |
| OCF3 | H | Cl | OH |
| OCF3 | H | Cl | OMe |
| OCF3 | H | Cl | OS(O)2CF3 |
| OCF3 | H | Cl | nitro |
| OCF3 | H | Cl | NH2 |
| OCF3 | H | Cl | cyano |
| OCF3 | H | Cl | Me |
| OCF3 | H | Cl | CH2Cl |
| OCF3 | H | Cl | CH2Br |
| OCF3 | H | Cl | CH2OH |
| OCF3 | H | Cl | CH2OC(O)Me |
| OCF3 | H | Cl | CO2H |
| OCF3 | H | Cl | n-Pr |

TABLE 4

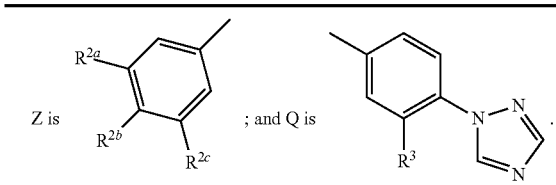

Z is ; and Q is .

| R2a | R2b | R2c | R1 | R3 |
|---|---|---|---|---|
| Cl | H | Cl | CF3 | H |
| Cl | H | Cl | CF3 | Me |
| Cl | Cl | CN | CF3 | CN |
| CF3 | H | H | CF3 | H |
| CF3 | H | Me | CF3 | Me |
| CF3 | H | H | CF3 | CN |
| CF3 | H | Cl | CF3 | H |
| CF3 | H | Cl | CF3 | Me |
| CF3 | H | Cl | CF3 | CN |
| Cl | Cl | Cl | CF3 | H |
| Cl | Cl | Cl | CF3 | CN |
| Cl | Cl | Cl | CF3 | Me |
| Cl | H | Cl | CF2Cl | H |
| Cl | H | Cl | CF2Cl | CN |
| Cl | H | Cl | CCl2F | H |
| Cl | H | Cl | CCl2F | CN |
| Br | H | Br | CF3 | H |
| Br | H | Br | CF3 | Me |
| Br | H | Br | CF3 | CN |
| CF3 | H | F | CF3 | H |
| CF3 | H | F | CF3 | Me |
| CF3 | H | F | CF3 | CN |
| CF3 | H | CF3 | CF3 | H |
| CF3 | H | CF3 | CF3 | Me |
| CF3 | H | CF3 | CF3 | CN |

TABLE 4-continued

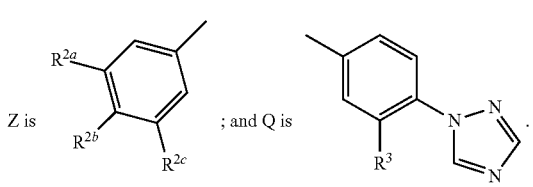

Z is ; and Q is .

| R2a | R2b | R2c | R1 | R3 |
|---|---|---|---|---|
| Cl | F | Cl | CF3 | H |
| Cl | F | Cl | CF3 | CN |
| Cl | F | Cl | CF3 | Me |
| Cl | H | Cl | CF2CF2H | H |
| Cl | H | Cl | CF2CF2H | CN |
| Cl | H | Cl | CF2CF3 | H |
| Cl | H | Cl | CF2CF3 | CN |

TABLE 5

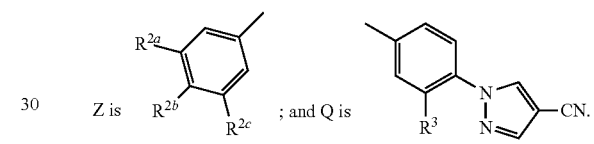

Z is ; and Q is .

| R2a | R2b | R2c | R1 | R3 |
|---|---|---|---|---|
| Cl | H | Cl | CF3 | H |
| Cl | H | Cl | CF3 | Me |
| Cl | Cl | CN | CF3 | CN |
| CF3 | H | H | CF3 | H |
| CF3 | H | Me | CF3 | Me |
| CF3 | H | H | CF3 | CN |
| CF3 | H | Cl | CF3 | H |
| CF3 | H | Cl | CF3 | Me |
| CF3 | H | Cl | CF3 | CN |
| Cl | Cl | Cl | CF3 | H |
| Cl | Cl | Cl | CF3 | CN |
| Cl | Cl | Cl | CF3 | Me |
| Cl | H | Cl | CF2Cl | H |
| Cl | H | Cl | CF2Cl | CN |
| Cl | H | Cl | CCl2F | H |
| Cl | H | Cl | CCl2F | CN |
| Br | H | Br | CF3 | H |
| Br | H | Br | CF3 | Me |
| Br | H | Br | CF3 | CN |
| CF3 | H | F | CF3 | H |
| CF3 | H | F | CF3 | Me |
| CF3 | H | F | CF3 | CN |
| CF3 | H | CF3 | CF3 | H |
| CF3 | H | CF3 | CF3 | Me |
| CF3 | H | CF3 | CF3 | CN |
| Cl | F | Cl | CF3 | H |
| Cl | F | Cl | CF3 | CN |
| Cl | F | Cl | CF3 | Me |
| Cl | H | Cl | CF2CF2H | H |
| Cl | H | Cl | CF2CF2H | CN |
| Cl | H | Cl | CF2CF3 | H |
| Cl | H | Cl | CF2CF3 | CN |

TABLE 6

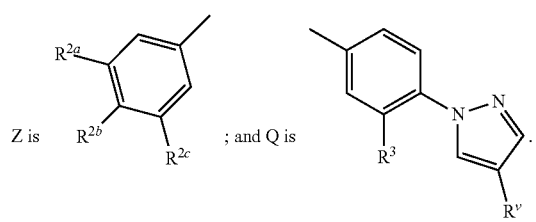

| R²ᵃ | R²ᵇ | R²ᶜ | Rᵛ | R³ |
|---|---|---|---|---|
| Cl | H | Cl | Br | H |
| Cl | H | Cl | Br | Me |
| Cl | Cl | Cl | Br | CN |
| CF₃ | H | H | Br | H |
| CF₃ | H | H | Br | Me |
| CF₃ | H | H | Br | CN |
| CF₃ | H | Cl | Br | H |
| CF₃ | H | Cl | Br | Me |
| CF₃ | H | Cl | Br | CN |
| Cl | Cl | Cl | Br | H |
| Cl | Cl | Cl | Br | CN |
| Cl | Cl | Cl | Br | Me |
| Br | H | Br | Br | H |
| Br | H | Br | Br | Me |
| Br | H | Br | Br | CN |
| CF₃ | H | F | Br | H |
| CF₃ | H | F | Br | Me |
| CF₃ | H | F | Br | CN |
| CF₃ | H | CF₃ | Br | H |
| CF₃ | H | CF₃ | Br | Me |
| CF₃ | H | CF₃ | Br | CN |
| Cl | F | Cl | Br | H |
| Cl | F | Cl | Br | CN |
| Cl | F | Cl | Br | Me |

Tables 7-9 relate to the method of Scheme 1a converting compounds of Formulae 2 and 3 to corresponding compounds of Formula 1. This transformation is believed to occur through the intermediacy of compounds of Formula 11.

Scheme 1a

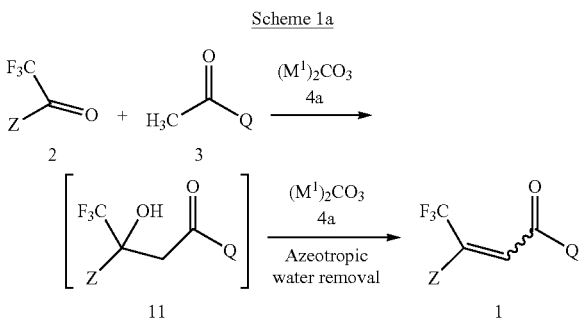

In the example transformations embodied in Tables 7-9, M¹ is K (i.e. the base is potassium carbonate), and water is distilled as an azeotrope from a reaction mixture comprising acetonitrile as the aprotic solvent capable of forming a low-boiling azeotrope with water.

TABLE 7

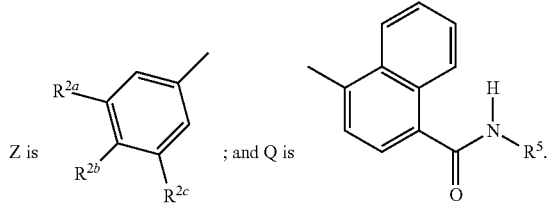

| R²ᵃ | R²ᵇ | R²ᶜ | R⁵ |
|---|---|---|---|
| Cl | H | Cl | CH₂CH₃ |
| Cl | H | Cl | CH₂-i-Pr |
| Cl | H | Cl | CH₂CH₂Cl |
| Cl | H | Cl | CH₂CH₂OH |
| Cl | H | Cl | CH(Me)CH₂OH |
| Cl | H | Cl | CH₂CH(Me)OH |
| Cl | H | Cl | CH₂C(Me)₂OH |
| Cl | H | Cl | CH₂CH₂CH₂OH |
| Cl | H | Cl | CH₂C(Me)₂CH₂OH |
| Cl | H | Cl | CH₂CH₂CH(Me)OH |
| Cl | H | Cl | CH₂C(=O)N(H)Et |
| Cl | H | Cl | CH₂C(=O)N(H)-i-Pr |
| Cl | H | Cl | CH₂C(=O)N(H)CH₂-i-Pr |
| Cl | H | Cl | CH(Me)C(=O)N(H)CH₂-i-Pr |
| Cl | H | Cl | CH₂C(=O)N(H)CH₂CH₂Cl |
| Cl | H | Cl | CH(Me)C(=O)N(H)CH₂CH₂Cl |
| Cl | H | Cl | CH₂C(=O)N(H)CH₂CH₂F |
| Cl | H | Cl | CH(Me)C(=O)N(H)CH₂CH₂F |
| Cl | H | Cl | CH₂CF₃ |
| Cl | H | Cl | CH₂-(2-Py) |
| Cl | H | Cl | CH₂-(4-THz) |
| Cl | H | Cl | CH₂-c-Pr |
| Cl | H | Cl | CH₂CH₂SMe |
| Cl | H | Cl | CH(Me)CH₂SMe |
| Cl | H | Cl | CH₂CH₂CH₂SMe |
| Cl | H | Cl | CH₂CH₂S(=O)Me |
| Cl | H | Cl | CH(Me)CH₂S(=O)Me |
| Cl | H | Cl | CH₂CH₂CH₂S(=O)Me |
| Cl | H | Cl | CH₂CH₂S(O)₂Me |
| Cl | H | Cl | CH(Me)CH₂S(O)₂Me |
| Cl | H | Cl | CH₂CH₂CH₂S(O)₂Me |
| Cl | H | Cl | CH₂C(=O)N(H)CH₂CF₃ |
| Cl | H | Cl | CH(Me)C(=O)N(H)CH₂CF₃ |
| Cl | H | Cl | CH₂C(=O)N(H)CH₂CH₂SMe |
| Cl | H | Cl | CH₂C(=O)N(H)CH₂CH₂S(O)₂Me |
| Br | H | Br | CH₂CH₃ |
| Br | H | Br | CH₂-i-Pr |
| Br | H | Br | CH₂CH₂Cl |
| Br | H | Br | CH₂CH₂OH |
| Br | H | Br | CH(Me)CH₂OH |
| Br | H | Br | CH₂CH(Me)OH |
| Br | H | Br | CH₂C(Me)₂OH |
| Br | H | Br | CH₂CH₂CH₂OH |
| Br | H | Br | CH₂C(Me)₂CH₂OH |
| Br | H | Br | CH₂CH₂CH(Me)OH |
| Br | H | Br | CH₂C(=O)N(H)Et |
| Br | H | Br | CH₂C(=O)N(H)-i-Pr |
| Br | H | Br | CH₂C(=O)N(H)CH₂-i-Pr |
| Br | H | Br | CH(Me)C(=O)N(H)CH₂-i-Pr |
| Br | H | Br | CH₂C(=O)N(H)CH₂CH₂Cl |
| Br | H | Br | CH(Me)C(=O)N(H)CH₂CH₂Cl |
| Br | H | Br | CH₂C(=O)N(H)CH₂CH₂F |
| Br | H | Br | CH(Me)C(=O)N(H)CH₂CH₂F |
| Br | H | Br | CH₂CF₃ |
| Br | H | Br | CH₂-(2-Py) |
| Br | H | Br | CH₂-(4-THz) |
| Br | H | Br | CH₂-c-Pr |
| Br | H | Br | CH₂CH₂SMe |
| Br | H | Br | CH(Me)CH₂SMe |
| Br | H | Br | CH₂CH₂CH₂SMe |
| Br | H | Br | CH₂CH₂S(=O)Me |
| Br | H | Br | CH(Me)CH₂S(=O)Me |
| Br | H | Br | CH₂CH₂CH₂S(=O)Me |
| Br | H | Br | CH₂CH₂S(O)₂Me |
| Br | H | Br | CH(Me)CH₂S(O)₂Me |
| Br | H | Br | CH₂CH₂CH₂S(O)₂Me |
| Br | H | Br | CH₂C(=O)N(H)CH₂CF₃ |

TABLE 7-continued

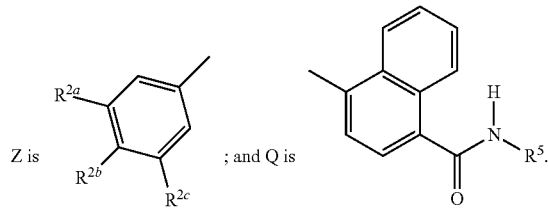

Z is (aryl with R2a, R2b, R2c); and Q is (4-methyl naphthamide with NHR5).

| R2a | R2b | R2c | R5 |
|---|---|---|---|
| Br | H | Br | CH(Me)C(=O)N(H)CH2CF3 |
| Br | H | Br | CH2C(=O)N(H)CH2CH2SMe |
| Br | H | Br | CH2C(=O)N(H)CH2CH2S(O)2Me |
| CF3 | H | H | CH2CH3 |
| CF3 | H | H | CH2-i-Pr |
| CF3 | H | H | CH2CH2Cl |
| CF3 | H | H | CH2CH2OH |
| CF3 | H | H | CH(Me)CH2OH |
| CF3 | H | H | CH2CH(Me)OH |
| CF3 | H | H | CH2C(Me)2OH |
| CF3 | H | H | CH2CH2CH2OH |
| CF3 | H | H | CH2C(Me)2CH2OH |
| CF3 | H | H | CH2CH2CH(Me)OH |
| CF3 | H | H | CH2C(=O)N(H)Et |
| CF3 | H | H | CH2C(=O)N(H)-i-Pr |
| CF3 | H | H | CH2C(=O)N(H)CH2-i-Pr |
| CF3 | H | H | CH(Me)C(=O)N(H)CH2-i-Pr |
| CF3 | H | H | CH2C(=O)N(H)CH2CH2Cl |
| CF3 | H | H | CH(Me)C(=O)N(H)CH2CH2Cl |
| CF3 | H | H | CH2C(=O)N(H)CH2CH2F |
| CF3 | H | H | CH(Me)C(=O)N(H)CH2CH2F |
| CF3 | H | H | CH2CF3 |
| CF3 | H | H | CH2-(2-Py) |
| CF3 | H | H | CH2-(4-THz) |
| CF3 | H | H | CH2-c-Pr |
| CF3 | H | H | CH2CH2SMe |
| CF3 | H | H | CH(Me)CH2SMe |
| CF3 | H | H | CH2CH2CH2SMe |
| CF3 | H | H | CH2CH2S(=O)Me |
| CF3 | H | H | CH(Me)CH2S(=O)Me |
| CF3 | H | H | CH2CH2CH2S(=O)Me |
| CF3 | H | H | CH2CH2S(O)2Me |
| CF3 | H | H | CH(Me)CH2S(O)2Me |
| CF3 | H | H | CH2CH2CH2S(O)2Me |
| CF3 | H | H | CH2C(=O)N(H)CH2CF3 |
| CF3 | H | H | CH(Me)C(=O)N(H)CH2CF3 |
| CF3 | H | H | CH2C(=O)N(H)CH2CH2SMe |
| CF3 | H | H | CH2C(=O)N(H)CH2CH2S(O)2Me |
| CF3 | H | F | CH2CH3 |
| CF3 | H | F | CH2-i-Pr |
| CF3 | H | F | CH2CH2Cl |
| CF3 | H | F | CH2CH2OH |
| CF3 | H | F | CH(Me)CH2OH |
| CF3 | H | F | CH2CH(Me)OH |
| CF3 | H | F | CH2C(Me)2OH |
| CF3 | H | F | CH2CH2CH2OH |
| CF3 | H | F | CH2C(Me)2CH2OH |
| CF3 | H | F | CH2CH2CH(Me)OH |
| CF3 | H | F | CH2C(=O)N(H)Et |
| CF3 | H | F | CH2C(=O)N(H)-i-Pr |
| CF3 | H | F | CH2C(=O)N(H)CH2-i-Pr |
| CF3 | H | F | CH(Me)C(=O)N(H)CH2-i-Pr |
| CF3 | H | F | CH2C(=O)N(H)CH2CH2Cl |
| CF3 | H | F | CH(Me)C(=O)N(H)CH2CH2Cl |
| CF3 | H | F | CH2C(=O)N(H)CH2CH2F |
| CF3 | H | F | CH(Me)C(=O)N(H)CH2CH2F |
| CF3 | H | F | CH2CF3 |
| CF3 | H | F | CH2-(2-Py) |
| CF3 | H | F | CH2-(4-THz) |
| CF3 | H | F | CH2-c-Pr |
| CF3 | H | F | CH2CH2SMe |
| CF3 | H | F | CH(Me)CH2SMe |
| CF3 | H | F | CH2CH2CH2SMe |
| CF3 | H | F | CH2CH2S(=O)Me |
| CF3 | H | F | CH(Me)CH2S(=O)Me |
| CF3 | H | F | CH2CH2CH2S(=O)Me |
| CF3 | H | F | CH2CH2S(O)2Me |
| CF3 | H | F | CH(Me)CH2S(O)2Me |
| CF3 | H | F | CH2CH2CH2S(O)2Me |
| CF3 | H | F | CH2C(=O)N(H)CH2CF3 |
| CF3 | H | F | CH(Me)C(=O)N(H)CH2CF3 |
| CF3 | H | F | CH2C(=O)N(H)CH2CH2SMe |
| CF3 | H | F | CH2C(=O)N(H)CH2CH2S(O)2Me |
| CF3 | H | Br | CH2CH3 |
| CF3 | H | Br | CH2-i-Pr |
| CF3 | H | Br | CH2CH2Cl |
| CF3 | H | Br | CH2CH2OH |
| CF3 | H | Br | CH(Me)CH2OH |
| CF3 | H | Br | CH2CH(Me)OH |
| CF3 | H | Br | CH2C(Me)2OH |
| CF3 | H | Br | CH2CH2CH2OH |
| CF3 | H | Br | CH2C(Me)2CH2OH |
| CF3 | H | Br | CH2CH2CH(Me)OH |
| CF3 | H | Br | CH2C(=O)N(H)Et |
| CF3 | H | Br | CH2C(=O)N(H)-i-Pr |
| CF3 | H | Br | CH2C(=O)N(H)CH2-i-Pr |
| CF3 | H | Br | CH(Me)C(=O)N(H)CH2-i-Pr |
| CF3 | H | Br | CH2C(=O)N(H)CH2CH2Cl |
| CF3 | H | Br | CH(Me)C(=O)N(H)CH2CH2Cl |
| CF3 | H | Br | CH2C(=O)N(H)CH2CH2F |
| CF3 | H | Br | CH(Me)C(=O)N(H)CH2CH2F |
| CF3 | H | Br | CH2CF3 |
| CF3 | H | Br | CH2-(2-Py) |
| CF3 | H | Br | CH2-(4-THz) |
| CF3 | H | Br | CH2-c-Pr |
| CF3 | H | Br | CH2CH2SMe |
| CF3 | H | Br | CH(Me)CH2SMe |
| CF3 | H | Br | CH2CH2CH2SMe |
| CF3 | H | Br | CH2CH2S(=O)Me |
| CF3 | H | Br | CH(Me)CH2S(=O)Me |
| CF3 | H | Br | CH2CH2CH2S(=O)Me |
| CF3 | H | Br | CH2CH2S(O)2Me |
| CF3 | H | Br | CH(Me)CH2S(O)2Me |
| CF3 | H | Br | CH2CH2CH2S(O)2Me |
| CF3 | H | Br | CH2C(=O)N(H)CH2CF3 |
| CF3 | H | Br | CH(Me)C(=O)N(H)CH2CF3 |
| CF3 | H | Br | CH2C(=O)N(H)CH2CH2SMe |
| CF3 | H | Br | CH2C(=O)N(H)CH2CH2S(O)2Me |
| CF3 | H | Cl | CH2CH3 |
| CF3 | H | Cl | CH2-i-Pr |
| CF3 | H | Cl | CH2CH2Cl |
| CF3 | H | Cl | CH2CH2OH |
| CF3 | H | Cl | CH(Me)CH2OH |
| CF3 | H | Cl | CH2CH(Me)OH |
| CF3 | H | Cl | CH2C(Me)2OH |
| CF3 | H | Cl | CH2CH2CH2OH |
| CF3 | H | Cl | CH2C(Me)2CH2OH |
| CF3 | H | Cl | CH2CH2CH(Me)OH |
| CF3 | H | Cl | CH2C(=O)N(H)Et |
| CF3 | H | Cl | CH2C(=O)N(H)-i-Pr |
| CF3 | H | Cl | CH2C(=O)N(H)CH2-i-Pr |
| CF3 | H | Cl | CH(Me)C(=O)N(H)CH2-i-Pr |
| CF3 | H | Cl | CH2C(=O)N(H)CH2CH2Cl |
| CF3 | H | Cl | CH(Me)C(=O)N(H)CH2CH2Cl |
| CF3 | H | Cl | CH2C(=O)N(H)CH2CH2F |
| CF3 | H | Cl | CH(Me)C(=O)N(H)CH2CH2F |
| CF3 | H | Cl | CH2CF3 |
| CF3 | H | Cl | CH2-(2-Py) |
| CF3 | H | Cl | CH2-(4-THz) |
| CF3 | H | Cl | CH2-c-Pr |
| CF3 | H | Cl | CH2CH2SMe |
| CF3 | H | Cl | CH(Me)CH2SMe |
| CF3 | H | Cl | CH2CH2CH2SMe |
| CF3 | H | Cl | CH2CH2S(=O)Me |

TABLE 7-continued

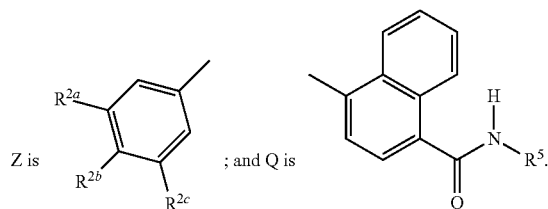

Z is ; and Q is

| $R^{2a}$ | $R^{2b}$ | $R^{2c}$ | $R^5$ |
|---|---|---|---|
| CF$_3$ | H | Cl | CH(Me)CH$_2$S(=O)Me |
| CF$_3$ | H | Cl | CH$_2$CH$_2$CH$_2$S(=O)Me |
| CF$_3$ | H | Cl | CH$_2$CH$_2$S(O)$_2$Me |
| CF$_3$ | H | Cl | CH(Me)CH$_2$S(O)$_2$Me |
| CF$_3$ | H | Cl | CH$_2$CH$_2$CH$_2$S(O)$_2$Me |
| CF$_3$ | H | Cl | CH$_2$C(=O)N(H)CH$_2$CF$_3$ |
| CF$_3$ | H | Cl | CH(Me)C(=O)N(H)CH$_2$CF$_3$ |
| CF$_3$ | H | Cl | CH$_2$C(=O)N(H)CH$_2$CH$_2$SMe |
| CF$_3$ | H | Cl | CH$_2$C(=O)N(H)CH$_2$CH$_2$S(O)$_2$Me |
| CF$_3$ | H | CF$_3$ | CH$_2$CH$_3$ |
| CF$_3$ | H | CF$_3$ | CH$_2$-i-Pr |
| CF$_3$ | H | CF$_3$ | CH$_2$CH$_2$Cl |
| CF$_3$ | H | CF$_3$ | CH$_2$CH$_2$OH |
| CF$_3$ | H | CF$_3$ | CH(Me)CH$_2$OH |
| CF$_3$ | H | CF$_3$ | CH$_2$CH(Me)OH |
| CF$_3$ | H | CF$_3$ | CH$_2$C(Me)$_2$OH |
| CF$_3$ | H | CF$_3$ | CH$_2$CH$_2$CH$_2$OH |
| CF$_3$ | H | CF$_3$ | CH$_2$C(Me)$_2$CH$_2$OH |
| CF$_3$ | H | CF$_3$ | CH$_2$CH$_2$CH(Me)OH |
| CF$_3$ | H | CF$_3$ | CH$_2$C(=O)N(H)Et |
| CF$_3$ | H | CF$_3$ | CH$_2$C(=O)N(H)-i-Pr |
| CF$_3$ | H | CF$_3$ | CH$_2$C(=O)N(H)CH$_2$-i-Pr |
| CF$_3$ | H | CF$_3$ | CH(Me)C(=O)N(H)CH$_2$-i-Pr |
| CF$_3$ | H | CF$_3$ | CH$_2$C(=O)N(H)CH$_2$CH$_2$Cl |
| CF$_3$ | H | CF$_3$ | CH(Me)C(=O)N(H)CH$_2$CH$_2$Cl |
| CF$_3$ | H | CF$_3$ | CH$_2$C(=O)N(H)CH$_2$CH$_2$F |
| CF$_3$ | H | CF$_3$ | CH(Me)C(=O)N(H)CH$_2$CH$_2$F |
| CF$_3$ | H | CF$_3$ | CH$_2$CF$_3$ |
| CF$_3$ | H | CF$_3$ | CH$_2$-(2-Py) |
| CF$_3$ | H | CF$_3$ | CH$_2$-(4-THz) |
| CF$_3$ | H | CF$_3$ | CH$_2$-c-Pr |
| CF$_3$ | H | CF$_3$ | CH$_2$CH$_2$SMe |
| CF$_3$ | H | CF$_3$ | CH(Me)CH$_2$SMe |
| CF$_3$ | H | CF$_3$ | CH$_2$CH$_2$CH$_2$SMe |
| CF$_3$ | H | CF$_3$ | CH$_2$CH$_2$S(=O)Me |
| CF$_3$ | H | CF$_3$ | CH(Me)CH$_2$S(=O)Me |
| CF$_3$ | H | CF$_3$ | CH$_2$CH$_2$CH$_2$S(=O)Me |
| CF$_3$ | H | CF$_3$ | CH$_2$CH$_2$S(O)$_2$Me |
| CF$_3$ | H | CF$_3$ | CH(Me)CH$_2$S(O)$_2$Me |
| CF$_3$ | H | CF$_3$ | CH$_2$CH$_2$CH$_2$S(O)$_2$Me |
| CF$_3$ | H | CF$_3$ | CH$_2$C(=O)N(H)CH$_2$CF$_3$ |
| CF$_3$ | H | CF$_3$ | CH(Me)C(=O)N(H)CH$_2$CF$_3$ |
| CF$_3$ | H | CF$_3$ | CH$_2$C(=O)N(H)CH$_2$CH$_2$SMe |
| CF$_3$ | H | CF$_3$ | CH$_2$C(=O)N(H)CH$_2$CH$_2$S(O)$_2$Me |
| Cl | Cl | Cl | CH$_2$CH$_3$ |
| Cl | Cl | Cl | CH$_2$-i-Pr |
| Cl | Cl | Cl | CH$_2$CH$_2$Cl |
| Cl | Cl | Cl | CH$_2$CH$_2$OH |
| Cl | Cl | Cl | CH(Me)CH$_2$OH |
| Cl | Cl | Cl | CH$_2$CH(Me)OH |
| Cl | Cl | Cl | CH$_2$C(Me)$_2$OH |
| Cl | Cl | Cl | CH$_2$CH$_2$CH$_2$OH |
| Cl | Cl | Cl | CH$_2$C(Me)$_2$CH$_2$OH |
| Cl | Cl | Cl | CH$_2$CH$_2$CH(Me)OH |
| Cl | Cl | Cl | CH$_2$C(=O)N(H)Et |
| Cl | Cl | Cl | CH$_2$C(=O)N(H)-i-Pr |
| Cl | Cl | Cl | CH$_2$C(=O)N(H)CH$_2$-i-Pr |
| Cl | Cl | Cl | CH(Me)C(=O)N(H)CH$_2$-i-Pr |
| Cl | Cl | Cl | CH$_2$C(=O)N(H)CH$_2$CH$_2$Cl |
| Cl | Cl | Cl | CH(Me)C(=O)N(H)CH$_2$CH$_2$Cl |
| Cl | Cl | Cl | CH$_2$C(=O)N(H)CH$_2$CH$_2$F |
| Cl | Cl | Cl | CH(Me)C(=O)N(H)CH$_2$CH$_2$F |
| Cl | Cl | Cl | CH$_2$CF$_3$ |
| Cl | Cl | Cl | CH$_2$-(2-Py) |
| Cl | Cl | Cl | CH$_2$-(4-THz) |
| Cl | Cl | Cl | CH$_2$-c-Pr |
| Cl | Cl | Cl | CH$_2$CH$_2$SMe |

TABLE 7-continued

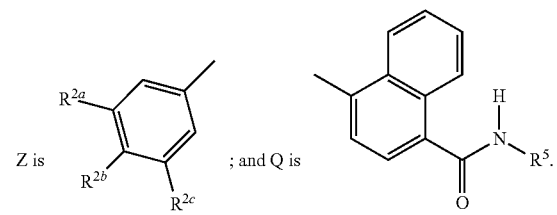

Z is ; and Q is

| $R^{2a}$ | $R^{2b}$ | $R^{2c}$ | $R^5$ |
|---|---|---|---|
| Cl | Cl | Cl | CH(Me)CH$_2$SMe |
| Cl | Cl | Cl | CH$_2$CH$_2$CH$_2$SMe |
| Cl | Cl | Cl | CH$_2$CH$_2$S(=O)Me |
| Cl | Cl | Cl | CH(Me)CH$_2$S(=O)Me |
| Cl | Cl | Cl | CH$_2$CH$_2$CH$_2$S(=O)Me |
| Cl | Cl | Cl | CH$_2$CH$_2$S(O)$_2$Me |
| Cl | Cl | Cl | CH(Me)CH$_2$S(O)$_2$Me |
| Cl | Cl | Cl | CH$_2$CH$_2$CH$_2$S(O)$_2$Me |
| Cl | Cl | Cl | CH$_2$C(=O)N(H)CH$_2$CF$_3$ |
| Cl | Cl | Cl | CH(Me)C(=O)N(H)CH$_2$CF$_3$ |
| Cl | Cl | Cl | CH$_2$C(=O)N(H)CH$_2$CH$_2$SMe |
| Cl | Cl | Cl | CH$_2$C(=O)N(H)CH$_2$CH$_2$S(O)$_2$Me |
| Cl | F | Cl | CH$_2$CH$_3$ |
| Cl | F | Cl | CH$_2$-i-Pr |
| Cl | F | Cl | CH$_2$CH$_2$Cl |
| Cl | F | Cl | CH$_2$CH$_2$OH |
| Cl | F | Cl | CH(Me)CH$_2$OH |
| Cl | F | Cl | CH$_2$CH(Me)OH |
| Cl | F | Cl | CH$_2$C(Me)$_2$OH |
| Cl | F | Cl | CH$_2$CH$_2$CH$_2$OH |
| Cl | F | Cl | CH$_2$C(Me)$_2$CH$_2$OH |
| Cl | F | Cl | CH$_2$CH$_2$CH(Me)OH |
| Cl | F | Cl | CH$_2$C(=O)N(H)Et |
| Cl | F | Cl | CH$_2$C(=O)N(H)-i-Pr |
| Cl | F | Cl | CH$_2$C(=O)N(H)CH$_2$-i-Pr |
| Cl | F | Cl | CH(Me)C(=O)N(H)CH$_2$-i-Pr |
| Cl | F | Cl | CH$_2$C(=O)N(H)CH$_2$CH$_2$Cl |
| Cl | F | Cl | CH(Me)C(=O)N(H)CH$_2$CH$_2$Cl |
| Cl | F | Cl | CH$_2$C(=O)N(H)CH$_2$CH$_2$F |
| Cl | F | Cl | CH(Me)C(=O)N(H)CH$_2$CH$_2$F |
| Cl | F | Cl | CH$_2$CF$_3$ |
| Cl | F | Cl | CH$_2$-(2-Py) |
| Cl | F | Cl | CH$_2$-(4-THz) |
| Cl | F | Cl | CH$_2$-c-Pr |
| Cl | F | Cl | CH$_2$CH$_2$SMe |
| Cl | F | Cl | CH(Me)CH$_2$SMe |
| Cl | F | Cl | CH$_2$CH$_2$CH$_2$SMe |
| Cl | F | Cl | CH$_2$CH$_2$S(=O)Me |
| Cl | F | Cl | CH(Me)CH$_2$S(=O)Me |
| Cl | F | Cl | CH$_2$CH$_2$CH$_2$S(=O)Me |
| Cl | F | Cl | CH$_2$CH$_2$S(O)$_2$Me |
| Cl | F | Cl | CH(Me)CH$_2$S(O)$_2$Me |
| Cl | F | Cl | CH$_2$CH$_2$CH$_2$S(O)$_2$Me |
| Cl | F | Cl | CH$_2$C(=O)N(H)CH$_2$CF$_3$ |
| Cl | F | Cl | CH(Me)C(=O)N(H)CH$_2$CF$_3$ |
| Cl | F | Cl | CH$_2$C(=O)N(H)CH$_2$CH$_2$SMe |
| Cl | F | Cl | CH$_2$C(=O)N(H)CH$_2$CH$_2$S(O)$_2$Me |
| OCF$_3$ | H | Cl | CH$_2$CH$_3$ |
| OCF$_3$ | H | Cl | CH$_2$-i-Pr |
| OCF$_3$ | H | Cl | CH$_2$CH$_2$Cl |
| OCF$_3$ | H | Cl | CH$_2$CH$_2$OH |
| OCF$_3$ | H | Cl | CH(Me)CH$_2$OH |
| OCF$_3$ | H | Cl | CH$_2$CH(Me)OH |
| OCF$_3$ | H | Cl | CH$_2$C(Me)$_2$OH |
| OCF$_3$ | H | Cl | CH$_2$CH$_2$CH$_2$OH |
| OCF$_3$ | H | Cl | CH$_2$C(Me)$_2$CH$_2$OH |
| OCF$_3$ | H | Cl | CH$_2$CH$_2$CH(Me)OH |
| OCF$_3$ | H | Cl | CH$_2$C(=O)N(H)Et |
| OCF$_3$ | H | Cl | CH$_2$C(=O)N(H)-i-Pr |
| OCF$_3$ | H | Cl | CH$_2$C(=O)N(H)CH$_2$-i-Pr |
| OCF$_3$ | H | Cl | CH(Me)C(=O)N(H)CH$_2$-i-Pr |
| OCF$_3$ | H | Cl | CH$_2$C(=O)N(H)CH$_2$CH$_2$Cl |
| OCF$_3$ | H | Cl | CH(Me)C(=O)N(H)CH$_2$CH$_2$Cl |
| OCF$_3$ | H | Cl | CH$_2$C(=O)N(H)CH$_2$CH$_2$F |
| OCF$_3$ | H | Cl | CH(Me)C(=O)N(H)CH$_2$CH$_2$F |
| OCF$_3$ | H | Cl | CH$_2$CF$_3$ |
| OCF$_3$ | H | Cl | CH$_2$-(2-Py) |

TABLE 7-continued

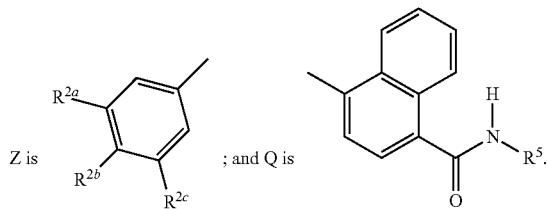
Z is ; and Q is

| R²ᵃ | R²ᵇ | R²ᶜ | R⁵ |
|---|---|---|---|
| OCF₃ | H | Cl | CH₂-(4-THz) |
| OCF₃ | H | Cl | CH₂-c-Pr |
| OCF₃ | H | Cl | CH₂CH₂SMe |
| OCF₃ | H | Cl | CH(Me)CH₂SMe |
| OCF₃ | H | Cl | CH₂CH₂CH₂SMe |
| OCF₃ | H | Cl | CH₂CH₂S(=O)Me |
| OCF₃ | H | Cl | CH(Me)CH₂S(=O)Me |
| OCF₃ | H | Cl | CH₂CH₂CH₂S(=O)Me |
| OCF₃ | H | Cl | CH₂CH₂S(O)₂Me |
| OCF₃ | H | Cl | CH(Me)CH₂S(O)₂Me |
| OCF₃ | H | Cl | CH₂CH₂CH₂S(O)₂Me |
| OCF₃ | H | Cl | CH₂C(=O)N(H)CH₂CF₃ |
| OCF₃ | H | Cl | CH(Me)C(=O)N(H)CH₂CF₃ |
| OCF₃ | H | Cl | CH₂C(=O)N(H)CH₂CH₂SMe |
| OCF₃ | H | Cl | CH₂C(=O)N(H)CH₂CH₂S(O)₂Me |

TABLE 8

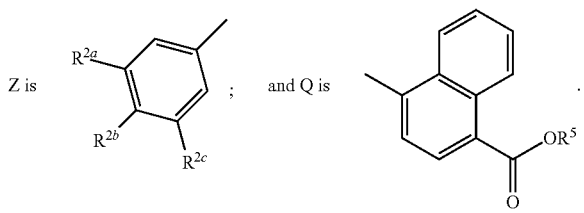
Z is ; and Q is

| R²ᵃ | R²ᵇ | R²ᶜ | R⁵ |
|---|---|---|---|
| Cl | H | Cl | CH₃ |
| Cl | H | Cl | CH₂CH₃ |
| Cl | H | Cl | CH₂-i-Pr |
| Cl | H | Cl | n-Pr |
| Cl | H | Cl | i-Pr |
| Cl | H | Cl | s-Bu |
| Cl | H | Cl | t-Bu |
| Cl | H | Cl | (CH₂)₅CH₃ |
| Cl | H | Cl | CH₂Ph |
| Br | H | Br | CH₃ |
| Br | H | Br | CH₂CH₃ |
| Br | H | Br | CH₂-i-Pr |
| Br | H | Br | n-Pr |
| Br | H | Br | i-Pr |
| Br | H | Br | s-Bu |
| Br | H | Br | t-Bu |
| Br | H | Br | (CH₂)₅CH₃ |
| Br | H | Br | CH₂Ph |
| CF₃ | H | H | CH₃ |
| CF₃ | H | H | CH₂CH₃ |
| CF₃ | H | H | CH₂-i-Pr |
| CF₃ | H | H | n-Pr |
| CF₃ | H | H | i-Pr |
| CF₃ | H | H | s-Bu |
| CF₃ | H | H | t-Bu |
| CF₃ | H | H | (CH₂)₅CH₃ |
| CF₃ | H | H | CH₂Ph |
| CF₃ | H | F | CH₃ |
| CF₃ | H | F | CH₂CH₃ |
| CF₃ | H | F | CH₂-i-Pr |
| CF₃ | H | F | n-Pr |
| CF₃ | H | F | i-Pr |
| CF₃ | H | F | s-Bu |
| CF₃ | H | F | t-Bu |

TABLE 8-continued

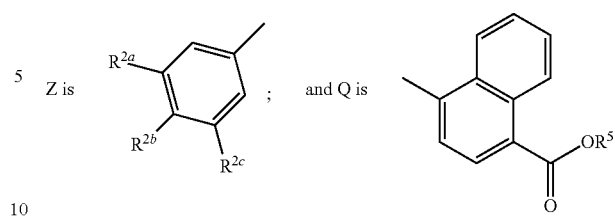
Z is ; and Q is

| R²ᵃ | R²ᵇ | R²ᶜ | R⁵ |
|---|---|---|---|
| CF₃ | H | F | (CH₂)₅CH₃ |
| CF₃ | H | F | CH₂Ph |
| CF₃ | H | Br | CH₃ |
| CF₃ | H | Br | CH₂CH₃ |
| CF₃ | H | Br | CH₂-i-Pr |
| CF₃ | H | Br | n-Pr |
| CF₃ | H | Br | i-Pr |
| CF₃ | H | Br | s-Bu |
| CF₃ | H | Br | t-Bu |
| CF₃ | H | Br | (CH₂)₅CH₃ |
| CF₃ | H | Br | CH₂Ph |
| CF₃ | H | Cl | CH₃ |
| CF₃ | H | Cl | CH₂CH₃ |
| CF₃ | H | Cl | CH₂-i-Pr |
| CF₃ | H | Cl | n-Pr |
| CF₃ | H | Cl | i-Pr |
| CF₃ | H | Cl | s-Bu |
| CF₃ | H | Cl | t-Bu |
| CF₃ | H | Cl | (CH₂)₅CH₃ |
| CF₃ | H | Cl | CH₂Ph |
| CF₃ | H | CF₃ | CH₃ |
| CF₃ | H | CF₃ | CH₂CH₃ |
| CF₃ | H | CF₃ | CH₂-i-Pr |
| CF₃ | H | CF₃ | n-Pr |
| CF₃ | H | CF₃ | i-Pr |
| CF₃ | H | CF₃ | s-Bu |
| CF₃ | H | CF₃ | t-Bu |
| CF₃ | H | CF₃ | (CH₂)₅CH₃ |
| CF₃ | H | CF₃ | CH₂Ph |
| Cl | Cl | Cl | CH₃ |
| Cl | Cl | Cl | CH₂CH₃ |
| Cl | Cl | Cl | CH₂-i-Pr |
| Cl | Cl | Cl | n-Pr |
| Cl | Cl | Cl | i-Pr |
| Cl | Cl | Cl | s-Bu |
| Cl | Cl | Cl | t-Bu |
| Cl | Cl | Cl | (CH₂)₅CH₃ |
| Cl | Cl | Cl | CH₂Ph |
| Cl | F | Cl | CH₃ |
| Cl | F | Cl | CH₂CH₃ |
| Cl | F | Cl | CH₂-i-Pr |
| Cl | F | Cl | n-Pr |
| Cl | F | Cl | i-Pr |
| Cl | F | Cl | s-Bu |
| Cl | F | Cl | n-Bu |
| Cl | F | Cl | t-Bu |
| Cl | F | Cl | (CH₂)₅CH₃ |
| Cl | F | Cl | CH₂Ph |
| OCF₃ | H | Cl | CH₃ |
| OCF₃ | H | Cl | CH₂CH₃ |
| OCF₃ | H | Cl | CH₂-i-Pr |
| OCF₃ | H | Cl | n-Pr |
| OCF₃ | H | Cl | i-Pr |
| OCF₃ | H | Cl | s-Bu |
| OCF₃ | H | Cl | t-Bu |
| OCF₃ | H | Cl | (CH₂)₅CH₃ |
| OCF₃ | H | Cl | CH₂Ph |

TABLE 9

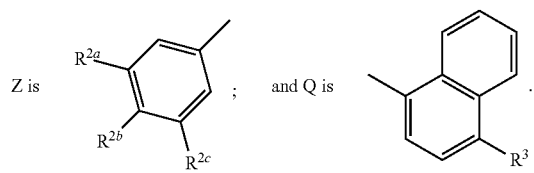

Z is [structure]; and Q is [structure].

| $R^{2a}$ | $R^{2b}$ | $R^{2c}$ | $R^3$ |
|---|---|---|---|
| Cl | H | Cl | Cl |
| Cl | H | Cl | Br |
| Cl | H | Cl | I |
| Cl | H | Cl | OH |
| Cl | H | Cl | OMe |
| Cl | H | Cl | OS(O)$_2$CF$_3$ |
| Cl | H | Cl | nitro |
| Cl | H | Cl | NH$_2$ |
| Cl | H | Cl | cyano |
| Cl | H | Cl | Me |
| Cl | H | Cl | CH$_2$Cl |
| Cl | H | Cl | CH$_2$Br |
| Cl | H | Cl | CH$_2$OH |
| Cl | H | Cl | CH$_2$OC(O)Me |
| Cl | H | Cl | CO$_2$H |
| Cl | H | Cl | n-Pr |
| Br | H | Br | Cl |
| Br | H | Br | Br |
| Br | H | Br | I |
| Br | H | Br | OH |
| Br | H | Br | OMe |
| Br | H | Br | OS(O)$_2$CF$_3$ |
| Br | H | Br | nitro |
| Br | H | Br | NH$_2$ |
| Br | H | Br | cyano |
| Br | H | Br | Me |
| Br | H | Br | CH$_2$Cl |
| Br | H | Br | CH$_2$Br |
| Br | H | Br | CH$_2$OH |
| Br | H | Br | CH$_2$OC(O)Me |
| Br | H | Br | CO$_2$H |
| Br | H | Br | n-Pr |
| CF$_3$ | H | H | Cl |
| CF$_3$ | H | H | Br |
| CF$_3$ | H | H | I |
| CF$_3$ | H | H | OH |
| CF$_3$ | H | H | OMe |
| CF$_3$ | H | H | OS(O)$_2$CF$_3$ |
| CF$_3$ | H | H | nitro |
| CF$_3$ | H | H | NH$_2$ |
| CF$_3$ | H | H | cyano |
| CF$_3$ | H | H | Me |
| CF$_3$ | H | H | CH$_2$Cl |
| CF$_3$ | H | H | CH$_2$Br |
| CF$_3$ | H | H | CH$_2$OH |
| CF$_3$ | H | H | CH$_2$OC(O)Me |
| CF$_3$ | H | H | CO$_2$H |
| CF$_3$ | H | H | n-Pr |
| CF$_3$ | H | F | Cl |
| CF$_3$ | H | F | Br |
| CF$_3$ | H | F | I |
| CF$_3$ | H | F | OH |
| CF$_3$ | H | F | OMe |
| CF$_3$ | H | F | OS(O)$_2$CF$_3$ |
| CF$_3$ | H | F | nitro |
| CF$_3$ | H | F | NH$_2$ |
| CF$_3$ | H | F | cyano |
| CF$_3$ | H | F | Me |
| CF$_3$ | H | F | CH$_2$Cl |
| CF$_3$ | H | F | CH$_2$Br |
| CF$_3$ | H | F | CH$_2$OH |
| CF$_3$ | H | F | CH$_2$OC(O)Me |
| CF$_3$ | H | F | CO$_2$H |
| CF$_3$ | H | F | n-Pr |
| CF$_3$ | H | Br | Cl |
| CF$_3$ | H | Br | Br |
| CF$_3$ | H | Br | I |
| CF$_3$ | H | Br | OH |
| CF$_3$ | H | Br | OMe |
| CF$_3$ | H | Br | OS(O)$_2$CF$_3$ |
| CF$_3$ | H | Br | nitro |
| CF$_3$ | H | Br | NH$_2$ |
| CF$_3$ | H | Br | cyano |
| CF$_3$ | H | Br | Me |
| CF$_3$ | H | Br | CH$_2$Cl |
| CF$_3$ | H | Br | CH$_2$Br |
| CF$_3$ | H | Br | CH$_2$OH |
| CF$_3$ | H | Br | CH$_2$OC(O)Me |
| CF$_3$ | H | Br | CO$_2$H |
| CF$_3$ | H | Br | n-Pr |
| CF$_3$ | H | Cl | Cl |
| CF$_3$ | H | Cl | Br |
| CF$_3$ | H | Cl | I |
| CF$_3$ | H | Cl | OH |
| CF$_3$ | H | Cl | OMe |
| CF$_3$ | H | Cl | OS(O)$_2$CF$_3$ |
| CF$_3$ | H | Cl | nitro |
| CF$_3$ | H | Cl | NH$_2$ |
| CF$_3$ | H | Cl | cyano |
| CF$_3$ | H | Cl | Me |
| CF$_3$ | H | Cl | CH$_2$Cl |
| CF$_3$ | H | Cl | CH$_2$Br |
| CF$_3$ | H | Cl | CH$_2$OH |
| CF$_3$ | H | Cl | CH$_2$OC(O)Me |
| CF$_3$ | H | Cl | CO$_2$H |
| CF$_3$ | H | Cl | n-Pr |
| CF$_3$ | H | CF$_3$ | Cl |
| CF$_3$ | H | CF$_3$ | Br |
| CF$_3$ | H | CF$_3$ | I |
| CF$_3$ | H | CF$_3$ | OH |
| CF$_3$ | H | CF$_3$ | OMe |
| CF$_3$ | H | CF$_3$ | OS(O)$_2$CF$_3$ |
| CF$_3$ | H | CF$_3$ | nitro |
| CF$_3$ | H | CF$_3$ | NH$_2$ |
| CF$_3$ | H | CF$_3$ | cyano |
| CF$_3$ | H | CF$_3$ | Me |
| CF$_3$ | H | CF$_3$ | CH$_2$Cl |
| CF$_3$ | H | CF$_3$ | CH$_2$Br |
| CF$_3$ | H | CF$_3$ | CH$_2$OH |
| CF$_3$ | H | CF$_3$ | CH$_2$OC(O)Me |
| CF$_3$ | H | CF$_3$ | CO$_2$H |
| CF$_3$ | H | CF$_3$ | n-Pr |
| Cl | Cl | Cl | Cl |
| Cl | Cl | Cl | Br |
| Cl | Cl | Cl | I |
| Cl | Cl | Cl | OH |
| Cl | Cl | Cl | OMe |
| Cl | Cl | Cl | OS(O)$_2$CF$_3$ |
| Cl | Cl | Cl | nitro |
| Cl | Cl | Cl | NH$_2$ |
| Cl | Cl | Cl | cyano |
| Cl | Cl | Cl | Me |
| Cl | Cl | Cl | CH$_2$Cl |
| Cl | Cl | Cl | CH$_2$Br |
| Cl | Cl | Cl | CH$_2$OH |
| Cl | Cl | Cl | CH$_2$OC(O)Me |
| Cl | Cl | Cl | CO$_2$H |
| Cl | Cl | Cl | n-Pr |
| Cl | F | Cl | Cl |
| Cl | F | Cl | Br |
| Cl | F | Cl | I |
| Cl | F | Cl | OH |
| Cl | F | Cl | OMe |
| Cl | F | Cl | OS(O)$_2$CF$_3$ |
| Cl | F | Cl | nitro |
| Cl | F | Cl | NH$_2$ |
| Cl | F | Cl | cyano |
| Cl | F | Cl | Me |

TABLE 9-continued

Z is ![structure with R2a, R2b, R2c] ; and Q is ![naphthyl with R3]

| $R^{2a}$ | $R^{2b}$ | $R^{2c}$ | $R^3$ |
|---|---|---|---|
| Cl | F | Cl | $CH_2Cl$ |
| CL | F | Cl | $CH_2Br$ |
| Cl | F | Cl | $CH_2OH$ |
| Cl | F | Cl | $CH_2OC(O)Me$ |
| Cl | F | Cl | $CO_2H$ |
| Cl | F | Cl | n-Pr |
| $OCF_3$ | H | Cl | Cl |
| $OCF_3$ | H | Cl | Br |
| $OCF_3$ | H | Cl | I |
| $OCF_3$ | H | Cl | OH |
| $OCF_3$ | H | Cl | OMe |
| $OCF_3$ | H | Cl | $OS(O)_2CF_3$ |
| $OCF_3$ | H | Cl | nitro |
| $OCF_3$ | H | Cl | $NH_2$ |
| $OCF_3$ | H | Cl | cyano |
| $OCF_3$ | H | Cl | Me |
| $OCF_3$ | H | Cl | $CH_2Cl$ |
| $OCF_3$ | H | Cl | $CH_2Br$ |
| $OCF_3$ | H | Cl | $CH_2OH$ |
| $OCF_3$ | H | Cl | $CH_2OC(O)Me$ |
| $OCF_3$ | H | Cl | $CO_2H$ |
| $OCF_3$ | H | Cl | n-Pr |

Tables 10-12 relate to the method of Scheme 1b converting compound of Formulae 2 and 3 to corresponding compounds of Formula 1. This transformation is believed to occur through the intermediacy of compounds of Formula 11.

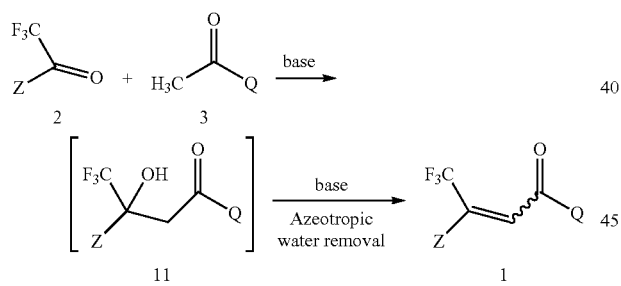

In the example transformations embodied in Tables 10-12, the base is 1,8-diazabicyclo[5.4.0]undec-7-ene, and water is distilled as an azeotrope from a reaction mixture comprising acetonitrile as the aprotic solvent capable of forming a low-boiling azeotrope with water.

TABLE 10

Z is ![structure with R2a, R2b, R2c] ; and Q is ![naphthyl-CH2-NH-R5]

| $R^{2a}$ | $R^{2b}$ | $R^{2c}$ | $R^5$ |
|---|---|---|---|
| Cl | H | Cl | $CH_2CH_3$ |
| Cl | H | Cl | $CH_2$-i-Pr |
| Cl | H | Cl | $CH_2CH_2Cl$ |
| Cl | H | Cl | $CH_2CH_2OH$ |
| Cl | H | Cl | $CH(Me)CH_2OH$ |
| Cl | H | Cl | $CH_2CH(Me)OH$ |
| Cl | H | Cl | $CH_2C(Me)_2OH$ |
| Cl | H | Cl | $CH_2CH_2CH_2OH$ |
| Cl | H | Cl | $CH_2C(Me)_2CH_2OH$ |
| Cl | H | Cl | $CH_2CH_2CH(Me)OH$ |
| Cl | H | Cl | $CH_2C(=O)N(H)Et$ |
| Cl | H | Cl | $CH_2C(=O)N(H)$-i-Pr |
| Cl | H | Cl | $CH_2C(=O)N(H)CH_2$-i-Pr |
| Cl | H | Cl | $CH(Me)C(=O)N(H)CH_2$-i-Pr |
| Cl | H | Cl | $CH_2C(=O)N(H)CH_2CH_2Cl$ |
| Cl | H | Cl | $CH(Me)C(=O)N(H)CH_2CH_2Cl$ |
| Cl | H | Cl | $CH_2C(=O)N(H)CH_2CH_2F$ |
| Cl | H | Cl | $CH(Me)C(=O)N(H)CH_2CH_2F$ |
| Cl | H | Cl | $CH_2CF_3$ |
| Cl | H | Cl | $CH_2$-(2-Py) |
| Cl | H | Cl | $CH_2$-(4-Thz) |
| Cl | H | Cl | $CH_2$-c-Pr |
| Cl | H | Cl | $CH_2CH_2SMe$ |
| Cl | H | Cl | $CH(Me)CH_2SMe$ |
| Cl | H | Cl | $CH_2CH_2CH_2SMe$ |
| Cl | H | Cl | $CH_2CH_2S(=O)Me$ |
| Cl | H | Cl | $CH(Me)CH_2S(=O)Me$ |
| Cl | H | Cl | $CH_2CH_2CH_2S(=O)Me$ |
| Cl | H | Cl | $CH_2CH_2S(O)_2Me$ |
| Cl | H | Cl | $CH(Me)CH_2S(O)_2Me$ |
| Cl | H | Cl | $CH_2CH_2CH_2S(O)_2Me$ |
| Cl | H | Cl | $CH_2C(=O)N(H)CH_2CF_3$ |
| Cl | H | Cl | $CH(Me)C(=O)N(H)CH_2CF_3$ |
| Cl | H | Cl | $CH_2C(=O)N(H)CH_2CH_2SMe$ |
| Cl | H | Cl | $CH_2C(=O)N(H)CH_2CH_2S(O)_2Me$ |
| Br | H | Br | $CH_2CH_3$ |
| Br | H | Br | $CH_2$-i-Pr |
| Br | H | Br | $CH_2CH_2Cl$ |
| Br | H | Br | $CH_2CH_2OH$ |
| Br | H | Br | $CH(Me)C_2OH$ |
| Br | H | Br | $CH_2CH(Me)OH$ |
| Br | H | Br | $CH_2C(Me)_2OH$ |
| Br | H | Br | $CH_2CH_2CH_2OH$ |
| Br | H | Br | $CH_2C(Me)_2CH_2OH$ |
| Br | H | Br | $CH_2CH_2CH(Me)OH$ |
| Br | H | Br | $CH_2C(=O)N(H)Et$ |
| Br | H | Br | $CH_2C(=O)N(H)$-i-Pr |
| Br | H | Br | $CH_2C(=O)N(H)CH_2$-i-Pr |
| Br | H | Br | $CH(Me)C(=O)N(H)CH_2$-i-Pr |
| Br | H | Br | $CH_2C(=O)N(H)CH_2CH_2Cl$ |
| Br | H | Br | $CH(Me)C(=O)N(H)CH_2CH_2Cl$ |
| Br | H | Br | $CH_2C(=O)N(H)CH_2CH_2F$ |
| Br | H | Br | $CH(Me)C(=O)N(H)CH_2CH_2F$ |
| Br | H | Br | $CH_2CF_3$ |
| Br | H | Br | $CH_2$-(2-Py) |
| Br | H | Br | $CH_2$-(4-Thz) |
| Br | H | Br | $CH_2$-c-Pr |
| Br | H | Br | $CH_2CH_2SMe$ |
| Br | H | Br | $CH_2CH_2CH_2SMe$ |
| Br | H | Br | $CH_2CH_2S(=O)Me$ |
| Br | H | Br | $CH(Me)CH_2S(=O)Me$ |
| Br | H | Br | $CH(Me)CH_2S(=O)Me$ |
| Br | H | Br | $CH_2CH_2CH_2S(=O)Me$ |
| Br | H | Br | $CH_2CH_2S(O)_2Me$ |
| Br | H | Br | $CH(Me)CH_2S(O)_2Me$ |
| Br | H | Br | $CH_2CH_2CH_2S(O)_2Me$ |
| Br | H | Br | $CH_2C(=O)N(H)CH_2CF_3$ |
| Br | H | Br | $CH(Me)C(=O)N(H)CH_2CF_3$ |
| Br | H | Br | $CH_2C(=O)N(H)CH_2CH_2SMe$ |
| Br | H | Br | $CH_2C(=O)N(H)CH_2CH_2S(O)_2Me$ |
| $CF_3$ | H | H | $CH_2CH_3$ |
| $CF_3$ | H | H | $CH_2$-i-Pr |

TABLE 10-continued

Z is

![structure with R2a, R2b, R2c on phenyl]

; and Q is

![naphthyl-CH2-N(H)-R5]

| $R^{2a}$ | $R^{2b}$ | $R^{2c}$ | $R^5$ |
|---|---|---|---|
| CF$_3$ | H | H | CH$_2$CH$_2$Cl |
| CF$_3$ | H | H | CH$_2$CH$_2$OH |
| CF$_3$ | H | H | CH(Me)CH$_2$OH |
| CF$_3$ | H | H | CH$_2$CH(Me)OH |
| CF$_3$ | H | H | CH$_2$C(Me)$_2$OH |
| CF$_3$ | H | H | CH$_2$CH$_2$CH$_2$OH |
| CF | H | H | CH$_2$C(Me)$_2$CH$_2$OH |
| CF$_3$ | H | H | CH$_2$CH$_2$CH(Me)OH |
| CF$_3$ | H | H | CH$_2$C(=O)N(H)Et |
| CF$_3$ | H | H | CH$_2$C(=O)N(H)-i-Pr |
| CF$_3$ | H | H | CH$_2$C(=O)N(H)CH$_2$-i-Pr |
| CF$_3$ | H | H | CH(Me)C(=O)N(H)CH$_2$-i-Pr |
| CF$_3$ | H | H | CH$_2$C(=O)N(H)CH$_2$CH$_2$Cl |
| CF$_3$ | H | H | CH$_2$C(=O)N(H)CH$_2$CH$_2$F |
| CF$_3$ | H | H | CH(Me)C(=O)N(H)CH$_2$CH$_2$F |
| CF$_3$ | H | H | CH$_2$CF$_3$ |
| CF$_3$ | H | H | CH$_2$-(2-Py) |
| CF$_3$ | H | H | CH$_2$-(4-Thz) |
| CF$_3$ | H | H | CH$_2$-c-Pr |
| CF$_3$ | H | H | CH$_2$CH$_2$SMe |
| CF$_3$ | H | H | CH(Me)CH$_2$SMe |
| CF$_3$ | H | H | CH$_2$CH$_2$CH$_2$SMe |
| CF$_3$ | H | H | CH$_2$CH$_2$S(=O)Me |
| CF$_3$ | H | H | CH(Me)CH$_2$S(=O)Me |
| CF$_3$ | H | H | CH$_2$CH$_2$CH$_2$S(=O)Me |
| CF | H | H | CH$_2$CH$_2$S(O)$_2$Me |
| CF$_3$ | H | H | CH(Me)CH$_2$S(O)$_2$Me |
| CF$_3$ | H | H | CH$_2$CH$_2$CH$_2$S(O)$_2$Me |
| CF$_3$ | H | H | CH$_2$C(=O)N(H)CH$_2$CF$_3$ |
| CF$_3$ | H | H | CH(Me)C(=O)N(H)CH$_2$CF$_3$ |
| CF$_3$ | H | H | CH$_2$C(=O)N(H)CH$_2$CH$_2$SMe |
| CF$_3$ | H | H | CH$_2$C(=O)N(H)CH$_2$CH$_2$S(O)$_2$Me |
| CF$_3$ | H | F | CH$_2$CH$_3$ |
| CF$_3$ | H | F | CH$_2$-i-Pr |
| CF$_3$ | H | F | CH$_2$CH$_2$Cl |
| CF$_3$ | H | F | CH$_2$CH$_2$OH |
| CF$_3$ | H | F | CH(Me)CH$_2$OH |
| CF$_3$ | H | F | CH$_2$CH(Me)OH |
| CF$_3$ | H | F | CH$_2$C(Me)$_2$OH |
| CF$_3$ | H | F | CH$_2$CH$_2$CH$_2$OH |
| CF$_3$ | H | F | CH$_2$C(Me)$_2$CH$_2$OH |
| CF$_3$ | H | F | CH$_2$CH$_2$CH(Me)OH |
| CF$_3$ | H | F | CH$_2$C(=O)N(H)Et |
| CF$_3$ | H | F | CH$_2$C(=O)N(H)-i-Pr |
| CF$_3$ | H | F | CH$_2$C(=O)N(H)CH$_2$-i-Pr |
| CF$_3$ | H | F | CH(Me)C(=O)N(H)CH$_2$-i-Pr |
| CF$_3$ | H | F | CH$_2$C(=O)N(H)CH$_2$CH$_2$Cl |
| CF$_3$ | H | F | CH(Me)C(=O)N(H)CH$_2$CH$_2$Cl |
| CF$_3$ | H | F | CH$_2$C(=O)N(H)CH$_2$CH$_2$F |
| CF$_3$ | H | F | CH$_2$CF$_3$ |
| CF$_3$ | H | F | CH$_2$-(2-Py) |
| CF$_3$ | H | F | CH$_2$-(4-Thz) |
| CF$_3$ | H | F | CH$_2$-c-Pr |
| CF$_3$ | H | F | CH$_2$CH$_2$SMe |
| CF$_3$ | H | F | CH(Me)CH$_2$SMe |
| CF$_3$ | H | F | CH$_2$CH$_2$CH$_2$SMe |
| CF$_3$ | H | F | CH$_2$CH$_2$S(=O)Me |
| CF$_3$ | H | F | CH(Me)CH$_2$S(=O)Me |
| CF$_3$ | H | F | CH$_2$CH$_2$CH$_2$S(=O)Me |
| CF$_3$ | H | F | CH$_2$CH$_2$S(O)$_2$Me |
| CF$_3$ | H | F | CH(Me)CH$_2$S(O)$_2$Me |
| CF$_3$ | H | F | CH$_2$CH$_2$CH$_2$S(O)$_2$Me |
| CF$_3$ | H | F | CH$_2$C(=O)N(H)CH$_2$CF$_3$ |
| CF$_3$ | H | F | CH(Me)C(=O)N(H)CH$_2$CF$_3$ |
| CF$_3$ | H | F | CH$_2$C(=O)N(H)CH$_2$CH$_2$SMe |
| CF$_3$ | H | F | CH$_2$C(=O)N(H)CH$_2$CH$_2$S(O)$_2$Me |
| CF$_3$ | H | Br | CH$_2$CH$_3$ |
| CF$_3$ | H | Br | CH$_2$-i-Pr |
| CF$_3$ | H | Br | CH$_2$CH$_2$Cl |
| CF$_3$ | H | Br | CH$_2$CH$_2$OH |
| CF$_3$ | H | Br | CH(Me)CH$_2$OH |
| CF$_3$ | H | Br | CH$_2$CH(Me)OH |
| CF$_3$ | H | Br | CH$_2$C(Me)$_2$OH |
| CF$_3$ | H | Br | CH$_2$CH$_2$CH$_2$OH |
| CF$_3$ | H | Br | CH$_2$C(Me)$_2$CH$_2$OH |
| CF$_3$ | H | Br | CH$_2$CH$_2$CH(Me)OH |
| CF$_3$ | H | Br | CH$_2$C(=O)N(H)Et |
| CF$_3$ | H | Br | CH$_2$C(=O)N(H)-i-Pr |
| CF$_3$ | H | Br | CH$_2$C(=O)N(H)CH$_2$-i-Pr |
| CF$_3$ | H | Br | CH(Me)C(=O)N(H)CH$_2$-i-Pr |
| CF$_3$ | H | Br | CH$_2$C(=O)N(H)CH$_2$CH$_2$Cl |
| CF$_3$ | H | Br | CH(Me)C(=O)N(H)CH$_2$CH$_2$Cl |
| CF$_3$ | H | Br | CH$_2$C(=O)N(H)CH$_2$CH$_2$F |
| CF$_3$ | H | Br | CH(Me)C(=O)N(H)CH$_2$CH$_2$F |
| CF$_3$ | H | Br | CH$_2$CF$_3$ |
| CF$_3$ | H | Br | CH$_2$-(2-Py) |
| CF$_3$ | H | Br | CH$_2$-(4-Thz) |
| CF$_3$ | H | Br | CH$_2$-c-Pr |
| CF$_3$ | H | Br | CH$_2$CH$_2$SMe |
| CF$_3$ | H | Br | CH(Me)CH$_2$SMe |
| CF$_3$ | H | Br | CH$_2$CH$_2$CH$_2$SMe |
| CF$_3$ | H | Br | CH$_2$CH$_2$S(=O)Me |
| CF$_3$ | H | Br | CH(Me)CH$_2$S(=O)Me |
| CF$_3$ | H | Br | CH$_2$CH$_2$CH$_2$S(=O)Me |
| CF$_3$ | H | Br | CH$_2$CH$_2$S(O)$_2$Me |
| CF$_3$ | H | Br | CH(Me)CH$_2$S(O)$_2$Me |
| CF$_3$ | H | Br | CH$_2$CH$_2$CH$_2$S(O)$_2$Me |
| CF$_3$ | H | Br | CH$_2$C(=O)N(H)CH$_2$CF$_3$ |
| CF$_3$ | H | Br | CH(Me)C(=O)N(H)CH$_2$CF$_3$ |
| CF$_3$ | H | Br | CH$_2$C(=O)N(H)CH$_2$CH$_2$SMe |
| CF$_3$ | H | Br | CH$_2$C(=O)N(H)CH$_2$CH$_2$S(O)$_2$Me |
| CF$_3$ | H | Cl | CH$_2$CH$_3$ |
| CF$_3$ | H | Cl | CH$_2$-i-Pr |
| CF$_3$ | H | Cl | CH$_2$CH$_2$Cl |
| CF$_3$ | H | Cl | CH$_2$CH$_2$OH |
| CF$_3$ | H | Cl | CH(Me)CH$_2$OH |
| CF$_3$ | H | Cl | CH$_2$CH(Me)OH |
| CF$_3$ | H | Cl | CH$_2$C(Me)$_2$OH |
| CF$_3$ | H | Cl | CH$_2$CH$_2$CH$_2$OH |
| CF$_3$ | H | Cl | CH$_2$C(Me)$_2$CH$_2$OH |
| CF$_3$ | H | Cl | CH$_2$CH$_2$CH(Me)OH |
| CF$_3$ | H | Cl | CH$_2$C(=O)N(H)Et |
| CF$_3$ | H | Cl | CH$_2$C(=O)N(H)-i-Pr |
| CF$_3$ | H | Cl | CH$_2$C(=O)N(H)CH$_2$-i-Pr |
| CF$_3$ | H | Cl | CH(Me)C(=O)N(H)CH$_2$-i-Pr |
| CF$_3$ | H | Cl | CH$_2$C(=O)N(H)CH$_2$CH$_2$Cl |
| CF$_3$ | H | Cl | CH(Me)C(=O)N(H)CH$_2$CH$_2$Cl |
| CF$_3$ | H | Cl | CH$_2$C(=O)N(H)CH$_2$CH$_2$F |
| CF$_3$ | H | Cl | CH(Me)C(=O)N(H)CH$_2$CH$_2$F |
| CF$_3$ | H | Cl | CH$_2$CF$_3$ |
| CF$_3$ | H | Cl | CH$_2$-(2-Py) |
| CF$_3$ | H | Cl | CH$_2$-(4-Thz) |
| CF$_3$ | H | Cl | CH$_2$-c-Pr |
| CF$_3$ | H | Cl | CH$_2$CH$_2$SMe |
| CF$_3$ | H | Cl | CH(Me)CH$_2$SMe |
| CF$_3$ | H | Cl | CH$_2$CH$_2$CH$_2$SMe |
| CF$_3$ | H | Cl | CH$_2$CH$_2$S(=O)Me |
| CF$_3$ | H | Cl | CH(Me)CH$_2$S(=O)Me |
| CF$_3$ | H | Cl | CH$_2$CH$_2$CH$_2$S(=O)Me |
| CF$_3$ | H | Cl | CH$_2$CH$_2$S(O)$_2$Me |
| CF$_3$ | H | Cl | CH(Me)CH$_2$S(O)$_2$Me |
| CF$_3$ | H | Cl | CH$_2$CH$_2$CH$_2$S(O)$_2$Me |
| CF$_3$ | H | Cl | CH$_2$C(=O)N(H)CH$_2$CF$_3$ |
| CF$_3$ | H | Cl | CH(Me)C(=O)N(H)CH$_2$CF$_3$ |
| CF$_3$ | H | Cl | CH$_2$C(=O)N(H)CH$_2$CH$_2$SMe |
| CF$_3$ | H | Cl | CH$_2$C(=O)N(H)CH$_2$CH$_2$S(O)$_2$Me |
| CF$_3$ | H | CF$_3$ | CH$_2$CH$_3$ |
| CF$_3$ | H | CF$_3$ | CH$_2$-i-Pr |
| CF$_3$ | H | CF$_3$ | CH$_2$CH$_2$Cl |
| CF$_3$ | H | CF$_3$ | CH$_2$CH$_2$OH |

TABLE 10-continued

Z is 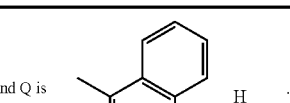 ; and Q is 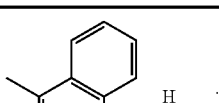.

| R2a | R2b | R2c | R5 |
|---|---|---|---|
| CF3 | H | CF3 | CH(Me)CH2OH |
| CF3 | H | CF3 | CH2CH(Me)OH |
| CF3 | H | CF3 | CH2C(Me)2OH |
| CF3 | H | CF3 | CH2CH2CH2OH |
| CF3 | H | CF3 | CH2C(Me)2CH2OH |
| CF3 | H | CF3 | CH2CH2CH(Me)OH |
| CF3 | H | CF3 | CH2C(=O)N(H)Et |
| CF3 | H | CF3 | CH2C(=O)N(H)-i-Pr |
| CF3 | H | CF3 | CH2C(=O)N(H)CH2-i-Pr |
| CF3 | H | CF3 | CH(Me)C(=O)N(H)CH2-i-Pr |
| CF3 | H | CF3 | CH2C(=O)N(H)CH2CH2Cl |
| CF3 | H | CF3 | CH(Me)C(=O)N(H)CH2CH2Cl |
| CF3 | H | CF3 | CH2C(=O)N(H)CH2CH2F |
| CF3 | H | CF3 | CH(Me)C(=O)N(H)CH2CH2F |
| CF3 | H | CF3 | CH2CF3 |
| CF3 | H | CF3 | CH2-(2-Py) |
| CF3 | H | CF3 | CH2-(4-Thz) |
| CF3 | H | CF3 | CH2-c-Pr |
| CF3 | H | CF3 | CH2CH2SMe |
| CF3 | H | CF3 | CH(Me)CH2SMe |
| CF3 | H | CF3 | CH2CH2CH2SMe |
| CF3 | H | CF3 | CH2CH2S(=O)Me |
| CF3 | H | CF3 | CH(Me)CH2S(=O)Me |
| CF3 | H | CF3 | CH2CH2CH2S(=O)Me |
| CF3 | H | CF3 | CH2CH2S(O)2Me |
| CF3 | H | CF3 | CH(Me)CH2S(O)2Me |
| CF3 | H | CF3 | CH2CH2CH2S(O)2Me |
| CF3 | H | CF3 | CH2C(=O)N(H)CH2CF3 |
| CF3 | H | CF3 | CH(Me)C(=O)N(H)CH2CF3 |
| CF3 | H | CF3 | CH2C(=O)N(H)CH2CH2SMe |
| CF3 | H | CF3 | CH2C(=O)N(H)CH2CH2S(O)2Me |
| Cl | Cl | Cl | CH2CH3 |
| Cl | Cl | Cl | CH2-i-Pr |
| Cl | Cl | Cl | CH2CH2Cl |
| Cl | Cl | Cl | CH2CH2OH |
| Cl | Cl | Cl | CH(Me)CH2OH |
| Cl | Cl | Cl | CH2CH(Me)OH |
| Cl | Cl | Cl | CH2C(Me)2OH |
| Cl | Cl | Cl | CH2CH2CH2OH |
| Cl | Cl | Cl | CH2C(Me)2CH2OH |
| Cl | Cl | Cl | CH2CH2CH(Me)OH |
| Cl | Cl | Cl | CH2C(=O)N(H)Et |
| Cl | Cl | Cl | CH2C(=O)N(H)-i-Pr |
| Cl | Cl | Cl | CH2C(=O)N(H)CH2-i-Pr |
| Cl | Cl | Cl | CH(Me)C(=O)N(H)CH2-i-Pr |
| Cl | Cl | Cl | CH2C(=O)N(H)CH2CH2Cl |
| Cl | Cl | Cl | CH(Me)C(=O)N(H)CH2CH2Cl |
| Cl | Cl | Cl | CH2C(=O)N(H)CH2CH2F |
| Cl | Cl | Cl | CH(Me)C(=O)N(H)CH2CH2F |
| Cl | Cl | Cl | CH2CF3 |
| Cl | Cl | Cl | CH2-(2-Py) |
| Cl | Cl | Cl | CH2-(4-Thz) |
| Cl | Cl | Cl | CH2-c-Pr |
| Cl | Cl | Cl | CH2CH2SMe |
| Cl | Cl | Cl | CH(Me)CH2SMe |
| Cl | Cl | Cl | CH2CH2CH2SMe |
| Cl | Cl | Cl | CH2CH2S(=O)Me |
| Cl | Cl | Cl | CH(Me)CH2S(=O)Me |
| Cl | Cl | Cl | CH2CH2CH2S(=O)Me |
| Cl | Cl | Cl | CH2CH2S(O)2Me |
| Cl | Cl | Cl | CH(Me)CH2S(O)2Me |
| Cl | Cl | Cl | CH2CH2CH2S(O)2Me |
| Cl | Cl | Cl | CH2C(=O)N(H)CH2CF3 |
| Cl | Cl | Cl | CH(Me)C(=O)N(H)CH2CF3 |
| Cl | Cl | Cl | CH2C(=O)N(H)CH2CH2SMe |
| Cl | Cl | Cl | CH2C(=O)N(H)CH2CH2S(O)2Me |
| Cl | F | Cl | CH2CH3 |
| Cl | F | Cl | CH2-i-Pr |
| Cl | F | Cl | CH2CH2Cl |
| Cl | F | Cl | CH2CH2OH |
| Cl | F | Cl | CH(Me)CH2OH |
| Cl | F | Cl | CH2CH(Me)OH |
| Cl | F | Cl | CH2C(Me)2OH |
| Cl | F | Cl | CH2CH2CH2OH |
| Cl | F | Cl | CH2C(Me)2CH2OH |
| Cl | F | Cl | CH2CH2CH(Me)OH |
| Cl | F | Cl | CH2C(=O)N(H)Et |
| Cl | F | Cl | CH2C(=O)N(H)-i-Pr |
| Cl | F | Cl | CH2C(=O)N(H)CH2-i-Pr |
| Cl | F | Cl | CH(Me)C(=O)N(H)CH2-i-Pr |
| Cl | F | Cl | CH2C(=O)N(H)CH2CH2Cl |
| Cl | F | Cl | CH(Me)C(=O)N(H)CH2CH2Cl |
| Cl | F | Cl | CH2C(=O)N(H)CH2CH2F |
| Cl | F | Cl | CH(Me)C(=O)N(H)CH2CH2F |
| Cl | F | Cl | CH2CF3 |
| Cl | F | Cl | CH2-(2-Py) |
| Cl | F | Cl | CH2-(4-Thz) |
| Cl | F | Cl | CH2-c-Pr |
| Cl | F | Cl | CH2CH2SMe |
| Cl | F | Cl | CH(Me)CH2SMe |
| Cl | F | Cl | CH2CH2CH2SMe |
| Cl | F | Cl | CH2CH2S(=O)Me |
| Cl | F | Cl | CH(Me)CH2S(=O)Me |
| Cl | F | Cl | CH2CH2CH2S(=O)Me |
| Cl | F | Cl | CH2CH2S(O)2Me |
| Cl | F | Cl | CH(Me)CH2S(O)2Me |
| Cl | F | Cl | CH2CH2CH2S(O)2Me |
| Cl | F | Cl | CH2C(=O)N(H)CH2CF3 |
| Cl | F | Cl | CH(Me)C(=O)N(H)CH2CF3 |
| Cl | F | Cl | CH2C(=O)N(H)CH2CH2SMe |
| Cl | F | Cl | CH2C(=O)N(H)CH2CH2S(O)2Me |
| OCF3 | H | Cl | CH2CH3 |
| OCF3 | H | Cl | CH2-i-Pr |
| OCF3 | H | Cl | CH2CH2Cl |
| OCF3 | H | Cl | CH2CH2OH |
| OCF3 | H | Cl | CH(Me)CH2OH |
| OCF3 | H | Cl | CH2CH(Me)OH |
| OCF3 | H | Cl | CH2C(Me)2OH |
| OCF3 | H | Cl | CH2CH2CH2OH |
| OCF3 | H | Cl | CH2C(Me)2CH2OH |
| OCF3 | H | Cl | CH2CH2CH(Me)OH |
| OCF3 | H | Cl | CH2C(=O)N(H)Et |
| OCF3 | H | Cl | CH2C(=O)N(H)-i-Pr |
| OCF3 | H | Cl | CH2C(=O)N(H)CH2-i-Pr |
| OCF3 | H | Cl | CH(Me)C(=O)N(H)CH2-i-Pr |
| OCF3 | H | Cl | CH2C(=O)N(H)CH2CH2Cl |
| OCF3 | H | Cl | CH(Me)C(=O)N(H)CH2CH2Cl |
| OCF3 | H | Cl | CH2C(=O)N(H)CH2CH2F |
| OCF3 | H | Cl | CH(Me)C(=O)N(H)CH2CH2F |
| OCF3 | H | Cl | CH2CF3 |
| OCF3 | H | Cl | CH2-(2-Py) |
| OCF3 | H | Cl | CH2-(4-Thz) |
| OCF3 | H | Cl | CH2-c-Pr |
| OCF3 | H | Cl | CH2CH2SMe |
| OCF3 | H | Cl | CH(Me)CH2SMe |
| OCF3 | H | Cl | CH2CH2CH2SMe |
| OCF3 | H | Cl | CH2CH2S(=O)Me |
| OCF3 | H | Cl | CH(Me)CH2S(=O)Me |
| OCF3 | H | Cl | CH2CH2CH2S(=O)Me |
| OCF3 | H | Cl | CH2CH2S(O)2Me |
| OCF3 | H | Cl | CH(Me)CH2S(O)2Me |
| OCF3 | H | Cl | CH2CH2CH2S(O)2Me |
| OCF3 | H | Cl | CH2C(=O)N(H)CH2CF3 |
| OCF3 | H | Cl | CH(Me)C(=O)N(H)CH2CF3 |
| OCF3 | H | Cl | CH2C(=O)N(H)CH2CH2SMe |
| OCF3 | H | Cl | CH2C(=O)N(H)CH2CH2S(O)2Me |

TABLE 11

Z is 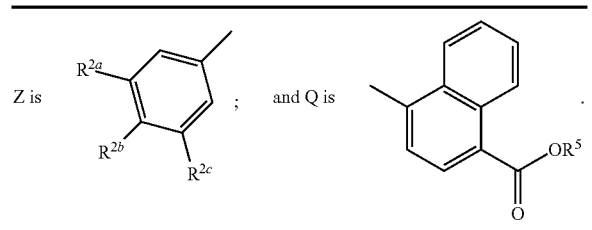 ; and Q is 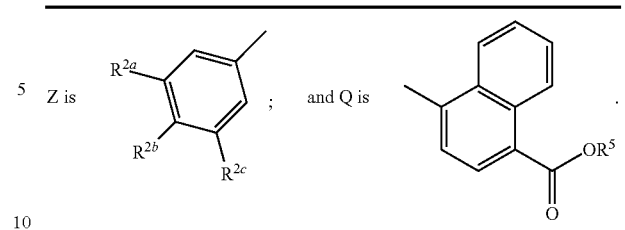 .

| $R^{2a}$ | $R^{2b}$ | $R^{2c}$ | $R^5$ |
|---|---|---|---|
| Cl | H | Cl | $CH_3$ |
| Cl | H | Cl | $CH_2CH_3$ |
| Cl | H | Cl | $CH_2$-i-Pr |
| Cl | H | Cl | n-Pr |
| Cl | H | Cl | i-Pr |
| Cl | H | Cl | s-Bu |
| Cl | H | Cl | t-Bu |
| Cl | H | Cl | $(CH_2)_5CH_3$ |
| Cl | H | Cl | $CH_2Ph$ |
| Br | H | Br | $CH_3$ |
| Br | H | Br | $CH_2CH_3$ |
| Br | H | Br | $CH_2$-i-Pr |
| Br | H | Br | n-Pr |
| Br | H | Br | i-Pr |
| Br | H | Br | s-Bu |
| Br | H | Br | t-Bu |
| Br | H | Br | $(CH_2)_5CH_3$ |
| Br | H | Br | $CH_2Ph$ |
| $CF_3$ | H | H | $CH_3$ |
| $CF_3$ | H | H | $CH_2CH_3$ |
| $CF_3$ | H | H | $CH_2$-i-Pr |
| $CF_3$ | H | H | n-Pr |
| $CF_3$ | H | H | i-Pr |
| $CF_3$ | H | H | s-Bu |
| $CF_3$ | H | H | t-Bu |
| $CF_3$ | H | H | $(CH_2)_5CH_3$ |
| $CF_3$ | H | H | $CH_2Ph$ |
| $CF_3$ | H | F | $CH_3$ |
| $CF_3$ | H | F | $CH_2CH_3$ |
| $CF_3$ | H | F | $CH_2$-i-Pr |
| $CF_3$ | H | F | n-Pr |
| $CF_3$ | H | F | i-Pr |
| $CF_3$ | H | F | s-Bu |
| $CF_3$ | H | F | t-Bu |
| $CF_3$ | H | F | $(CH_2)_5CH_3$ |
| $CF_3$ | H | F | $CH_2Ph$ |
| $CF_3$ | H | Br | $CH_3$ |
| $CF_3$ | H | Br | $CH_2CH_3$ |
| $CF_3$ | H | Br | $CH_2$-i-Pr |
| $CF_3$ | H | Br | n-Pr |
| $CF_3$ | H | Br | i-Pr |
| $CF_3$ | H | Br | s-Bu |
| $CF_3$ | H | Br | t-Bu |
| $CF_3$ | H | Br | $(CH_2)_5CH_3$ |
| $CF_3$ | H | Br | $CH_2Ph$ |
| $CF_3$ | H | Cl | $CH_3$ |
| $CF_3$ | H | Cl | $CH_2CH_3$ |
| $CF_3$ | H | Cl | $CH_2$-i-Pr |
| $CF_3$ | H | Cl | n-Pr |
| $CF_3$ | H | Cl | i-Pr |
| $CF_3$ | H | Cl | s-Bu |
| $CF_3$ | H | Cl | t-Bu |
| $CF_3$ | H | Cl | $(CH_2)_5CH_3$ |
| $CF_3$ | H | Cl | $CH_2Ph$ |
| $CF_3$ | H | $CF_3$ | $CH_3$ |
| $CF_3$ | H | $CF_3$ | $CH_2CH_3$ |
| $CF_3$ | H | $CF_3$ | $CH_2$-i-Pr |
| $CF_3$ | H | $CF_3$ | n-Pr |
| $CF_3$ | H | $CF_3$ | i-Pr |
| $CF_3$ | H | $CF_3$ | s-Bu |
| $CF_3$ | H | $CF_3$ | t-Bu |
| $CF_3$ | H | $CF_3$ | $(CH_2)_5CH_3$ |
| $CF_3$ | H | $CF_3$ | $CH_2Ph$ |
| Cl | Cl | Cl | $CH_3$ |
| Cl | Cl | Cl | $CH_2CH_3$ |
| Cl | Cl | Cl | $CH_2$-i-Pr |
| Cl | Cl | Cl | n-Pr |
| Cl | Cl | Cl | i-Pr |
| Cl | Cl | Cl | s-Bu |
| Cl | Cl | Cl | t-Bu |
| Cl | Cl | Cl | $(CH_2)_5CH_3$ |
| Cl | Cl | Cl | $CH_2Ph$ |
| Cl | F | Cl | $CH_3$ |
| Cl | F | Cl | $CH_2CH_3$ |
| Cl | F | Cl | $CH_2$-i-Pr |
| Cl | F | Cl | n-Pr |
| Cl | F | Cl | i-Pr |
| Cl | F | Cl | s-Bu |
| Cl | F | Cl | t-Bu |
| Cl | F | Cl | $(CH_2)_5CH_3$ |
| Cl | F | Cl | $CH_2Ph$ |
| $OCF_3$ | H | Cl | $CH_3$ |
| $OCF_3$ | H | Cl | $CH_2CH_3$ |
| $OCF_3$ | H | Cl | $CH_2$-i-Pr |
| $OCF_3$ | H | Cl | n-Pr |
| $OCF_3$ | H | Cl | i-Pr |
| $OCF_3$ | H | Cl | s-Bu |
| $OCF_3$ | H | Cl | t-Bu |
| $OCF_3$ | H | Cl | $(CH_2)_5CH_3$ |
| $OCF_3$ | H | Cl | $CH_2Ph$ |

TABLE 12

Z is 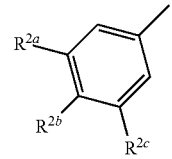 ; and Q is 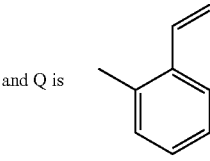 .

| $R^{2a}$ | $R^{2b}$ | $R^{2c}$ | $R^3$ |
|---|---|---|---|
| Cl | H | Cl | Cl |
| Cl | H | Cl | Br |
| Cl | H | Cl | I |
| Cl | H | Cl | OH |
| Cl | H | Cl | OMe |
| Cl | H | Cl | $OS(O)_2CF_3$ |
| Cl | H | Cl | nitro |
| Cl | H | Cl | $NH_2$ |
| Cl | H | Cl | cyano |
| Cl | H | Cl | Me |
| Cl | H | Cl | $CH_2Cl$ |
| Cl | H | Cl | $CH_2Br$ |
| Cl | H | Cl | $CH_2OH$ |
| Cl | H | Cl | $CH_2OC(O)Me$ |
| Cl | H | Cl | $CO_2H$ |
| Cl | H | Cl | n-Pr |
| Br | H | Br | Cl |
| Br | H | Br | Br |
| Br | H | Br | I |
| Br | H | Br | OH |
| Br | H | Br | OMe |
| Br | H | Br | $OS(O)_2CF_3$ |
| Br | H | Br | nitro |
| Br | H | Br | $NH_2$ |
| Br | H | Br | cyano |
| Br | H | Br | Me |
| Br | H | Br | $CH_2Cl$ |
| Br | H | Br | $CH_2Br$ |

TABLE 12-continued

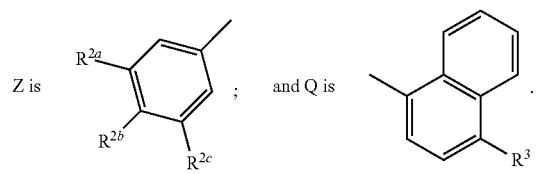

Z is ; and Q is

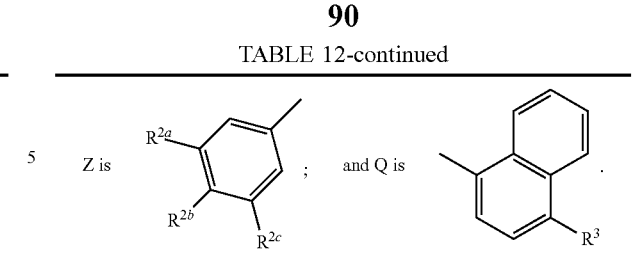

| $R^{2a}$ | $R^{2b}$ | $R^{2c}$ | $R^3$ |
|---|---|---|---|
| Br | H | Br | CH₂OH |
| Br | H | Br | CH₂OC(O)Me |
| Br | H | Br | CO₂H |
| Br | H | Br | n-Pr |
| CF₃ | H | H | Cl |
| CF₃ | H | H | Br |
| CF₃ | H | H | I |
| CF₃ | H | H | OH |
| CF₃ | H | H | OMe |
| CF₃ | H | H | OS(O)₂CF₃ |
| CF₃ | H | H | nitro |
| CF₃ | H | H | NH₂ |
| CF₃ | H | H | cyano |
| CF₃ | H | H | Me |
| CF₃ | H | H | CH₂Cl |
| CF₃ | H | H | CH₂Br |
| CF₃ | H | H | CH₂OH |
| CF₃ | H | H | CH₂OC(O)Me |
| CF₃ | H | H | CO₂H |
| CF₃ | H | H | n-Pr |
| CF₃ | H | F | Cl |
| CF₃ | H | F | Br |
| CF₃ | H | F | I |
| CF₃ | H | F | OH |
| CF₃ | H | F | OMe |
| CF₃ | H | F | OS(O)₂CF₃ |
| CF₃ | H | F | nitro |
| CF₃ | H | F | NH₂ |
| CF₃ | H | F | cyano |
| CF₃ | H | F | Me |
| CF₃ | H | F | CH₂Cl |
| CF₃ | H | F | CH₂Br |
| CF₃ | H | F | CH₂OH |
| CF₃ | H | F | CH₂OC(O)Me |
| CF₃ | H | F | CO₂H |
| CF₃ | H | F | n-Pr |
| CF₃ | H | Br | Cl |
| CF₃ | H | Br | Br |
| CF₃ | H | Br | I |
| CF₃ | H | Br | OH |
| CF₃ | H | Br | OMe |
| CF₃ | H | Br | OS(O)₂CF₃ |
| CF₃ | H | Br | nitro |
| CF₃ | H | Br | NH₂ |
| CF₃ | H | Br | cyano |
| CF₃ | H | Br | Me |
| CF₃ | H | Br | CH₂Cl |
| CF₃ | H | Br | CH₂Br |
| CF₃ | H | Br | CH₂OH |
| CF₃ | H | Br | CH₂OC(O)Me |
| CF₃ | H | Br | CO₂H |
| CF₃ | H | Br | n-Pr |
| CF₃ | H | Cl | Cl |
| CF₃ | H | Cl | Br |
| CF₃ | H | Cl | I |
| CF₃ | H | Cl | OH |
| CF₃ | H | Cl | OMe |
| CF₃ | H | Cl | OS(O)₂CF₃ |
| CF₃ | H | Cl | nitro |
| CF₃ | H | Cl | NH₂ |
| CF₃ | H | Cl | cyano |
| CF₃ | H | Cl | Me |
| CF₃ | H | Cl | CH₂Cl |
| CF₃ | H | Cl | CH₂Br |
| CF₃ | H | Cl | CH₂OH |
| CF₃ | H | Cl | CH₂OC(O)Me |
| CF₃ | H | Cl | CO₂H |
| CF₃ | H | Cl | n-Pr |
| CF₃ | H | CF₃ | Cl |
| CF₃ | H | CF₃ | Br |
| CF₃ | H | CF₃ | I |
| CF₃ | H | CF₃ | OH |
| CF₃ | H | CF₃ | OMe |
| CF₃ | H | CF₃ | OS(O)₂CF₃ |
| CF₃ | H | CF₃ | nitro |
| CF₃ | H | CF₃ | NH₂ |
| CF₃ | H | CF₃ | cyano |
| CF₃ | H | CF₃ | Me |
| CF₃ | H | CF₃ | CH₂Cl |
| CF₃ | H | CF₃ | CH₂Br |
| CF₃ | H | CF₃ | CH₂OH |
| CF₃ | H | CF₃ | CH₂OC(O)Me |
| CF₃ | H | CF₃ | CO₂H |
| CF₃ | H | CF₃ | n-Pr |
| Cl | Cl | Cl | Cl |
| Cl | Cl | Cl | Br |
| Cl | Cl | Cl | I |
| Cl | Cl | Cl | OH |
| Cl | Cl | Cl | OMe |
| Cl | Cl | Cl | OS(O)₂CF₃ |
| Cl | Cl | Cl | nitro |
| Cl | Cl | Cl | NH₂ |
| Cl | Cl | Cl | cyano |
| Cl | Cl | Cl | Me |
| Cl | Cl | Cl | CH₂Cl |
| Cl | Cl | Cl | CH₂Br |
| Cl | Cl | Cl | CH₂OH |
| Cl | Cl | Cl | CH₂OC(O)Me |
| Cl | Cl | Cl | CO₂H |
| Cl | Cl | Cl | n-Pr |
| Cl | F | Cl | Cl |
| Cl | F | Cl | Br |
| Cl | F | Cl | I |
| Cl | F | Cl | OH |
| Cl | F | Cl | OMe |
| Cl | F | Cl | OS(O)₂CF₃ |
| Cl | F | Cl | nitro |
| Cl | F | Cl | NH₂ |
| Cl | F | Cl | cyano |
| Cl | F | Cl | Me |
| Cl | F | Cl | CH₂Cl |
| Cl | F | Cl | CH₂Br |
| Cl | F | Cl | CH₂OH |
| Cl | F | Cl | CH₂OC(O)Me |
| Cl | F | Cl | CO₂H |
| Cl | F | Cl | n-Pr |
| OCF₃ | H | Cl | Cl |
| OCF₃ | H | Cl | Br |
| OCF₃ | H | Cl | I |
| OCF₃ | H | Cl | OH |
| OCF₃ | H | Cl | OMe |
| OCF₃ | H | Cl | OS(O)₂CF₃ |
| OCF₃ | H | Cl | nitro |
| OCF₃ | H | Cl | NH₂ |
| OCF₃ | H | Cl | cyano |
| OCF₃ | H | Cl | Me |
| OCF₃ | H | Cl | CH₂Cl |
| OCF₃ | H | Cl | CH₂Br |
| OCF₃ | H | Cl | CH₂OH |
| OCF₃ | H | Cl | CH₂OC(O)Me |
| OCF₃ | H | Cl | CO₂H |
| OCF₃ | H | Cl | n-Pr |

Tables 13-14 relate to the method of Scheme 2 converting compounds of Formula 5 to Grignard reagents, which are contacted with compounds of Formula 6 to prepare compounds of Formula 2. $X^1$ can be the same as or different than X, as explained in the description of the method of Scheme 2.

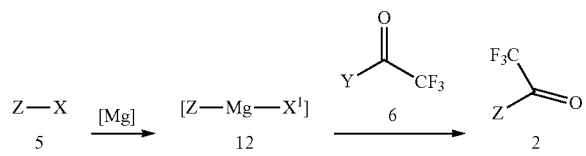

In the example transformations embodied in these tables the solvent comprises tetrahydrofuran.

TABLE 13

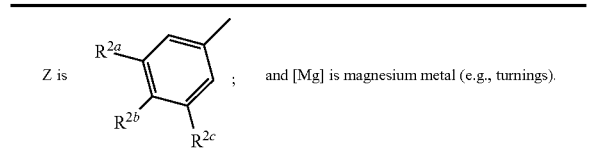

Z is [structure with $R^{2a}$, $R^{2b}$, $R^{2c}$] ; and [Mg] is magnesium metal (e.g., turnings).

| $R^{2a}$ | $R^{2b}$ | $R^{2c}$ | X | Y |
|---|---|---|---|---|
| Cl | H | Cl | I | OMe |
| Cl | H | Cl | I | OEt |
| Cl | H | Cl | I | O-i-Pr |
| Cl | H | Cl | I | O(CH$_2$)$_4$CH$_3$ |
| Cl | H | Cl | I | N(CH$_3$)$_2$ |
| Cl | H | Cl | I | N(CH$_3$)(CH$_2$CH$_3$) |
| Cl | H | Cl | I | N(-CH$_2$CH$_2$OCH$_2$CH$_2$-) |
| Cl | H | Cl | Br | OMe |
| Cl | H | Cl | Br | OEt |
| Cl | H | Cl | Br | O-i-Pr |
| Cl | H | Cl | Br | O(CH$_2$)$_4$CH$_3$ |
| Cl | H | Cl | Br | N(CH$_3$)$_2$ |
| Cl | H | Cl | Br | N(CH$_3$)(CH$_2$CH$_3$) |
| Cl | H | Cl | Br | N(-CH$_2$CH$_2$OCH$_2$CH$_2$-) |
| CF$_3$ | H | Br | I | OMe |
| CF$_3$ | H | Br | I | OEt |
| CF$_3$ | H | Br | I | O-i-Pr |
| CF$_3$ | H | Br | I | O(CH$_2$)$_4$CH$_3$ |
| CF$_3$ | H | Br | I | N(CH$_3$)$_2$ |
| CF$_3$ | H | Br | I | N(CH$_3$)(CH$_2$CH$_3$) |
| CF$_3$ | H | Br | I | N(-CH$_2$CH$_2$OCH$_2$CH$_2$-) |
| CF$_3$ | H | H | I | OMe |
| CF$_3$ | H | H | I | OEt |
| CF$_3$ | H | H | I | O-i-Pr |
| CF$_3$ | H | H | I | O(CH$_2$)$_4$CH$_3$ |
| CF$_3$ | H | H | I | N(CH$_3$)$_2$ |
| CF$_3$ | H | H | I | N(CH$_3$)(CH$_2$CH$_3$) |
| CF$_3$ | H | H | I | N(-CH$_2$CH$_2$OCH$_2$CH$_2$-) |
| CF$_3$ | H | H | Br | OMe |
| CF$_3$ | H | H | Br | OEt |
| CF$_3$ | H | H | Br | O-i-Pr |
| CF$_3$ | H | H | Br | O(CH$_2$)$_4$CH$_3$ |
| CF$_3$ | H | H | Br | N(CH$_3$)$_2$ |
| CF$_3$ | H | H | Br | N(CH$_3$)(CH$_2$CH$_3$) |
| CF$_3$ | H | H | Br | N(-CH$_2$CH$_2$OCH$_2$CH$_2$-) |
| CF$_3$ | H | H | Cl | OMe |
| CF$_3$ | H | H | Cl | OEt |
| CF$_3$ | H | H | Cl | O-i-Pr |
| CF$_3$ | H | H | Cl | O(CH$_2$)$_4$CH$_3$ |
| CF$_3$ | H | H | Cl | N(CH$_3$)$_2$ |
| CF$_3$ | H | H | Cl | N(CH$_3$)(CH$_2$CH$_3$) |
| CF$_3$ | H | H | Cl | N(-CH$_2$CH$_2$OCH$_2$CH$_2$-) |
| CF$_3$ | H | F | I | OMe |
| CF$_3$ | H | F | I | OEt |
| CF$_3$ | H | F | I | O-i-Pr |
| CF$_3$ | H | F | I | O(CH$_2$)$_4$CH$_3$ |
| CF$_3$ | H | F | I | N(CH$_3$)$_2$ |
| CF$_3$ | H | F | I | N(CH$_3$)(CH$_2$CH$_3$) |
| CF$_3$ | H | F | I | N(-CH$_2$CH$_2$OCH$_2$CH$_2$-) |
| CF$_3$ | H | F | Br | OMe |
| CF$_3$ | H | F | Br | OEt |
| CF$_3$ | H | F | Br | O-i-Pr |

TABLE 13-continued

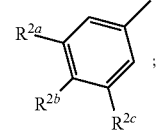

Z is [structure with $R^{2a}$, $R^{2b}$, $R^{2c}$] ; and [Mg] is magnesium metal (e.g., turnings).

| $R^{2a}$ | $R^{2b}$ | $R^{2c}$ | X | Y |
|---|---|---|---|---|
| CF$_3$ | H | F | Br | O(CH$_2$)$_4$CH$_3$ |
| CF$_3$ | H | F | Br | N(CH$_3$)$_2$ |
| CF$_3$ | H | F | Br | N(CH$_3$)(CH$_2$CH$_3$) |
| CF$_3$ | H | F | Br | N(-CH$_2$CH$_2$OCH$_2$CH$_2$-) |
| CF$_3$ | H | F | Cl | OMe |
| CF$_3$ | H | F | Cl | OEt |
| CF$_3$ | H | F | Cl | O-i-Pr |
| CF$_3$ | H | F | Cl | O(CH$_2$)$_4$CH$_3$ |
| CF$_3$ | H | F | Cl | N(CH$_3$)$_2$ |
| CF$_3$ | H | F | Cl | N(CH$_3$)(CH$_2$CH$_3$) |
| CF$_3$ | H | F | Cl | N(-CH$_2$CH$_2$OCH$_2$CH$_2$-) |
| CF$_3$ | H | Cl | I | OMe |
| CF$_3$ | H | Cl | I | OEt |
| CF$_3$ | H | Cl | I | O-i-Pr |
| CF$_3$ | H | Cl | I | O(CH$_2$)$_4$CH$_3$ |
| CF$_3$ | H | Cl | I | N(CH$_3$)$_2$ |
| CF$_3$ | H | Cl | I | N(CH$_3$)(CH$_2$CH$_3$) |
| CF$_3$ | H | Cl | I | N(-CH$_2$CH$_2$OCH$_2$CH$_2$-) |
| CF$_3$ | H | Cl | Br | OMe |
| CF$_3$ | H | Cl | Br | OEt |
| CF$_3$ | H | Cl | Br | O-i-Pr |
| CF$_3$ | H | Cl | Br | O(CH$_2$)$_4$CH$_3$ |
| CF$_3$ | H | Cl | Br | N(CH$_3$)$_2$ |
| CF$_3$ | H | Cl | Br | N(CH$_3$)(CH$_2$CH$_3$) |
| CF$_3$ | H | Cl | Br | N(-CH$_2$CH$_2$OCH$_2$CH$_2$-) |
| CF$_3$ | H | CF$_3$ | I | OMe |
| CF$_3$ | H | CF$_3$ | I | OEt |
| CF$_3$ | H | CF$_3$ | I | O-i-Pr |
| CF$_3$ | H | CF$_3$ | I | O(CH$_2$)$_4$CH$_3$ |
| CF$_3$ | H | CF$_3$ | I | N(CH$_3$)$_2$ |
| CF$_3$ | H | CF$_3$ | I | N(CH$_3$)(CH$_2$CH$_3$) |
| CF$_3$ | H | CF$_3$ | I | N(-CH$_2$CH$_2$OCH$_2$CH$_2$-) |
| CF$_3$ | H | CF$_3$ | Br | OMe |
| CF$_3$ | H | CF$_3$ | Br | OEt |
| CF$_3$ | H | CF$_3$ | Br | O-i-Pr |
| CF$_3$ | H | CF$_3$ | Br | O(CH$_2$)$_4$CH$_3$ |
| CF$_3$ | H | CF$_3$ | Br | N(CH$_3$)$_2$ |
| CF$_3$ | H | CF$_3$ | Br | N(CH$_3$)(CH$_2$CH$_3$) |
| CF$_3$ | H | CF$_3$ | Br | N(-CH$_2$CH$_2$OCH$_2$CH$_2$-) |
| CF$_3$ | H | CF$_3$ | Cl | OMe |
| CF$_3$ | H | CF$_3$ | Cl | OEt |
| CF$_3$ | H | CF$_3$ | Cl | O-i-Pr |
| CF$_3$ | H | CF$_3$ | Cl | O(CH$_2$)$_4$CH$_3$ |
| CF$_3$ | H | CF$_3$ | Cl | N(CH$_3$)$_2$ |
| CF$_3$ | H | CF$_3$ | Cl | N(CH$_3$)(CH$_2$CH$_3$) |
| CF$_3$ | H | CF$_3$ | Cl | N(-CH$_2$CH$_2$OCH$_2$CH$_2$-) |
| Cl | Cl | Cl | I | OMe |
| Cl | Cl | Cl | I | OEt |
| Cl | Cl | Cl | I | O-i-Pr |
| Cl | Cl | Cl | I | O(CH$_2$)$_4$CH$_3$ |
| Cl | Cl | Cl | I | N(CH$_3$)$_2$ |
| Cl | Cl | Cl | I | N(CH$_3$)(CH$_2$CH$_3$) |
| Cl | Cl | Cl | I | N(-CH$_2$CH$_2$OCH$_2$CH$_2$-) |
| Cl | Cl | Cl | Br | OMe |
| Cl | Cl | Cl | Br | OEt |
| Cl | Cl | Cl | Br | o-i-Pr |
| Cl | Cl | Cl | Br | O(CH$_2$)$_4$CH$_3$ |
| Cl | Cl | Cl | Br | N(CH$_3$)$_2$ |
| Cl | Cl | Cl | Br | N(CH$_3$)(CH$_2$CH$_3$) |
| Cl | Cl | Cl | Br | N(-CH$_2$CH$_2$OCH$_2$CH$_2$-) |
| Cl | F | Cl | I | OMe |
| Cl | F | Cl | I | OEt |
| Cl | F | Cl | I | O-i-Pr |
| Cl | F | Cl | I | O(CH$_2$)$_4$CH$_3$ |
| Cl | F | Cl | I | N(CH$_3$)$_2$ |
| Cl | F | Cl | I | N(CH$_3$)(CH$_2$CH$_3$) |
| Cl | F | Cl | I | N(-CH$_2$CH$_2$OCH$_2$CH$_2$-) |
| Cl | F | Cl | Br | OMe |
| Cl | F | Cl | Br | OEt |
| Cl | F | Cl | Br | O-i-Pr |

TABLE 13-continued

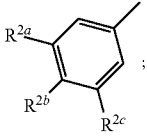

Z is (structure shown); and [Mg] is magnesium metal (e.g., turnings).

| $R^{2a}$ | $R^{2b}$ | $R^{2c}$ | X | Y |
|---|---|---|---|---|
| Cl | F | Cl | Br | $O(CH_2)_4CH_3$ |
| Cl | F | Cl | Br | $N(CH_3)_2$ |
| Cl | F | Cl | Br | $N(CH_3)(CH_2CH_3)$ |
| Cl | F | Cl | Br | $N(-CH_2CH_2OCH_2CH_2-)$ |

TABLE 14

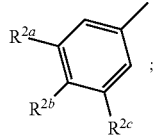

Z is (structure shown); and [Mg] is isopropylmagnesium chloride

| $R^{2a}$ | $R^{2b}$ | $R^{2c}$ | X | Y |
|---|---|---|---|---|
| Cl | H | Cl | I | OMe |
| Cl | H | Cl | I | OEt |
| Cl | H | Cl | I | O-i-Pr |
| Cl | H | Cl | I | $O(CH_2)_4CH_3$ |
| Cl | H | Cl | I | $N(CH_3)_2$ |
| Cl | H | Cl | I | $N(CH_3)(CH_2CH_3)$ |
| Cl | H | Cl | I | $N(-CH_2CH_2OCH_2CH_2-)$ |
| Cl | H | Cl | Br | OMe |
| Cl | H | Cl | Br | OEt |
| Cl | H | Cl | Br | O-i-Pr |
| Cl | H | Cl | Br | $O(CH_2)_4CH_3$ |
| Cl | H | Cl | Br | $N(CH_3)_2$ |
| Cl | H | Cl | Br | $N(CH_3)(CH_2CH_3)$ |
| Cl | H | Cl | Br | $N(-CH_2CH_2OCH_2CH_2-)$ |
| $CF_3$ | H | Br | I | OMe |
| $CF_3$ | H | Br | I | OEt |
| $CF_3$ | H | Br | I | O-i-Pr |
| $CF_3$ | H | Br | I | $O(CH_2)_4CH_3$ |
| $CF_3$ | H | Br | I | $N(CH_3)_2$ |
| $CF_3$ | H | Br | I | $N(CH_3)(CH_2CH_3)$ |
| $CF_3$ | H | Br | I | $N(-CH_2CH_2OCH_2CH_2-)$ |
| $CF_3$ | H | H | I | OMe |
| $CF_3$ | H | H | I | OEt |
| $CF_3$ | H | H | I | O-i-Pr |
| $CF_3$ | H | H | I | $O(CH_2)_4CH_3$ |
| $CF_3$ | H | H | I | $N(CH_3)_2$ |
| $CF_3$ | H | H | I | $N(CH_3)(CH_2CH_3)$ |
| $CF_3$ | H | H | I | $N(-CH_2CH_2OCH_2CH_2-)$ |
| $CF_3$ | H | H | Br | OMe |
| $CF_3$ | H | H | Br | OEt |
| $CF_3$ | H | H | Br | O-i-Pr |
| $CF_3$ | H | H | Br | $O(CH_2)_4CH_3$ |
| $CF_3$ | H | H | Br | $N(CH_3)_2$ |
| $CF_3$ | H | H | Br | $N(CH_3)(CH_2CH_3)$ |
| $CF_3$ | H | H | Br | $N(-CH_2CH_2OCH_2CH_2-)$ |
| $CF_3$ | H | H | Cl | OMe |
| $CF_3$ | H | H | Cl | OEt |
| $CF_3$ | H | H | Cl | O-i-Pr |
| $CF_3$ | H | H | Cl | $O(CH_2)_4CH_3$ |
| $CF_3$ | H | H | Cl | $N(CH_3)_2$ |
| $CF_3$ | H | H | Cl | $N(CH_3)(CH_2CH_3)$ |
| $CF_3$ | H | H | Cl | $N(-CH_2CH_2OCH_2CH_2-)$ |
| $CF_3$ | H | F | I | OMe |
| $CF_3$ | H | F | I | OEt |
| $CF_3$ | H | F | I | O-i-Pr |
| $CF_3$ | H | F | I | $O(CH_2)_4CH_3$ |
| $CF_3$ | H | F | I | $N(CH_3)_2$ |
| $CF_3$ | H | F | I | $N(CH_3)(CH_2CH_3)$ |
| $CF_3$ | H | F | I | $N(-CH_2CH_2OCH_2CH_2-)$ |
| $CF_3$ | H | F | Br | OMe |
| $CF_3$ | H | F | Br | OEt |

TABLE 14-continued

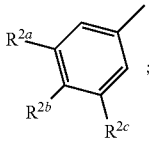

Z is (structure shown); and [Mg] is isopropylmagnesium chloride

| $R^{2a}$ | $R^{2b}$ | $R^{2c}$ | X | Y |
|---|---|---|---|---|
| $CF_3$ | H | F | Br | O-i-Pr |
| $CF_3$ | H | F | Br | $O(CH_2)_4CH_3$ |
| $CF_3$ | H | F | Br | $N(CH_3)_2$ |
| $CF_3$ | H | F | Br | $N(CH_3)(CH_2CH_3)$ |
| $CF_3$ | H | F | Br | $N(-CH_2CH_2OCH_2CH_2-)$ |
| $CF_3$ | H | F | Cl | OMe |
| $CF_3$ | H | F | Cl | OEt |
| $CF_3$ | H | F | Cl | O-i-Pr |
| $CF_3$ | H | F | Cl | $O(CH_2)_4CH_3$ |
| $CF_3$ | H | F | Cl | $N(CH_3)_2$ |
| $CF_3$ | H | F | Cl | $N(CH_3)(CH_2CH_3)$ |
| $CF_3$ | H | F | Cl | $N(-CH_2CH_2OCH_2CH_2-)$ |
| $CF_3$ | H | Cl | I | OMe |
| $CF_3$ | H | Cl | I | OEt |
| $CF_3$ | H | Cl | I | O-i-Pr |
| $CF_3$ | H | Cl | I | $O(CH_2)_4CH_3$ |
| $CF_3$ | H | Cl | I | $N(CH_3)_2$ |
| $CF_3$ | H | Cl | I | $N(CH_3)(CH_2CH_3)$ |
| $CF_3$ | H | Cl | I | $N(-CH_2CH_2OCH_2CH_2-)$ |
| $CF_3$ | H | Cl | Br | OMe |
| $CF_3$ | H | Cl | Br | OEt |
| $CF_3$ | H | Cl | Br | O-i-Pr |
| $CF_3$ | H | Cl | Br | $O(CH_2)_4CH_3$ |
| $CF_3$ | H | Cl | Br | $N(CH_3)_2$ |
| $CF_3$ | H | Cl | Br | $N(CH_3)(CH_2CH_3)$ |
| $CF_3$ | H | Cl | Br | $N(-CH_2CH_2OCH_2CH_2-)$ |
| $CF_3$ | H | $CF_3$ | I | OMe |
| $CF_3$ | H | $CF_3$ | I | OEt |
| $CF_3$ | H | $CF_3$ | I | O-i-Pr |
| $CF_3$ | H | $CF_3$ | I | $O(CH_2)_4CH_3$ |
| $CF_3$ | H | $CF_3$ | I | $N(CH_3)_2$ |
| $CF_3$ | H | $CF_3$ | I | $N(CH_3)(CH_2CH_3)$ |
| $CF_3$ | H | $CF_3$ | I | $N(-CH_2CH_2OCH_2CH_2-)$ |
| $CF_3$ | H | $CF_3$ | Br | OMe |
| $CF_3$ | H | $CF_3$ | Br | OEt |
| $CF_3$ | H | $CF_3$ | Br | O-i-Pr |
| $CF_3$ | H | $CF_3$ | Br | $O(CH_2)_4CH_3$ |
| $CF_3$ | H | $CF_3$ | Br | $N(CH_3)_2$ |
| $CF_3$ | H | $CF_3$ | Br | $N(CH_3)(CH_2CH_3)$ |
| $CF_3$ | H | $CF_3$ | Br | $N(-CH_2CH_2OCH_2CH_2-)$ |
| $CF_3$ | H | $CF_3$ | Cl | OMe |
| $CF_3$ | H | $CF_3$ | Cl | OEt |
| $CF_3$ | H | $CF_3$ | Cl | O-i-Pr |
| $CF_3$ | H | $CF_3$ | Cl | $O(CH_2)_4CH_3$ |
| $CF_3$ | H | $CF_3$ | Cl | $N(CH_3)_2$ |
| $CF_3$ | H | $CF_3$ | Cl | $N(CH_3)(CH_2CH_3)$ |
| $CF_3$ | H | $CF_3$ | Cl | $N(-CH_2CH_2OCH_2CH_2-)$ |
| Cl | Cl | Cl | I | OMe |
| Cl | Cl | Cl | I | OEt |
| Cl | Cl | Cl | I | O-i-Pr |
| Cl | Cl | Cl | I | $O(CH_2)_4CH_3$ |
| Cl | Cl | Cl | I | $N(CH_3)_2$ |
| Cl | Cl | Cl | I | $N(CH_3)CH_2CH_3$ |
| Cl | Cl | Cl | I | $N(-CH_2CH_2OCH_2CH_2-)$ |
| Cl | Cl | Cl | Br | OMe |
| Cl | Cl | Cl | Br | OEt |
| Cl | Cl | Cl | Br | O-i-Pr |
| Cl | Cl | Cl | Br | $O(CH_2)_4CH_3$ |
| Cl | Cl | Cl | Br | $N(CH_3)_2$ |
| Cl | Cl | Cl | Br | $N(CH_3)(CH_2CH_3)$ |
| Cl | Cl | Cl | Br | $N(-CH_2CH_2OCH_2CH_2-)$ |
| Cl | F | Cl | I | OMe |
| Cl | F | Cl | I | OEt |
| Cl | F | Cl | I | O-i-Pr |
| Cl | F | Cl | I | $O(CH_2)_4CH_3$ |
| Cl | F | Cl | I | $N(CH_3)_2$ |
| Cl | F | Cl | I | $N(CH_3)(CH_2CH_3)$ |
| Cl | F | Cl | I | $N(-CH_2CH_2OCH_2CH_2-)$ |
| Cl | F | Cl | Br | OMe |
| Cl | F | Cl | Br | OEt |

TABLE 14-continued

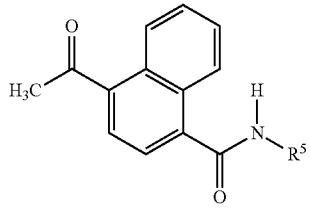

Z is ; and [Mg] is isopropylmagnesium chloride

| $R^{2a}$ | $R^{2b}$ | $R^{2c}$ | X | Y |
|---|---|---|---|---|
| Cl | F | Cl | Br | O-i-Pr |
| Cl | F | Cl | Br | $O(CH_2)_4CH_3$ |
| Cl | F | Cl | Br | $N(CH_3)_2$ |
| Cl | F | Cl | Br | $N(CH_3)(CH_2CH_3)$ |
| Cl | F | Cl | Br | $N(-CH_2CH_2OCH_2CH_2-)$ |

The following compounds of Formula 3 defined in Table 15 are of particular note as intermediates for preparing the corresponding compounds of Formula 1 as shown in Schemes 1, 1a and 1b by the procedures described herein together with methods known in the art.

TABLE 15

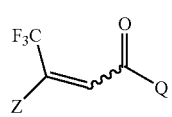

| $R^5$ | $R^5$ | $R^5$ |
|---|---|---|
| $CH_2CH_3$ | $CH_2$-c-Pr | $CH_2CH_2SO_2Et$ |
| $CH_2$-i-Pr | $CH_2CH_2SMe$ | $CH_2CH_2SO_2(n-Pr)$ |
| $CH_2CH_2Cl$ | $CH(Me)CH_2SMe$ | $CH_2CH_2CH_2SO_2Et$ |
| $CH_2CH_2OH$ | $CH_2CH_2CH_2SMe$ | $CH_2C(O)NH(Me)$ |
| $CH(Me)CH_2OH$ | $CH_2CH_2S(O)Me$ | $CH_2C(O)NH(n-Pr)$ |
| $CH_2CH(Me)OH$ | $CH(Me)CH_2S(O)Me$ | $CH_2C(O)NH(s-Bu)$ |
| $CH_2C(Me)_2OH$ | $CH_2CH_2CH_2S(O)Me$ | $CH_2C(O)NMe_2$ |
| $CH_2CH_2CH_2OH$ | $CH_2CH_2SO_2Me$ | $CH_2C(O)NMe(Et)$ |
| $CH_2C(Me)_2CH_2OH$ | $CH(Me)CH_2SO_2Me$ | $CH(Me)C(O)NH(Me)$ |
| $CH_2CH_2CH(Me)OH$ | $CH_2CH_2CH_2SO_2Me$ | $CH(Me)C(O)NH(Et)$ |
| $CH_2C(O)N(H)Et$ | $CH_2C(O)N(H)CH_2CF_3$ | $CH(Me)C(O)NH(n-Pr)$ |
| $CH_2C(O)N(H)$-i-Pr | $CH(Me)C(O)N(H)CH_2CF_3$ | $CH(Me)C(O)NH(i-Pr)$ |
| $CH_2C(O)N(H)CH_2$-i-Pr | $CH_2C(O)N(H)CH_2CH_2SMe$ | $CH(Me)C(O)NH(s-Bu)$ |
| $CH(Me)C(O)N(H)CH_2$-i-Pr | $CH_2C(O)N(H)CH_2CH_2SO_2Me$ | $CH_2C(O)NHCH_2CHF_2$ |
| $CH_2C(O)N(H)CH_2CH_2Cl$ | | $CH_2C(O)NHCH_2CH_2CF_3$ |
| $CH(Me)C(O)N(H)CH_2CH_2Cl$ | $CH_2CH_2SEt$ | $CH_2C(O)NHCH(Me)CF_3$ |
| $CH_2C(O)N(H)CH_2CH_2F$ | $CH_2CH_2S(n-Pr)$ | $CH_2C(O)NHCH_2CH(Me)CF_3$ |
| $CH(Me)C(O)N(H)CH_2CH_2F$ | $CH_2CH_2CH_2SEt$ | $CH(Me)C(O)NHCH_2CHF_2$ |
| $CH_2CF_3$ | $CH_2CH_2S(O)Et$ | $CH(Me)C(O)NHCH_2CH_2CF_3$ |
| $CH_2$-(2-Py) | $CH_2CH_2S(O)(n-Prj)$ | $CH(Me)C(O)NHCH(Me)CF_3$ |
| $CH_2$-(4-Thz) | $CH_2CH_2CH_2S(O)Et$ | $CH(Me)C(O)NHCH_2CH(Me)CF_3$ |

What is claimed is:

1. A method for preparing a compound of Formula 1

wherein,
Z is optionally substituted phenyl; and
Q is phenyl or 1-naphthalenyl, each optionally substituted;

comprising distilling water from a mixture, comprising a compound of Formula 2

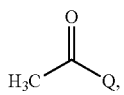

a compound of Formula 3

$$\underset{H_3C}{\overset{O}{\underset{\|}{\text{C}}}}_{Q,} \quad 3$$

a base comprising at least one compound selected from the group consisting of
1,5-diazabicyclo[4.3.0]non-5-ene and 1,8-diazabicyclo[5.4.0]undec-7-ene, and
an aprotic solvent capable of forming a low-boiling azeotrope with water;
wherein the aprotic solvent capable of forming a low-boiling azeotrope with water comprises acetonitrile.

2. The method of claim 1 wherein the base comprises 1,5-diazabicyclo[4.3.0]non-5-ene.

3. The method of claim 1 wherein
Z is phenyl optionally substituted with up to 5 substituents independently selected from $R^2$;
Q is phenyl or 1-naphthalenyl, each optionally substituted with up to four substituents independently selected from $R^3$;
each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$;

each $R^3$ is independently halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_3$-$C_6$ cycloalkyl, $C_2$-$C_6$ halocycloalkyl, $C_1$-$C_6$ alkoxy, $C_1$-$C_6$ haloalkoxy, $C_1$-$C_6$ alkylthio, $C_2$-$C_7$ alkylcarbonyl, $C_2$-$C_7$ haloalkylcarbonyl, $C_1$-$C_6$ haloalkylthio, $C_1$-$C_6$ alkysulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(=W)N($R^4$)$R^5$, —C(=W)O$R^5$, —CN, —O$R^{11}$ or —NO$_2$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N($R^4$)$R^5$, —C(=W)N($R^4$)$R^5$, —C(=O)O$R^5$ and $R^7$;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ halodialkylaminocarbonyl, —OH, —NH$_2$, —CN or —NO$_2$; or $Q^1$;

each $R^7$ is independently a phenyl ring or a pyridinyl ring, each ring optionally substituted with one or more substituents independently selected from $R^8$;

each $R^8$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —C(=O)OH, —CN or —NO$_2$;

each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, —C(=W)N($R^9$)$R^{10}$ and —C(=O)O$R^{10}$;

each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;

each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and each W is independently O or S.

4. The method of claim 3 wherein
Z is

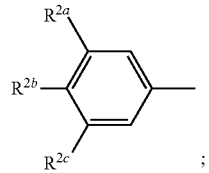

Q is

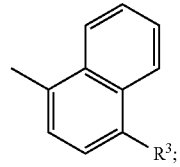

$R^{2a}$ is halogen, $C_1$-$C_2$ haloalkyl or $C_1$-$C_2$ haloalkoxy;
$R^{2b}$ is H, halogen or cyano;
$R^{2c}$ is H, halogen or CF$_3$;
$R^3$ is C(O)N($R^4$)$R^5$ or C(O)O$R^{5a}$;
$R^4$ is H, $C_2$-$C_7$ alkylcarbonyl or $C_2$-$C_7$ alkoxycarbonyl; and
$R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl; and
$R^{5a}$ is $C_1$-$C_6$ alkyl, $C_2$-$C_6$ alkenyl or $C_2$-$C_6$ alkynyl, each optionally substituted with one or more substituents independently selected from halogen, $C_1$-$C_2$ alkoxy and phenyl optionally substituted with up to 5 substituents selected from halogen and $C_1$-$C_3$ alkyl.

5. The method of claim 1 wherein
Z is phenyl optionally substituted with up to 5 substituents independently selected from $R^2$; and
each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio;

further comprising preparing the compound of Formula 2 by
(1) forming a reaction mixture comprising a Grignard reagent derived from a compound of Formula 5

$$Z-X \qquad\qquad 5$$

wherein X is Cl, Br or I,
by contacting the compound of Formula 5 with
(a) magnesium metal, or
(b) an alkylmagnesium halide
in the presence of an ethereal solvent; and then
(2) contacting the reaction mixture with a compound of Formula 6

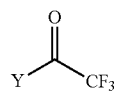

wherein
Y is O$R^{11}$ or N$R^{12}R^{13}$;
$R^{11}$ is $C_1$-$C_5$ alkyl; and
$R^{12}$ and $R^{13}$ are independently $C_1$-$C_2$ alkyl; or $R^{12}$ and $R^{13}$ are taken together as —CH$_2$CH$_2$OCH$_2$CH$_2$—.

6. The method of claim 5 wherein Z is
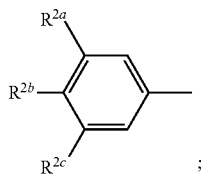
$R^{2a}$ is F, Cl, Br, $C_1$-$C_2$ fluoroalkyl or $C_1$-$C_2$ fluoroalkoxy;
$R^{2b}$ is H, F, Cl or Br; and
$R^{2c}$ is H, F, Cl, Br or $CF_3$.
7. The method of claim 1 wherein the base comprises 1,8-diazabicyclo[5.4.0]undec-7-ene.
8. The method of claim 1 wherein the base comprises a mixture of 1,5-diazabicyclo[4.3.0]non-5-ene, 1,8-diazabicyclo[5.4.0]undec-7-ene.
\* \* \* \* \*

UNITED STATES PATENT AND TRADEMARK OFFICE
CERTIFICATE OF CORRECTION

PATENT NO.         : 10,160,731 B2                                          Page 1 of 1
APPLICATION NO.    : 15/946601
DATED              : December 25, 2018
INVENTOR(S)        : Gary David Annis It is certified that error appears in the above-identified patent and that said Letters Patent is hereby corrected as shown below:

In the Claims

In Claim 3 at Column 97, Line 3: "$C_2$-$C_6$" should read --$C_3$-$C_6$--.

Signed and Sealed this
Twenty-sixth Day of February, 2019

Andrei Iancu
*Director of the United States Patent and Trademark Office*